United States Patent [19]

Chambers et al.

[11] Patent Number: 5,360,802
[45] Date of Patent: Nov. 1, 1994

[54] BENZODIAZEPINE DERIVATIVES, COMPOSITIONS CONTAINING THEM AND THEIR USE IN THERAPY

[75] Inventors: Mark S. Chambers, Watford; Victor G. Matassa, Furneux Pelham; Stephen R. Fletcher, Bishops Stortford, all of England

[73] Assignee: Merck Sharpe & Dohme Ltd., Hoddesdon

[21] Appl. No.: 976,042

[22] Filed: Nov. 13, 1992

Related U.S. Application Data

[63] Continuation-in-part of Ser. No. 880,864, May 11, 1992, abandoned.

[51] Int. Cl.$^5$ .................. A61K 31/55; C07D 243/24; C07D 243/10
[52] U.S. Cl. ..................... 514/221; 540/509
[58] Field of Search ................. 540/509; 514/221

[56] References Cited

U.S. PATENT DOCUMENTS

| | | | |
|---|---|---|---|
| 4,820,834 | 4/1989 | Evans et al. | 540/504 |
| 5,010,076 | 4/1991 | Waldeck et al. | 514/221 |

FOREIGN PATENT DOCUMENTS

| | | | |
|---|---|---|---|
| 167919 | 6/1985 | European Pat. Off. | 540/504 |
| 284256 | 9/1988 | European Pat. Off. | 540/504 |
| 387618 | 3/1988 | European Pat. Off. | |
| 0304223 | 2/1989 | European Pat. Off. | 540/504 |
| 0411668 | 2/1991 | European Pat. Off. | 540/504 |
| 0434364 | 6/1991 | European Pat. Off. | 540/504 |
| 0434369 | 6/1991 | European Pat. Off. | 540/504 |
| WO92/01683 | 2/1992 | WIPO | 540/509 |

OTHER PUBLICATIONS

V. Mutt, Gastrointestinal Hormones, G. B. J. Green, Ed., Raven Press, N.Y. p. 169 and G. Nission, ibid p. 127.
Mutt and Jorpes, Biochem. J. 125 678 (1981).
A. J. Stunkard and E. Stellar, Eds. Raven Press, New York, 1984, p. 67.
A. J. Prange, et al., "Peptides in the Central Nervous System", Ann Repts. Med. Chem. 17, 31, 33 91982).
J. A. Williams, Biomed. Res. 3 107 (1982).
J. E. Morley, Life, Sci. 30, 479 (1982).
T. H. Moran, et al "Two Brain cholecystokinin receptors: implications for behavoural actions", Brain Res., 175–79 (1986).
P. L. Faris, et al Science, 226 1215 (1984).
M. F. O'Neill, et al., Brain Research, 534 287 (1990).
Rasmusson, et al., (1991) Eur. J. Pharmacol., 209, 135–38.
Woodruff, et al., 1991, Neuropeptides 19, 45–46.
Cervo, et al., 1988 Eur. J. Pharmacol., 158, 53–59.
Singh, et al 1992, Br. J. Pharmacol., 105 8–10.
K. Okyama, Hokkaido J. Med. Sci., 206–216 (1985).
Xu, et al., Peptides, 8, (1987) 769–772.
A. Bill, et al., Acta Physiol. Scand., 138 479–485 (1990).
M. Bock, et al., J. Med. Chem., 32 13–16 (1989).
Beauchamp, et al., Ann. Surg., 202, 203 (1985) (Cumulative).
Soc. Neurosci. Abstr., vol. 14, p. 291 (1988) by Bradwejn, et al.
Soc. Neurosci. Abstr., vol. 14, p. 291 (1988), by de Montigny.
Nature, vol. 312, p. 22 (1984), by Bradwejn, et al.
Arch. Gen Psych., vol. 46, pp. 511–517 (1989), by de Montigny.
Eur. J. of Pharma., vol. 147, pp. 469∫472 (1988), by Dourish, et al.
Eur. J. of Pharma., vol. 151, pp. 135–138 (1988), by Bouthillier, et al.
Neuropharmacology, vol. 28, No. 3, pp. 243–247 (1989), by O'Neill, et al.
Proc. Natl. Acad. Sci., vol. 83, pp. 4923–4926 (1986), by Chang, et al.
J. of Med. Chem., vol. 32, No. 1, pp. 13∫16 (Jan. 1989), by Bock et al.

Primary Examiner—Robert T. Bond
Attorney, Agent, or Firm—Robert J. North; Melvin Winokur

[57] ABSTRACT

This invention relates to benzodiazepine compounds which are useful as antagonists of cholecystokinin and gastrin.

15 Claims, No Drawings

BENZODIAZEPINE DERIVATIVES, COMPOSITIONS CONTAINING THEM AND THEIR USE IN THERAPY

CROSS-REFERENCE TO RELATED APPLICATIONS

The instant application is a continuation-in-part of U.S. Ser. No. 07/880,864, filed May 11, 1992, now abandoned.

Cholecystokinins (CCK) and gastrin are structurally related peptides which exist in gastrointestinal tissue and in the central nervous system (see, V. Mutt, *Gastrointestinal Hormones*, G. B. J. Green, Ed., Raven Press, N.Y., p. 169 and G. Nission, ibid. p. 127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-$NH_2$, which is the common structural element shared by both CCK and gastrin.

CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem* 17, 31, 33 [1982] and references cited therein; J. A. Williams, *Biomed Res.* 3 107 [1982]; and J. E. Morley, *Life Sci.* 30, 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholescystokinin receptors termed CCK-A and CCK-B (T. H. Moran et al., "Two brain cholecystokinin receptors: implications for behavoural actions", *Brain Res.*, 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; Cervo et. al., 1988, *Eur. J. Pharmacol.*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, $\beta$-endorphin, vasopressin and oxytocin, CCK may function as a mediator of responses to stress and as part of the arousal system. CCK-A receptors are now known to be present in a number of areas of the CNS and may be involved in modulating all of the above.

CCK may be involved in the regulation of stress and its relationship with drug abuse e.g. alleviation of the benzodiazepine withdrawal syndrome (Singh et. al., 1992, *Br. J. Pharmacol.*, 105, 8–10) and neuroadaptive processes.

Since CCK and gastrin also have trophic effects on certain tumours [K. Okyama, *Hokkaido J. Med. Sci.*, 206–216 (1985)], antagonists of CCK and gastrin are useful in treating these tumours [see, R. D. Beauchamp et al., *Ann. Surg.*, 202, 203 (1985)].

In the light of discussion in C. Xu et al., *Peptides*, 8, 1987, 769–772, CCK antagonists may also be effective in neuroprotection.

CCK receptor antagonists have been found to inhibit the contractile effects of CCK on iris sphincter and ciliary muscles of monkey and human eyes (Eur. J. Pharmacol., 211(2), 183–187; A. Bill et al., Acta Physiol. Scand., 138, 479–485 [1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al., *J. Med Chem.*, 32, 13–16 (1989)].

European patent application No. 0 167 919 discloses benzodiazepine CCK and gastrin antagonists substituted in the 3-position by, inter alia, a phenyl urea; however, 5-cycloalkyl substitution is not disclosed.

The present invention provides benzodiazepine compounds of formula (I):

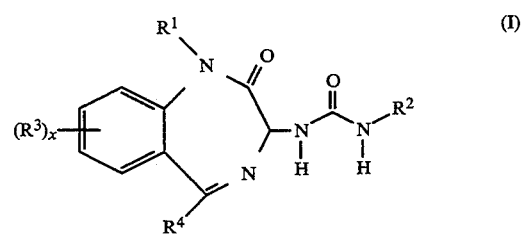

wherein:

R$^1$ represents (CH$_2$)$_q$imidazolyl, (CH$_2$)$_q$tetrazolyl, (CH$_2$)$_q$triazolyl; C$_{1-6}$alkyl optionally substituted by one or more groups selected from halo, hydroxy and NR$^6$R$^7$; C$_{3-7}$cycloalkyl; cyclopropylmethyl; CH$_2$CO$_2$R$^5$; CH$_2$CONR$^6$R$^7$; or CH$_2$CH(OH)-W-(CH$_2$)$_2$NR$^6$R$^7$ where R$^5$ represents C$_{1-4}$alkyl, R$^6$ and R$^7$ each independently represents a hydrogen atom or a C$_{1-4}$alkyl group, or taken together with the nitrogen atom to which they are attached form a pyrrolidinyl, or piperidinyl ring, q is 1, 2 or 3, and W is S or NH;

R$^2$ represents:

(i) a phenyl group optionally substituted by one or more substituents selected from C$_{1-6}$alkyl optionally substituted by hydroxy, CONR$^a$R$^b$, CO$_2$R$^a$ or OCONR$^a$ R$^b$; C$_{2-6}$alkenyl optionally substituted by CO$_2$R$^a$; C$_{2-6}$alkynyl; halo; optionally protected hydroxy; NHR$^8$; NHPO(OC$_{1-4}$alkyl); (CH$_2$)$_n$tetrazolyl optionally substituted in the tetrazolyl ring by C$_{1-4}$alkyl; (CH$_2$)$_n$imidazolyl; CONH-tetrazolyl; CONH-triazolyl; diazolizone; triazolinone optionally substituted by methyl; tetrazolinone; oxathiadiazolone; 5-hydroxy-4-pyrone; CONH$_2$; CONHCOR$^9$; SO(C$_{1-6}$alkyl); SO$_2$(C$_{1-6}$alkyl); CONHCO$_2$R$^9$; CONHCONHR$^9$; C(NH$_2$)NOH; COC$_{1-4}$alkyl; CONHSO$_2$R$^9$; SO$_2$NH$_2$; NHSO$_2$NH$_2$; SO$_2$NHCO$_2$R$^9$; SO$_2$NHCONHR$^9$; SO$_2$N-HSO$_2$R$^9$; SO$_2$NHPO(OR$^a$R$^b$); SO$_2$NHR$^{10}$; cyano; B(OH)$_2$; CO$_2$H; CH$_2$OCH$_2$O (CH$_2$)$_2$OCH$_3$, where R$^a$ and R$^b$ each independently represent H or C$_{1-6}$alkyl, n is 0, 1 or 2, R$^8$ represents H or COC$_{1-6}$alkyl, R$^9$ represents C$_{1-6}$alkyl, optionally substituted aryl, 2,2-difluorocyclopropane or trifluoromethyl, and R$^{10}$ represents a nitrogen containing heterocycle;

(ii) a group

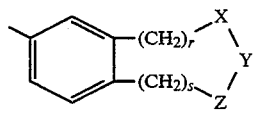

wherein X and Z each independently represent CH$_2$, O, SO$_2$, C=O, NH or N; and Y represents CH$_2$, C=O, NR$^a$ or N, where R$^a$ is as above defined;

r and s each independently represent 0 or 1;

and the dotted line represents an optional double bond;

provided that: X and Z can only be the same when they are O, and when one of X and Z is O, the other of X and Z must be O;

when X or Z is N, Y is also N and the ring contains one unit of unsaturation;

when X or Z is SO$_2$, Y is NH and the other of X and Z is C=O;

when X or Z is SO$_2$, Y is NH and the other of X and Z is C=O, whichever of r and s is adjacent to SO$_2$ may be 1; otherwise r and s are the same and O;

(iii) a pyridyl group substituted by C$_{1-4}$alkoxy or halo;

R$^3$ represents C$_{1-6}$ alkyl or halo;

R$^4$ represents C$_{3-7}$ cycloalkyl;

x is 0, 1, 2 or 3;

and pharmaceutically acceptable salts and prodrugs thereof.

It will be appreciated that formula (I) is intended to embrace all possible isomers, including optical isomers, and mixtures thereof, including racemates.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bungaard, Elsevier, 1985.

As used herein, alkyl means linear or branched chain alkyl. EXamples of suitable alkyl groups include methyl, ethyl, isopropyl and isobutyl groups.

When R$^1$ represents cycloalkyl, examples include cyclopropyl, cyclopentyl and cyclohexyl groups, preferably, cyclopropyl.

Halo includes fluoro, chloro and bromo. Preferably halo is fluoro or chloro.

Preferably R$^2$ represents a mono- or disubstituted phenyl group.

When R$^2$ represents a monosubstituted phenyl group, the substituent is preferably in the 3- or 4-position of the phenyl ring, more preferably the 3-position.

When R$^2$ represents a disubstituted phenyl group the substituents are preferably in the 3- and 4-positions of the phenyl ring.

When R$^2$ represents the group,

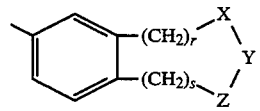

suitable values of R$^2$ include

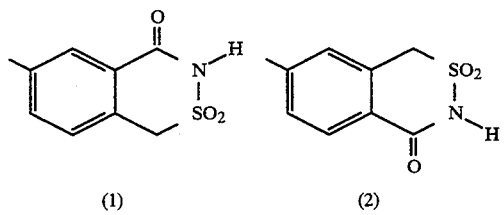

(1)　　　　　　(2)

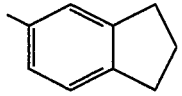 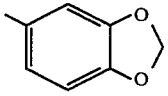

(3)　　　　　　(4)

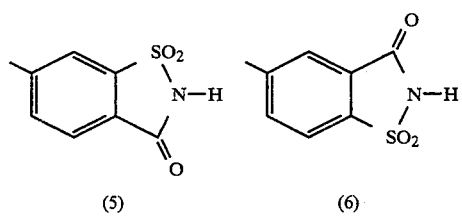

(5)　　　　　　(6)

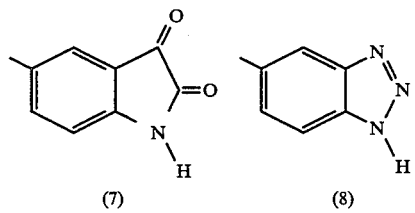

(7)　　　　　　(8)

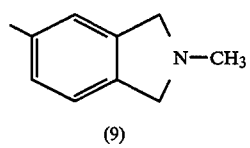

(9)

Preferred are values for $R^2$ corresponding to the structures numbered (1), (2) and (3) above, especially those numbered (1) and (2).

Suitably $R^4$ represents cyclohexyl, cyclopentyl or cyclobutyl, preferably cyclohexyl or cyclopentyl.

A particular sub-group of compounds according to the invention is represented by compounds of formula (Ia), and salts and prodrugs thereof:

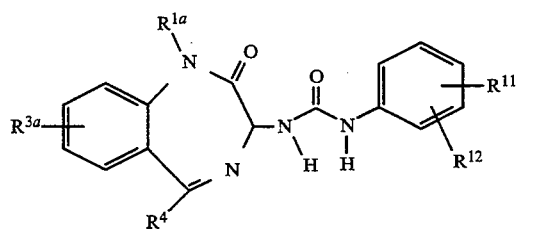

wherein:

$R^{1a}$ represents $C_{1-6}$ alkyl;

$R^{3a}$ represents hydrogen;

$R^4$ represents $C_{3-7}$ cycloalkyl;

$R^{11}$ represents hydrogen or $C_{1-6}$ alkyl;

$R^{12}$ represents $C_{1-6}$ alkyl, halo, $(CH_2)_n$-tetrazolyl, optionally substituted by $C_{1-4}$alkyl, $(CH_2)_n$-imidazolyl, 5-hydroxy-4-pyrone, $SO(C_{1-6}alkyl)$ $CONHSO_2R^{9a}$, $SO_2NHCOR^{9a}$ (where $R^{9a}$ is $C_{1-6}$ alkyl, optionally substituted aryl or trifluoromethyl), $SO_2NHR^{10a}$ (where $R^{10a}$ is a nitrogen containing heterocycle) or a group

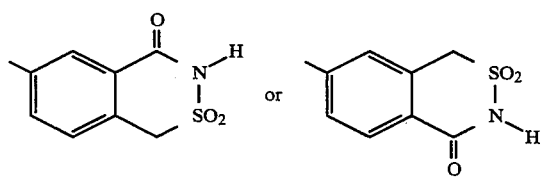

When $R^{9a}$ is optionally substituted aryl, this will preferably be optionally substituted phenyl. Suitable substituents include $C_{1-4}$alkyl, $C_{1-4}$alkoxy, halo and trifluoromethyl.

When $R^{9a}$ is $C_{1-6}$alkyl, it will preferably represent $C_{1-4}$alkyl. Particularly preferred are methyl and isopropyl, especially iso-propyl.

Suitable values for $R^{9a}$ include methyl, ethyl, i-propyl, t-butyl, optionally substituted phenyl and trifluoromethyl. Where $R^{9a}$ is substituted phenyl, preferably the phenyl substituent is $C_{1-4}$alkyl, more preferably methyl.

Preferably $R^{11}$ is H or methyl.

In one preferred group of compounds of formula Ia, $R^{11}$ is H and $R^{12}$ is 3-tetrazol-5-yl.

In a further preferred group of compounds of formula Ia, $R^{12}$ is $CONHSO_2R^{9a}$ or $SO_2NHCOR^{9a}$, more preferably $CONHSO_2R^{9a}$.

When $R^{12}$ is $SO_2NHR^{10a}$, suitable values of $R^{10}$ include, for example, thiazole, thiadiazole and pyrazine.

Preferably m is 1.

Preferably n is zero. Preferably $R^4$ is cyclobutyl, cyclopentyl or cyclohexyl.

A further subclass of compounds according to the invention is represented by formula (Ib)

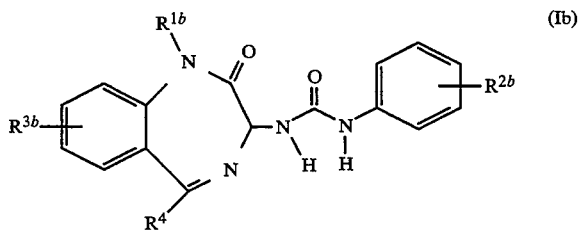

and salts and prodrugs thereof, wherein $R^{1b}$ represents $C_{1-6}$ alkyl, $C_{3-7}$ cycloalkyl, cyclopropylmethyl, $(CH_2)_m$-imidazolyl (where m is 1 or 2), $CH_2CO_2R^6$ (where $R^6$ is $C_{1-4}$ alkyl) or a group $CH_2CONR^7R^8$ (where $R^7$ and $R^8$ each independently represents a hydrogen atom or a $C_{1-4}$alkyl group, or $R^7$ and $R^8$ together form a chain $(CH_2)_p$ where p is 4 or 5);

$R^{2b}$ represents hydrogen, $C_{1-6}$ alkyl, halo, $(CH_2)_n$-tetrazolyl optionally substituted by $C_{1-4}$alkyl, $(CH_2)_n$-imidazolyl, $CONHSO_2R^{9b}$, $SO_2NHCOR^{9b}$ (where $R^{9b}$ is $C_{1-6}$ alkyl, optionally substituted aryl or trifluoromethyl), $SO_2NHR^{10b}$ (where $R^{10b}$ is a nitrogen containing heterocycle) or a group $(CH_2)_nCO_2H$, n is zero, 1 or 2;

$R^{3b}$ represents hydrogen, $C_{1-6}$ alkyl or halo;

$R^4$ represents $C_{3-7}$ cycloalkyl.

One subgroup of compounds according to formula (Ib) are those wherein $R^{2b}$ represents hydrogen, $C_{1-6}$ alkyl, halo, $(CH_2)_n$-tetrazolyl, $(CH_2)_n$-imidazolyl, $CONHSO_2R^{9b}$, $SO_2NHCOR^{9b}$ (where $R^{9b}$ is $C_{1-4}$ alkyl, optionally substituted aryl or trifluoromethyl) or a group $(CH_2)_nCO_2H$, n is zero, 1 or 2;

A further subgroup of compounds according to formula (Ib) are those wherein $R^{2b}$ represents $C_{1-6}$ alkyl, halo, $(CH_2)_n$-tetrazolyl, $(CH_2)_n$-imidazolyl or a group $(CH_2)_nCO_2H$, n is zero, 1 or 2.

A yet further subgroup of compounds according to formula (Ib) and the abovementioned subgroups thereof are compounds wherein $R^{1b}$ is $C_{1-6}$alkyl; $R^{3b}$ is hydrogen and $R^4$ is $C_{3-7}$cycloalkyl.

Preferably the salts of the compounds of formula (I) are pharmaceutically acceptable, but non-pharmaceutically acceptable salts may be used for the preparation of pharmaceutically acceptable salts. The pharmaceutically acceptable salts of the compounds of formula(I) include the conventional non-toxic salts or the quaternary ammonium salts of the compounds from formula (I) formed, e.g., from inorganic or organic acids or bases. For example, such conventional non-toxic salts include those derived from inorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic.

The pharmaceutically acceptable salts of the present invention can be synthesized from the compound of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

For example, an acid of formula (I) may be reacted with an appropriate amount of a base, such as an alkali or alkaline earth metal hydroxide e.g. sodium, potassium, lithium, calcium, or magnesium, or an organic base such as an amine, e.g. dibenzylethylenediamine, trimethylamine, piperidine, pyrrolidine, benzylamine, and the like, or a quaternary ammonium hydroxide such as tetramethylammonium hydroxide.

The compounds of formula (I) may be prepared by processes analogous to those described in European Patent Specification No. 0284256. For example, according to one general process (A), a compound of formula (I) may be prepared from an intermediate of formula (II)

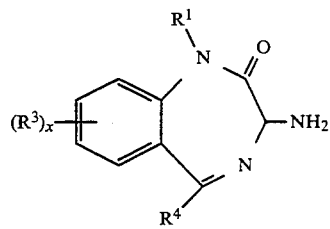

(II)

wherein $R^1$, $R^3$, $R^4$ and x are as defined for formula (I); by reaction with an isocyanate of formula $R^2$—N=C=O wherein $R^2$ is as defined for formula (I).

The reaction is preferably conducted in a suitable organic solvent, such as an ether, for example, tetrahydrofuran, at room temperature.

The isocyanate may be generated in situ from the corresponding amine by treatment with triphosgene.

According to a further general procesS, (B), compounds of formula (I) may be prepared by reacting a compound of formula (IV)

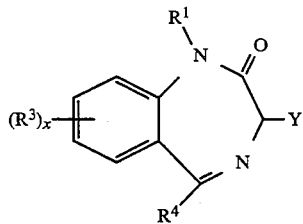

(IV)

wherein $R^1$, $R^3$, $R^4$ and x are as defined for formula (I) and Y represents an activated carbamate, with an amine of formula $R^2NH_2$ in the presence of a base. An "activated carbamate" is a carbamate group which bears a substituent which activates the carbamate function to nucleophilic attack. Suitably Y may represent an appropriately substituted aryl carbamate of formula

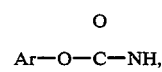

Ar—O—C—NH, for example

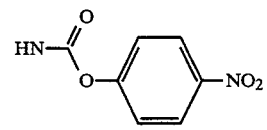

Suitable bases for use in the reaction include tertiary amines, for example, triethylamine.

The reaction is conveniently effected in a suitable organic solvent, for example, dimethylformamide, at ambient or elevated temperature. Preferably the reaction is conducted at approximately 50° C.

Intermediates of formula (II) may be prepared from compounds of formula (VI)

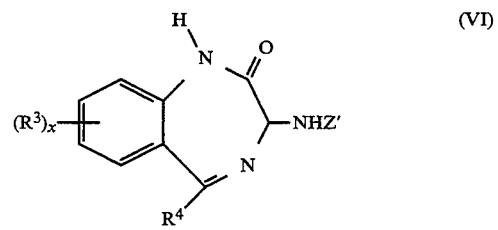

(VI)

wherein $R^3$, $R^4$ and x are as defined for formula (I) and Z' is a protecting group; by reaction with a reagent suitable to introduce the group $R^1$, for example a halide of formula $R^1$Hal where Hal represents halo such as bromo or iodo, in the presence of a base, such as an alkali metal hydride or an alkaline earth metal carbonate, for example sodium hydride or caesium carbonate; or a suitable dialkyl acetal of dimethyl formamide in a suitable organic solvent, e.g. toluene, followed by deprotection.

Compounds of formula (VI) may be prepared from compounds of formula (VII)

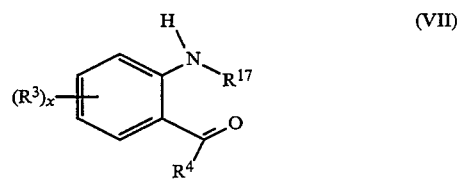

(VII)

wherein $R^3$, $R^4$ and x are as defined for formula (I) and $R^{17}$ is hydrogen, by a reaction sequence comprising:

(i) reaction with a compound of formula (VIII)

(VIII)

wherein Z' is as defined above, in the presence of a base, such as a tertiary amine, for example triethylamine or N-methyl morpholine, and a coupling reagent. Any of the coupling reagents commonly used in peptide synthesis are suitable, for example, 1,3-dicyclohexylcarbodiimide (DCC) or isobutyl chloroformate.

(ii) Treatment with gaseous ammonia, preferably in the presence of a mercury containing catalyst, such as mercury(II) chloride. The reaction is conveniently effected in a suitable organic solvent, such as an ether, for example, tetrahydrofuran.

(iii) Treatment with an organic acid, for example acetic or propionic acid, optionally in the presence of an ammonium salt, for example ammonium acetate.

Compounds of formula (VII) wherein $R^{17}$ is hydrogen may be prepared from corresponding compounds of formula (VII) wherein $R^{17}$ is $COCH_3$ by treatment with a mineral acid, for example hydrochloric acid, or by base hydrolysis, for example, using aqueous sodium hydroxide. The reaction is conveniently affected in refluxing methanol.

Alternatively, compounds of formula (VII) wherein $R^{17}$ is hydrogen may be prepared by reaction of a compound of formula (IX)

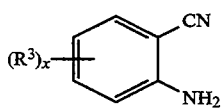
(IX)

wherein $R^3$ and x are as previously defined, with a Grignard reagent of formula $R^4MgHal$ wherein $R^4$ is as previously defined and Hal is halo such as chloro, bromo or iodo.

Compounds of formula (IX) are commercially available or may be prepared from commercially available compounds by conventional methods.

Compounds of formula (VII) wherein $R^{17}$ is $COCH_3$ may be prepared from compounds of formula (X)

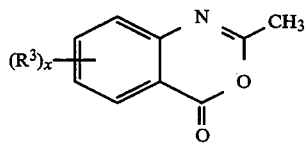
(X)

wherein $R^3$ and x are defined as for formula (I), by reaction with a Grignard reagent of formula $R^4MgHal$ as previously defined.

Compounds of formula (X) may be prepared by known methods, e.g. see D. A. Walsh, Synthesis, 677, (1980).

Intermediates of formula (IV) may be prepared from compounds of formula (II) by reaction with a suitable haloformate of formula

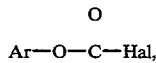

where Hal is as previously defined, preferably chloro, for example

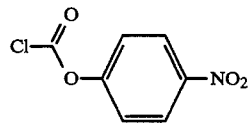

in the presence of a base, such as a tertiary amine, for example, triethylamine.

Amines of formula $R^2NH_2$ are known compounds, or may be prepared from the corresponding nitro compounds of formula $R^2NO_2$ wherein $R^2$ is as defined for formula (I), by reduction.

Suitably the reduction is effected by catalytic hydrogenation, for example, using a noble metal catalyst such as palladium which may be supported, e.g. on carbon.

The reaction is conveniently effected in a suitable organic solvent, such as an alcohol, e.g. ethanol.

Compounds of formula $R^2NO_2$ are commercially available or may be prepared by the procedures described in the accompanying Examples or by alternative procedures which will be readily apparent to one skilled in the art.

Intermediates of formula (II), (IV) and (VI) are novel compounds and form a further aspect of the present invention.

Thus, in a further or alternative aspect, the present invention provides an intermediate of formula (xx)

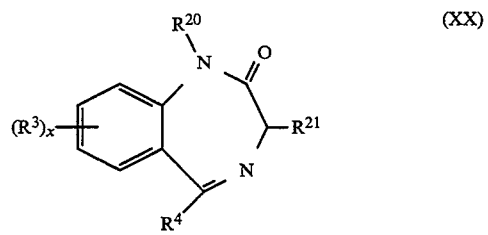
(XX)

wherein $R^3$, $R^4$ and x are as defined for formula (I); $R^{20}$ is hydrogen or $R^1$ as defined for formula (I); and $R^{21}$ is $NH_2$, $NHZ'$ (where $Z'$ is a protecting group), or an activated carbamate.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

Enantiospecific synthesis of compounds of formula (I) may be achieved, for example, by reaction of chiral intermediates of formula (II), which chiral intermediates may be prepared from the corresponding racemate by conventional procedures, for example, as described in J. Org. Chem., 52, 955 and 3232, (1987), with compounds of formula (III).

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene and P. G. M. Wutts, Protective Groups in Organic Synthesis, John Wiley & Sons, 1991. The protecting groups may be removed at a convenient subsequent stage using methods known from the art.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression, such as depression resulting from organic disease, secondary to stress associated with personal loss, or idopathic depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I)o may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occuring in association with iritis, ureitis and trauma.

The present invention therefore provides a compound of formula (I) or a salt or prodrug thereof for use in the preparation of a medicament.

The present invention also provides a compound of formula (I) for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

The present invention also encompasses a pharmaceutical composition comprising a compound of formula (I), or a salt or prodrug thereof and a pharmaceutically acceptable carrier or diluent.

The compounds of formula (I) and their salts and prodrugs, may be administered to animals, preferably to mammals, and most especially to a human subject either alone or, preferably, in combination with pharmaceutically acceptable carriers or diluents, optionally with known adjuvants, such as alum, in a pharmaceutical compostion, according to standard pharmaceutical practice. The compounds can be administered orally, parenterally, including by intravenous, intramuscular, intraperitoneal or subcutaneous administration, or topically.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents,. bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The present invention further provides a process for the preparation of a pharmaceutical composition containing a compound of formula (I), which process comprises bringing a compound of formula (I) into association with a pharmaceutically acceptable carrier or excipient.

When a compound according to formula (I) is used as an antagonist of CCK or gastrin in a human subject, the daily dosage will normally be determined by the prescibing physician with the dosage generally varying according to the age, weight, and response of the individual patient, as well as the severity of the patient's symptoms. However, in most instances, an effective daily dosage will be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 ng/kg to about 1 mg/kg by intraperitoneal administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The following examples are provided to assist in a further understanding of the invention. Particular materials employed, species and conditions are intended to be further illustrative of the invention and not limitative of the scope thereof.

EXAMPLE 1

N-[3(R,S)-5-Cyclohexyl-2,3-dihydro-1-methyl-2-oxo-1H- 1,4-benzodiazepin-3-yl] N'-[3-methylphenyl]urea Step 1: (2-Acetamidophenyl) cyclohexanol methanone Cyclohexylmagnesium bromide (240 ml of a 2M solution in ether, 0.48 mol) in ether (200 ml) was added dropwise to a solution of 2-methyl-4H-3,1-benzoxazin-4-one (100 g, 0.62 mol) in ether (1100 ml) at −10° C. over 2 h. The mixture was stirred at this temperature for 2 h, then at ambient temperature for 30 min. After cooling to −10° C. the suspension was treated with 2M HCl (600 ml), keeping the temperature below 0° C. After stirring for 15 min the layers were separated, and the ethereal layer washed sequentially with water (500 ml), 5% sodium hydroxide solution (2×500 ml) and finally water (2×500 ml). The organic layer was separated, dried (MgSO4), evaporated in vacuo and chromatographed on silica gel using petrol:ethyl acetate (2:1) to give (2-acetamidophenyl) cyclohexyl methanone (28 g, 24%) as a pale yellow solid. mp 66° C. $^1$H NMR (CDCl$_3$, 360 MHz) δ 1.25-1.89 (10H, m), 2.23 (3H, s), 3.33 (1H, m), 7.13 (1H, d of t, J=6 and 1 Hz), 7.53 (1H, d of t, J=6 and 1 Hz), 7.92 (1H, d, J=6 Hz), 8.76 (1H,d, J=6 Hz), 11.73 (1H, brs).

Step 2:(2-Aminophenyl) cyclohexyl methanone

A solution of (2acetamidophenyl) cyclohexyl methanone (0.53 g, 2.16 mmol) in methanol (5 ml) and concentrated hydrochloric acid (15 ml) was heated at 80° C. for 1 h. After this time the solution was cooled to ambient temperature and the solvents removed in vacuo. The residue was dissolved in water (10 ml) and basified with 4N sodium hydroxide solution (20 ml). The mixture was then extracted into ethyl acetate, (4×20 ml) and the organic layers combined and dried (MgSO$_4$). The solvent was evaporated and the residue chromatographed on silica gel using petrol:ethyl acetate (2:1), to afford the amine (0.40 g, 91%) as a white solid. mp 73°-75° C. $^1$H NMR (360 MHz, CDCl$_3$) δ 1.23-2.09 (10H, m), 3.27 (1H, m), 6.29 (2H, brs), 6.64 (2H, m), 7.25 (1H, dt, J=6 and 1 Hz), 7.76 (1H, dd, J=7 and 1 Hz). An alternative procedure could be used for preparation of (2-aminophenyl) cyclohexyl methanone: To a cooled (0° C.) and stirred solution of 2-aminobenzonitrile (59.5 g, 0.5 mol) in anhydrous diethyl ether (210 ml) was added dropwise cyclohexylmagnesium chloride (2M in diethyl ether, 700 ml) at such a rate as to maintain the temperature below 25° C. After a further 18 h stirring at room temperature, the mixture was cooled to −60° C. and treated dropwise (CAUTION! highly exothermic reaction) with 5N hydrochloric acid (600 ml). The mixture was then allowed to warm to room temperature, diluted. with additional 5N hydrochloric acid (500 ml) and the ethereal layer was separated. The acidic aqueous solution was basified to pH 4–5 with solid potassium hydroxide and then extracted with ethyl acetate (3×700 ml). The ethereal and ethyl acetate. solutions were combined, washed with brine (1000 ml), dried (MgSO4) and concentrated under vacuum to give the title compound (97 g, 94%) as a pale yellow solid.

Step 3: 5-Cyclohexyl-1,3-dihydro-3(R,S)-[(benzyloxycarbonyl)amino]-2H-1,4-benzodiazepin-2-one α-(Isopropylthio)-N-(benzyloxycarbonyl)glycine (30 g, 0.11 mol) was dissolved in dichloromethane (1000 ml) and cooled to 0° C. The stirred solution was then treated with N-methyl morpholine (11.5 ml, 0.11 mol) followed by isobutyl chloroformate (13.7 ml, 0.11 mol). The resulting reaction mixture was stirred for a further 15 min at 0° C., then heated to reflux. The refluxing reaction mixture was treated dropwise, over 20 min, with a solution of (2-aminophenyl) cyclohexyl methanone (20.5 g, 0.1 mol) in dichloromethane (140 ml). After addition was complete the reaction was heated at reflux for a further 4 h. The mixture was then washed in succession with 10% citric acid solution (2×500 ml), saturated sodium bicarbonate solution (2×500 ml) and brine (500 ml). The dried (MgSO₄) organic phase was evaporated to afford the crude product as a pale orange solid, which was used without further purification.

The crude (isopropylthio)glycinamide was dissolved in anhydrous tetrahydrofuran (800 ml) and cooled to 0° C. Ammonia gas was bubbled through the stirred solution for 30 min before adding mercuric chloride (33 g, 0.12 mol) in one portion. Ammonia was continually bubbled through the solution for a further 5 hours, then the suspended solids were filtered off. The solvent was evaporated in vacuo to leave an oil, which was used without further purification.

The crude α-aminoglycinamide was dissolved in glacial acetic acid (500 ml) and treated with ammonium acetate (36.2 g, 0.47 mol). The resulting reaction mixture was stirred at room temperature overnight, before removing the solvent in vacuo. The residue was partitioned between ethyl acetate (300 ml) and 1N sodium hydroxide solution (300 ml). The organic phase was separated, dried (MgSO₄) and evaporated. The residue was chromatographed on silica gel, using 2:1 petrol:ethyl acetate as the eluant, to afford 5-cyclohexyl-1,3-dihydro-3(R,S)-[(benzyloxycarbonyl)amino]-2H-1,4-benzodiazepin-2-one (25 g, 64%) as a white solid. mp 164°-166° C. $^1$H NMR (360 MHz, CDCl₃) δ 1.07-2.04 (10H, m), 2.77 (1H, m), 5.12 (3H, m), 6.44 (1H, d, J=8 Hz), 7.08 (1H, d, J=8 Hz), 7.23-7.36 (6H, m), 7.46 (1H, t, J=7 Hz), 7.59 (1H, d, J=8 Hz), 8.60 (1H, brs).

Step 4:
5-Cyclohexyl-1,3-dihydro-1-methyl-3(R,S)-[(benzyloxycarbonyl)amino]-2H-1,4-benzodiazepin-2-one A solution of 5-cyclohexyl-1,3-dihydro-3(R,S)-[(benzyloxycarbonyl)amino]-2H- 1,4-benzodiazepin-2-one (1.1 g, 2.8 mol) in dimethylformamide (13 ml), under an atmosphere of nitrogen, was treated with sodium hydride (117 mg of a 55–60% dispersion in mineral oil, 2.8 mmol) in one portion, at −10° C. After 30 min at −10° C., iodomethane (174 μl, 2.8 mmol) was added in one portion and the solution allowed to reach 0° C. over 1 h. The solvent was then removed in vacuo and the crude residue partitioned between water (100 ml) and dichloromethane (100 ml). The organic phase was separated and the aqueous phase extracted with dichloromethane (2×100 ml). The combined organic layers were washed with brine, dried (MgSO₄) and evaporated. The residue was chromatographed on silica gel, using 1:1 petrol:ethyl acetate as the eluant, to afford the title compound (0.75 g, 66%) as a white solid. mp 205°-207° C. $^1$H NMR (360 MHz, CDCl₃) δ 1.03-2.04 (10H, m), 2.76 (1H, m), 3.36 (3H, s), 5.10 (3H, m), 6.52 (1H, d, J=8 Hz), 7.25-7.55 (9H, m).

Step 5:
N-[3(R,S)-5-Cyclohexyl-2,3-dihydro-1-methyl-2-oxo-1H-1,4-benzodiazepin-3-yl] N'-[3-methylphenyl]urea 5-Cyclohexyl-1,3-dihydro-1-methyl-3(R,S)-[(benzyloxycarbonyl)amino]-2H-1,4-benzodiazepin-2-one (0.34 g, 0.84 mmol) was dissolved in formic acid/methanol (50 ml of a 4.5% (v/v) solution), and added, over 5 min, to a stirred suspension of 10% palladium on carbon (100 mg, 30% (w/w)) in formic acid/methanol (10 ml of a 4.5% (v/v)) solution). After 45 min the catalyst was filtered off and washed sequentially with methanol and acetone. The flitrate was evaporated in vacuo and the residue partitioned between ethyl acetate (100 ml) and 10% sodium carbonate solution (100 ml). The organic phase was separated, dried (Na₂SO₄) and evaporated to give a clear oil, which was used without further purification. A solution of the crude amine (167 mg, 0.61 mmol) in anhydrous tetrahydrofuran (10 ml) was treated with m-tolylisocyanate (79 μl, 0.61 mmol) dropwise over 5 min. After stirring at ambient temperature for 1.5 h the solvent was removed under reduced pressure to leave a white solid. The solid was recrystallised from methanol to give the urea (70 mg, 28%) as a white solid. mp 207°-209° C. $^1$H NMR (360 MHz, CDCl₃) δ 1.07-2.04 (10H, m), 2.29 (3H, s), 2.79 (1H, m), 3.40 (3H, m), 5.40 (1H, d, J=8 Hz), 6.71 (1H, d, J=8 Hz), 6.84 (2H, m), 7.07-7.30 (5H, m), 7.55 (2H, m).

EXAMPLE 2

N-[3(R,S)-5-Cyclohexyl-2,3-dihydro-1-(2-methylpropyl)-2-oxo-1H-1,4-benzodiazepin-3-yl] N'-[3-tetrazol-5-ylphenyl]urea Step 1: 5-(3-Nitrophenyl)tetrazole To a solution of 3-cyanonitrobenzene (20 g, 0.13 mol) in 1-methyl-2-pyrrolidinone (200 ml) was added triethylamine hydrochloride (27.9 g, 0.20 mol) followed by sodium azide (26.4 g, 0.40 mol). The mixture was heated at 160° C. for 1.5 h, then cooled to ambient temperature, poured into ice water (1000 ml) and acidified using 5M HCl. The solid which precipitated from the mixture was filtered, washed with water and dried under vacuum at 50° C. to afford the title tetrazole (22.1 g, 86%) as a beige powder. mp 154°-156 °C. $^1$H NMR (360 MHz, CDCl₃) δ 7.59 (1H, t, J=9 Hz), 8.19 (1H, d, J=8 Hz), 8.36 (1H, d, J=8 Hz), 8.86 (1H, s).

Step 2: 5(3-Aminophenyl)tetrazole, hydrochlorida salt

To a solution of 5-(3-nitrophenyl)tetrazole (22 g, 0.12 mol) in ethanol (500 ml) was added 10% palladium on carbon (1.5 g, 7% (w/w)) in hydrochloric acid (23 ml of a 5M solution). The mixture was hydrogenated at 40 psi for 10 min, then the catalyst filtered off and washed with water. The solvents were evaporated in vacuo and the brown solid azeotroped with toluene (4×100 ml). The resulting solid was triturated with hot ethanol to give 5-(3-aminophenyl)tetrazole hydrochloride (16.3 g, 71%) as a beige powder. mp 203°-205° C. $^1$H NMR (360 MHz, D₂O) δ 7.63 (1H, d, J=9 Hz), 7.75 (1H, t, J=8 Hz), 8.00 (2H, m).

Step 3:
5-Cyclohexyl-1,3-dihydro-1-(2-methylpropyl)-3(R,S)-[(benzyloxycarbonyl)amino]-2H-1,4-benzodiazepin-2-one A solution of 5-cyclohexyl-1,3-dihydro-3(R,S)-[ (benzyloxycarbonyl)amino]-2H-1,4-benzodiazepin-2-one(7.0 g, 18 mmol)in dimethylformamide (84 ml), under an atmosphere of nitrogen, was treated with sodium hydride (0.77 g of a 55–60% dispersion in mineral oil, 18 mmol) in one portion, at −10° C. After 30 min at −10° C., 1-iodo-2-methylpropane (2.3 ml, 19.8 mmol) was added in one portion and the solution allowed to reach 0° C. over 2 h, then stirred at ambient temperature overnight. After this time the solvent was removed under reduced pressure, and the crude residue partitioned between water (500 ml) and dichloromethane (500 ml). The organic phase was separated and the aqueous phase extracted with dichloromethane (2×500 ml). The combined organic layers were washed with brine (500 ml), dried (MgSO$_4$) and evaporated in vacuo. The residue was chromatographed on silica gel, using 2:1 petrol:ethyl acetate as the eluant, to afford the title compound (4.5 g, 56%) as a white solid. mp 148°–150° C. $^1$H NMR (360 MHz, CDCl$_3$) δ 0.73 (3H, d, J=7 Hz), 0.79 (3H, d, J=7 Hz), 1.14–2.09 (11H, m), 2.80 (1H, m), 3.42 (1H, dd, J=14 and 5 Hz), 4.27 (1H, dd, J=14 and 9 Hz), 5.10 (3H, m), 6.55 (1H, d, J=8 Hz), 7.23–7.34 (8H, m), 7.45 (1H, t, J=8 Hz), 7.56 (1H, d, J=8 Hz).

Step 4:
N-[3(R,S)-5-Cyclohexyl-2,3-dihydro-1-(2-methylpropy)-2-oxo-1H-1,4-benzodiazepin-3-yl] N′-[3-tetrazol-5-ylphenyl]urea 5-Cyclohexyl-1,3-dihydro-1-(2-methylpropyl)-3(R,S)-[(benzyloxycarbonyl)amino]-2H-1,4-benzodiazepin-2-one (1.0 g, 2.23 mmol) was dissolved in formic acid/methanol (130 ml of a 4.5% (v/v) solution), and added over 5 min to a stirred suspension of 10% palladium on carbon (0.36 g, 36% (w/w)) in formic acid/methanol (27 ml of a 4.5% (v/v) solution). After 4 h at room temperature the catalyst was filtered off and washed sequentially with methanol and acetone. The flitrate was evaporated in vacuo and the solid residue partitioned between ethyl acetate (500 ml) and 10% sodium carbonate solution (500 ml). The organic phase was dried (Na$_2$SO$_4$) and evaporated to give a clear oil, which was used without further purification. To a suspension of 5-(3-aminophenyl)tetrazole hydrochloride (0.29 g, 1.45 mmol) in tetrahydrofuran (10 ml) was added triethylamine (0.4 ml, 2.9 mmol). The mixture was cooled in an ice bath and triphosgene (0.14 g, 0.48 mmol) added, followed by triethylamine (0.3 ml, 2.2 mmol). The ice bath was removed and the mixture stirred at room temperature for 30 min. A solution of the aminobenzodiazepine (0.35 g, 1.11 mmol), from the above procedure, in tetrahydrofuran (15 ml) was added dropwise to the mixture. The reaction mixture was stirred at room temperature for 2 h, then diluted with ethyl acetate (30 ml) followed by 20% aqueous acetic acid (30 ml). After stirring for a further 15 min a white precipitate was filtered off and washed with ethyl acetate. The solid was suspended in methanol (20 ml), heated to 50° C., then filtered hot to afford N-[3(R,S)-5-cyclohexyl-2,3-dihydro-1-(2-methylpropyl )-2-oxo-1H-1,4-benzodiazepin-3-yl] N′-[3-tetrazol-5-ylphenyl]urea (280 mg, 39%) as a white solid. mp 188°–190° C. $^1$H NMR (360 MHz, D$_6$-DMSO) δ 0.65 (3H, d, J=7 Hz), 0.76 (3H, d, J=7 Hz), 0.99–1.96 (11H, m), 2.97 (1H, m), 3.62 (1H, dd, J=14 and 5 Hz), 4.15 (1H, dd, J=14 and 9 Hz), 5.05 (1H, m), 7.36–7.69 (7H, m), 7.78 (1H, d, J=8 Hz), 8.15 (1H, s), 9.23 (1H, s).

EXAMPLE 3

N-[3(R,S)-5-Cyclopentyl-2,3-dihydro-1-(2-methylpropyl)-2-oxo-1H-1,4-benzodiazepin-3-yl] N′-[3-tetrazol-5-ylphenyl]urea The title compound was prepared using the same procedure as that described for Example 2, replacing cyclohexyl with cyclopentyl. The product was purified by separating the organic layer which was dried (MgSO$_4$) and evaporated in vacuo. The resulting solid was subjected to preparative thin layer chromatography, eluting with chloroform-methanol-acetic acid (85:10:5). This afforded the title compound (67 mg) as a colourless solid. mp 185°–187° C. $^1$H NMR (360 MHz, D$_6$-DMSO) δ 0.62 (3H, d, J=7 Hz), 0.75 (3H, d, J=7 Hz), 1.26 (1H, m), 1.51–1.99 (8H, m), 3.50 (1H, m), 3.61 (1H, dd, J=14 and 5 Hz), 4.16 (1H, dd, J=14 and 10 Hz), 5.10 (1H, s), 7.38–7.65 (7H, m), 7.78 (1H, d, J=8 Hz), 8.16 (1H, s), 9.22 (1H, s).

EXAMPLE 4

N-[3(R,S)-5-Cyclohexyl-2,3-dihydro-1-methyl-2-oxo-1H-1,4-benzodiazepin-3-yl] N′-[3-tetrazol-5-ylphenyl]urea 5-Cyclohexyl-1,3-dihydro-1-methyl-3(R,S)-[(benzyloxycarbonyl)amino]-2H-1,4-benzodiazepin-2-one (0.61 g, 1.5 mmol) was dissolved in formic acid/methanol (80 ml of a 4.5% (v/v) solution, and added, over 5 min, to a stirred suspension of 10% palladium on carbon (180 mg, 30% (w/w)) in formic acid/methanol (18 ml of a 4.5% (v/v) solution). After 1 h the catalyst was filtered off and washed sequentially with methanol and acetone. The filtrate was evaporated in vacuo and the residue partitioned between ethyl acetate (100 ml) and 10% sodium carbonate solution (100 ml). The organic phase was separated, dried (Na$_2$SO$_4$) and evaporated to give a clear oil, which was used without further purification.

To a suspension of 5-(3-aminophenyl)tetrazole hydrochloride (0.39 g, 1.95 mmol) in tetrahydrofuran (14 ml) was added triethylamine (0.54 ml, 3.9 mmol). The mixture was cooled in an ice bath and triphosgene (0.19 g, 0.65 mmol) added, followed by triethylamine (0.27 ml, 1.95 mmol). The ice bath was removed and the mixture stirred at room temperature for 30 min. A solution of the crude aminobenzodiazepine, from the above procedure, in tetrahydrofuran (15 ml) was added dropwise to the mixture. The reaction mixture was stirred at room temperature for 2 h, then diluted with ethyl acetate (30 ml) followed by 20% aqueous acetic add (30 ml). The two phases were separated and the organic phase dried (MgSO$_4$) and evaporated in vacuo. The crude residue was triturated in hot methanol (3×20 ml) to afford the title compound (140 mg, 20%) as a colourless solid. mp 203°–205° C. $^1$H NMR (360 MHz, D$_6$-DMSO) δ 0.92 (1H, m), 1.15–1.59 (7H, m), 1.75 (1H, m), 1.91 (1H, m), 2.93 (1H, m), 3.33 (3H, s), 5.09 (1H, d, J=5 Hz), 7.34–7.66 (7H, m), 7.75 (1H, d, J=8 Hz), 8.11 (1H, s), 9.22 (1H, s).

EXAMPLE 5

N-[3(R,S)-5-Cyclopenentyl-2,3-dihydro-1-ethyl-2-oxo-1H-1,4-benzodiazepin-3-yl]N′-[3-tetrazol-5-ylphenyl]urea Step 1: (2-Acetamidophenyl) cyclopentyl methanone Replacement of cyclohexylmagnesium bromide in Example 1, Step 1, with cyclopentylmagnesium chloride afforded the title compound as a yellow oil in 39% yield. $^1$H NMR (CDCl$_3$ 250 MHz) δ 1.6–1.8 (4H, m), 1.8–2.0 (4H, m), 2.24 (3H, s), 3.75 (1H, p, J=8Hz), 7.10 (1H, m), 7.55 (1H, m), 8.0 (1H, m), 8.7 (1H, d, J=8Hz), 11.8 (1H, s).

Step 2: (2-Aminophenyl) cyclopentyl methanone

A solution of (2-acetamidophenyl) cyclopentyl methanone (4.0 g, 0.017 mol) in methanolic potassium hydroxide solution (2M, 300 ml) was heated at reflux for 12 h. After this time the solvent was removed and the residue partitioned between ethyl acetate (100 ml) and water (50 ml). The organic phase was separated, dried (MgSO$_4$) and evaporated to give a yellow oil, which was purified by column chromatography on silica gel using 3:1 petrol:ethyl acetate as eluant, to afford the product (2.5 g, 76%) as an oil. Tlc (silica, EtOAc:Pet ether (60°–80°) 1:2), Rf, 0.5. $^1$H NMR (250 MHz, CDCl$_3$) δ 1.53–1.80 (4H, m), 1.80–2.0 (4H, m), 3.70 (1H, p, J=8 Hz), 6.0 (2H, brs), 6.70 (2H, m), 7.15–7.3 (1H, m), 7.8 (1H, m).

Step 3:
5-Cyclopentyl-1,3-dihydro-3(R,S)-[(benzyloxycarbonyl)amino]-2H-1,4-benzodiazepin-2-one Replacement of (2-aminophenyl) cyclohexyl methanone in Example 1, Step 3, with (2-aminophenyl) cyclopentyl methanone afforded the title compound as a colourless solid in 71% yield. Tlc (silica, EtOAc:Pet ether (60°–80°) 1:2), Rf, 0.3. $^1$H NMR (250 MHz, D$_6$-DMSO) δ 1.1 (1H, m), 1.40–1.75 (5H, m), 1.75–1.95 (1H, m), 2.1 (1H, m), 3.45 (1H, p, J=8 Hz), 4.9 (1H, m), 5.05 (2H, s), 7.12–7.42 (6H, m), 8.15 (1H, d, J=8 Hz), 10.6 (1H, brs).

Step 4:
5-Cyclopentyl-1,3-dihydro-1-ethyl-3(R,S)[(benzyloxycarbonyl)amino]-2H-1,4-benzodiazenin-2-one Sodium hydride (60% dispersion, 0.106 g, 2.65 mmol) was added portionwise to a solution of 5-cyclopentyl-1,3-dihydro-3(R,S)-[(benzyloxycarbonyl)amino]-2H-1,4-benzodiazepin-2-one ( 1 g, 2.65 mmol) in anhydrous dimethylformamide (30 ml) cooled in ice, and the resulting mixture stirred for 1 h. Ethyl iodide (0.23 ml, 2.8 mmol) was then added and the mixture stirred at room temperature for 16 h. The solvent was then evaporated and the residue partitioned between dichloromethane (80 ml) and water (20 ml). The organic phase was separated, dried (Na$_2$SO$_4$) and evaporated. The residue was purified by column chromatography on silica gel using 2:1 petrol:ethyl acetate as eluant to afford 0.78 g (73% yield) of product as a colourless powder. mp 133°–136° C. Tlc (silica, EtOAc:Pet ether (bp 60°–80°) 1:2), Rf, 0.5. $^1$H NMR (250 MHz, D$_6$-DMSO) δ 0.9 (3H, t, J=8 Hz), 1.1 (1H, m), 1.4–1.9 (6H, m), 2.1 (1H, m), 3.5 (1H, p, J=7 Hz), 3.7 (1H, m), 4.15–4.3 (1H, m), 4.95 (1H, d, J=8 Hz), 5.02 (2H, s), 7.2–7.8 (8H, m), 8.15 (1H, d, J=8 Hz).

Step 5:
3(R,S)-Amino-5-cyclopentyl-1,3-dihydro-1-ethyl-2H-1,4-benzodiazepin-2-one 5-Cyclopentyl-1,3-dihydro-1-ethyl-3(R,S)[(benzyloxycarbonyl)amino]-2H-1,4-benzodiazepin-2-one (0.5 g, 1.23 mmol) was dissolved in formic acid/methanol (50 ml of a 4.5% (v/v) solution), and added, over 5 min, to a stirred suspension of 10% palladium on carbon (200 mg, 40% (w/w)) in formic acid/methanol (10 ml). After 10 min the catalyst was removed by filtration, washed with methanol and acetone and the flitrate concentrated. The residue was partitioned between ethyl acetate (100 ml) and 10% sodium carbonate solution (100 ml). The organic phase was separated, dried (Na$_2$SO$_4$) and evaporated to give a clear oil which was used without further purification.

Step 6:N-[3(R,S)-5-Cyclopentyl-2,3-dihydro-1-ethyl-2-oxo-1H-1,4,-benzodiazepin-3-yl]N'-[3-tetrazol-5-ylphenyl]urea Triethylamine (0.62 ml, 4.5 mmol) was added to a suspension of 5-(3-aminophenyl)tetrazole hydrochloride (292 mg, 1.5 mmol) in tetrahydrofuran (10 ml) stirring at room temperature. The mixture was cooled in ice, and triphosgene (0.14 g, 0.48 mol) added in one portion. The ice bath was removed and the mixture stirred at room temperature for 30 min. A solution of crude 3(R,S)-amino-5-cyclopentyl-1,3-dihydro-1-ethyl-2H-1,4-benzodiazepin-2-one (307 mg, 1.13 mmol)in tetrahydrofuran (30 ml) was added dropwise and stirring continued for 30 min. The reaction mixture was then diluted with ethyl acetate (150 ml) and aqueous acetic acid (20% aqueous solution 80 ml), the organic phase separated, dried (MgSO$_4$) and evaporated. The residue was purified by column chromatography on silica gel using dichloromethane:methanol:acetic acid 94:6:0.6 as eluant, to afford a gummy solid which was triturated with methanol to afford 95 mg (16% yield) of the title compound as a colourless powder. mp 210° C. (dec.). $^1$H NMR (360 MHz, D$_6$-DMSO) δ 0.92 (3H, t, J=7 Hz), 1.05 (1H, m), 1.40–1.86 (6H, m), 2.10 (1H, m), 3.55 (1H, m), 3.62–3.80 (1H, m), 4.25 (1H, m), 5.10 (1H, m), 7.32–7.70 (7H, m), 7.79 (1H, d, J=7 Hz), 8.11 (1H, s), 9.22 (1H, s).

EXAMPLE 6

N-[3(R,S)-5-Cyclopentyl-2,3-dihydro-1-propyl-2-oxo-1H-1,4-benzodiazepin-3-yl]N'-[3-tetrazol-5-ylphenyl]urea Carrying out Steps 1–6 of Example 5 replacing ethyl iodide, in Step 4 with n-propyl iodide, afforded the title compound as a colourless powder. mp 220° C. (dec.). $^1$H NMR (360 MHz, D$_6$-DMSO) δ 0.73 (3H, t, J=7 Hz), 1.08–1.44 (3H, m), 1.46–1.78 (5H, m), 1.79–1.86 (1H, m), 2.05 (1H, m,), 3.45–3.58 (1H, m), 3.63–3.74 (1H, m), 4.25 (1H, m), 5.08 (1H, m), 7.34–7.51 (4H, m), 7.57 (1H, m), 7.62 (2H, m), 7.80 (1H, d, J=8 Hz), 8.17 (1H, s), 9.27 (1H, s).

EXAMPLE 7

Chiral separation of N-[3(R,S)-5-Cyclohexyl-2,3-dihydro-1-methvl-2-oxo-1H-1,4-benzodiazepin-3-yl]N'-[3-methylphenyl]urea N-[3(R,S)-5-Cyclohexyl-2,3-dihydro-1-methyl-2-oxo-1H-1,4-benzodiazepin-3-yl]N'-[3-methylphenyl]urea (15 mg, 0.04 mmol) was dissolved in tetrahydrofuran (10 mg/ml). 300 μl of solution was injected onto a dinitrobenzoylphenyl glycine column (250×8.0 mm i.d., 5 μM) per run, using 15% ethanol in hexane as the mobile phase. Using a flow rate of 4 ml/min and U.V. detection at 280 mm, the two enantiomers were efficiently separated. The fractions containing each separate enantiomer were combined and evaporated in vacuo.
Peak A (7 mg):
Retention time 9.8 min. mp=184°–186° C.
Purity: A:B =96:4
Peak B (7 mg):
Retention time 13.3 min. mp=186°–188° C.
Purity: B:A =98:2.

EXAMPLE 8

N-[3(R,S)-5-CyClopentyl-2,3-dihydro-1-methyl-2-oxo-1H-1,4-benzodiazepin-3-yl]N'-[3-tetrazol-5-ylphenyl-]urea The title compound was prepared using the same procedure as that described for Example 5, replacing ethyl iodide in Step 4 with methyl iodide. The product was purified using preparative thin layer chromatography, eluting with chloroform-methanolacetic acid (96:6:0.6). This afforded the desired urea (30 mg) as a colourless solid. mp 193°–195° C. $^1$H NMR (360 MHz, D$_6$-DMSO+TFA) δ 1.15 (1H, m), 1.60 (5H, m), 1.86 (1H, m), 2.05 (1H, m), 3.36 (3H, s), 3.52 (1H, m), 5.16 (1H, s), 7.39–7.69 (7H, m), 7.81 (1H, d, J=7 Hz), 8.21 (1H, s), 9.31 (1H, s).

EXAMPLE 9

N-[3(R,S)-5-Cyclohexyl-2,3-dihydro-1-methyl-2-oxo-1H-1,4-benzodiazepin-3-yl]N'-[3-ethynylphenyl]urea 5-Cyclohexyl-1,3-dihydro-1-methyl-3(R,S)-[(benzyloxycarbonyl )amino]-2H-1,4-benzodiazepin-2-one (0.71 g, 1.75 mmol) was dissolved in formic acid/methanol (104 ml of a 4.5% (v/v) solution) and added, over 5 min to a stirred suspension of 10% palladium on carbon (200 mg, 30% (w/w)) in formic acid/methanol (20 ml of a 4.5% (v/v) solution). After 2 h the catalyst was filtered off and washed sequentially with methanol and acetone. The filtrate was evaporated in vacuo and the residue partitioned between ethyl acetate (200 ml) and 10% sodium carbonate solution (200 ml). The organic phase was separated, dried (Na$_2$SO$_4$) and evaporated to give a clear oil, which was used without further purification.

A solution of 3-ethynylaminobenzene (0.27 g, 2.3 mmol) in anhydrous tetrahydrofuran (5 ml), cooled in an ice bath, was treated with triphosgene (0.22 g, 0.75 mmol), followed by triethylamine (0.32 ml, 2.3 mmol). The ice bath was removed and the mixture stirred at room temperature for 30 min. A solution of the aminobenzodiazepine, from the above procedure, in tetrahydrofuran (7 ml) was added dropwise to the mixture. The reaction mixture was stirred at room temperature for 2 h, then diluted with ethyl acetate (30 ml) followed by 20% aqueous acetic acid (30 ml). The organic layer was separated, dried (MgSO$_4$) and evaporated in vacuo. The residue was chromatographed on silica gel, using a gradient elution (2:1 petrol: ethyl acetate followed by methanol). The title compound (0.27 g, 37%) was collected as a white solid, after trituration with diethyl ether. mp 198°–200° C. $^1$H NMR (360 MHz, D$_6$-DMSO) δ 0.90 (1H, m), 1.11–1.59 (7H, m), 1.76 (1H, m), 1.89 (1H, m), 2.93 (1H, m), 3.31 (3H, s), 4.09 (1H, s), 5.05 (1H, d, J=8 Hz), 7.00 (1H, d, J=7 Hz), 7.20–7.39 (4H, m), 7.54 (2H, m), 7.63 (1H, dd, J=8 and 8 Hz), 7.74 (1H, d, J=8 Hz), 9.13 (1H, s).

EXAMPLE 10

N-[3(R,S)-5-Cyclohexyl-2,3-dihydro-1-methyl-2-oxo-1H-1,4-benzodiazepin-3-yl]N'-[3-carboxyphenyl]urea Sodium periodate (274 mg, 1.3 mmol) in water (1.5 ml) was added to a vigorously stirred solution of N-[3(R,S)-5-cyclohexyl-2,3-dihydro-1-methyl-2-oxo-1H-1,4-benzodiazepin-3-yl]N'-[3-ethynyrphenyl]urea (166 mg, 0.4 mmol) in acetonitrile (1.8 ml) and carbon tetrachloride (1.8 ml). Ruthenium trichloride trihydrate (5 mg) was then added in one portion, and the mixture stirred at room temperature for 3 h. The mixture was then filtered through celite, washed with acetonitrile followed by methanol, and the tiltrate evaporated in vacuo. The residue was purified by preparative thin layer chromatography, eluting with chloroform-methanol-acetic acid (85:10:5) to give the title compound (55 mg, 32%) as a pink solid. mp 199°–201° C. $^1$H NMR (360 MHz, D$_6$-DMSO) δ 1.10–1.78 (8H, m), 1.80 (1H, m), 1.98 (1H, m), 3.24 (1H, m) 3.53 (3H, m), 5.22 (1H, s), 7.35–7.71 (8H, m), 8.07 (1H, s), 9.36 (1H, m).

EXAMPLE 11

N-[3(R,S)-5-Cyclohexyl-2,3-dihydro-1-methyl-2-oxo-1H-1,4-benzodiazepin-3-yl]N'-[3-(isopropylcarbonylaminosulphonyl)phenyl]urea Step 1: 1-(Isopropylcarbonylaminosulphonyl)-3-nitrobenzene To a mixture of isobutyric acid (4.6 ml, 0.05 mol), 3-nitrophenyl sulphonamide (10.1 g, 0.05 mol) and 4-dimethylaminopyridine (6.1 g, 0.05 mol) in anhydrous dichloromethane (400 ml) under an atmosphere of nitrogen was added 1-[3-(dimethylamino)propyl]-3-ethyl carbodiimide hydrochloride (9.6 g 0.05 mol). The mixture was stirred at ambient temperature for 20 h. The mixture was extracted with 1M NaOH and tile separated aqueous phase was acidified using 5M HCl. The solid which precipitated was collected by filtration, washed with water and dried under vacuum to afford the title compound (8.16 g, 60%) as a colourless powder. mp 136°–138° C. $^1$H NMR (360 MHz, D$_6$-DMSO) δ 0.95 (6H, d, J=6.8 Hz), 2.48 (1H, septet, J=6.8 Hz), 7.95 (1H, dd, J=8.1 and 8.1 Hz), 8.33 (1H, dd, J=8.0 and 1.4 Hz), 8.54 (1H, dd, J=8.0, 1.4 Hz), 8.60 (1H, dd, J=1.4 and 1.4 Hz), 12.38 (1H, brs).

Step 2: 1-(Isopropyl carbonylaminosulphonyl)-3-aminobenzene

To a suspension of 1-(isopropylcarbonylaminosulphonyl)-3-nitrobenzene (5 g, 18.4 mmol) in ethanol (100 ml) was added 10% palladium on carbon (0.5 g, 10% (w/w)) in water (5 ml). The mixture was hydrogenated at 40 psi for 10 min then the catalyst was filtered off and washed with ethanol. The solvents were evaporated in vacuo to give the title compound (3.4 g, 76%) as a yellow solid. mp 110°–112° C. $^1$H NMR (360 MHz, D$_6$-DMSO) δ 0.95 (6H, d, J=6.9 Hz), 2.45 (1H, septet, J=6.9 Hz), 5.63 (2H, br s), 6.79 (1H, ddd, J=8.0, 2.3 and 0.8 Hz), 6.96 (1H, ddd, J=7.6, 1.7 and 0.8 Hz), 7.09 (1H, dd, J=2.0 and 2.0 Hz), 7.20 (1H, dd, J=7.9 and 7.9 Hz), 11.79 (1H, brs).

Step 3: 5-Cyclohexyl-1,3-dihydro-1-methyl-3(R,S)-[(4-nitrophenyloxycarbonyl)amino]-2H-1,4-benzodiazepin-2-one 5-Cyclohexyl-1,3-dihydro-1-methyl-3(R,S) [(benzyloxycarbonyl)amino]-2H-1,4-benzodiazepin-2-one (1.5 g, 3.7 mmol) was dissolved in formic acid/methanol (200 ml of a 4.5% (v/v) solution), and added, over 5 min, to a stirred suspension of 10% palladium on carbon (500 mg, 33% (w/w)) in formic acid/methanol (20 ml of a 4.5% (v/v) solution). After 1 h the catalyst was filtered off and washed sequentially with methanol and acetone. The flitrate was evaporated in vacuo and the residue partitioned between ethyl acetate (25 ml) and 10% sodium carbonate solution (25 ml). The organic phase was separated and the aqueous phase extracted with ethyl acetate (5×25 ml). The combined organic phases were dried (Na$_2$SO$_4$) and evaporated in vacuo to give a clear oil which was used without further purification.

A solution of the crude amine (1g, 3.7 mmol) in anhydrous tetrahydrofuran (20 ml) under an atmosphere of nitrogen at 0° C. was treated with triethylamine (0.51 ml, 3.7 mmol), followed by a solution of 4-nitrophenyl chloroformate (0.75 g, 3.7 mmol) in anhydrous tetrahydrofuran (10 ml) dropwise. After stirring at ambient temperature for 20 min, the solid which precipitated from the mixture was filtered and the flitrate was evaporated in vacuo to leave a pink solid. The solid was triturated with diethyl ether to give the title compound (1.2 g, 75%) as a colourless solid. mp 165°–168° C. $^1$H NMR (360 MHz, CDCl$_3$) δ 1.05 (1H, m), 1.18–1.42 (3H, m), 1.55 (1H, m), 1.65 (3H, m), 1.87 (1H, m), 2.05 (1H, m), 2.80 (1H, m), 3.43 (3H, s), 5.18( 1H, d, J=8.3 Hz), 6.90 (1H, d, J=8.2 Hz), 7.30 (4H, m), 7.57 (2H,m), 8.23 (2H, d, J=7.1 Hz).

Step 4:
N-[3(R,S),Cyclohexyl-2,3-dihydro-1-methyl-2-oxo-1H-1,4-benzodiazepin-3-yl]N'-[3-(isopropylcarbonylaminosulphonyl) phenylk]urea A solution of 5-cyclohexyl-1,3-dihydro-1-methyl-3(R,S)-[(4-nitrophenyloxycarbonyl)amino]-2H-1,4-benzodiazepin-2-one (0.3 g, 0.69 mmol) in anhydrous dimethylformamide (5 ml), under an atmosphere of nitrogen, at ambient temperature was treated with triethylamine (96 μl 0.69 mmol). After stirring at ambient temperature for 5 min, a solution of 1-(isopropylcarbonylaminosulphonyl)-3-aminobenzene ( 175 mg, 0.72 mmol) in anhydrous dimethylformamide (5 ml) was added dropwise. The bright yellow solution was heated at 50° C. for 6 h. The solution was cooled and the solvent evaporated in vacuo. The residue was partitioned between ethyl acetate (20 ml) and 20% aqueous acetic acid (5 ml). The organic phase was separated and the aqueous phase extracted with ethyl acetate (2×20 ml). The combined organic layers were dried (Na$_2$SO$_4$) and evaporated in vacuo. The residue was triturated with diethyl ether to give a cream solid. This was recrystallised from hot methanol to give the title compound (76 mg, 20%) as a colourless solid. mp 180° C. (dec.). $^1$H NMR (360 MHz, D$_6$-DMSO) δ 0.92 (6H, d, J=6.8 Hz), 1.10–166 (8H,m), 1.78 (1H, m), 1.92 (1H, m), 2.43 (1H, septet, J=6.8 Hz), 2.92 (1H, m), 3.38 (3H, s), 5.06 (1H, d, J=8.2 Hz), 7.37 (6H, m), 7.64 (1H, dd, J=7.7 and 7.7 Hz), 7.75 (1H, d, J=7.9 Hz), 8.06 (1H, s), 9.40 (1H, s), 11.94 (1H, brs).

EXAMPLE 12

N-[3(R,S)-5-Cyclohexyl-2,3-dihydro-1-methyl-2-oxo-1H-1,4-benzodiazepin-3-yl]N'-[3-(isopropylsulphonylaminocarbonyl)phenyl]urea

Step 1: Isopropylsulphonamide

Ammonia gas was bubbled through a stirred solution of isopropylsulphonyl chloride (3.9 ml, 35 mmol) in anhydrous tetrahydrofuran (100 ml), cooled to 0° C., for 30 min. After allowing to warm to ambient temperature, the mixture was filtered and the flitrate evaporated in vacuo, to leave a white solid. This was partitioned between ethyl acetate (50 ml) and water (50 ml). The organic phase was separated and the aqueous phase extracted with ethyl acetate (3×50 ml). The combined organic layers were dried (Na$_2$SO$_4$) and evaporated in vacuo to afford the title compound (3.5 g, 81%) as a colourless solid. mp 51°–53° C. $^1$H NMR (360 m Hz, CDCl$_3$) δ 1.92 (6H, d, J=6.7 Hz), 3.22 (1H, septet, J=6.7 Hz), 4.61 (2H, brs).

Step 2:
1-(Isopropylsuphonylaminocarbonyl)-3-nitrobenzene

The title compound was prepared in the same way as that described in Example 11, Step 1, using isopropylsulphonamide (1.7 g, 13.8 mmol), 3-nitrobenzoic acid (2.31 g, 13.8 mmol), 4-dimethylaminopyridine (1.69 g, 13.8 mmol), 1-[3-(dimethylamino)propyl]-3-ethyl carbodiimide hydrochloride (2.65 g, 13.8 mmol) and anhydrous dichloromethane (100 ml). The compound (2.74 g, 75%) was afforded as a colourless solid. mp 175°–177° C. $^1$H NMR (360 MHz, D$_6$-DMSO) δ 1.34 (6H, d, J=6.9 Hz), 3.83 (1H, septet, J=6.9 Hz), 7.83 (1H, dd, J=8.0 and 8.0 Hz), 8.35 (1H, d, J=8.0 Hz), 8.48 (1H, d, J=8.0 Hz), 8.78 (1H, s), 12.40 (1H, brs).

Step 3:1-(Isopropylsuphonylaminocarbonyl)-3-aminobenzene

In the same way as that described in Example 11, Step 2, using 1-(isopropylsuphonylaminocarbonyl)-3-nitrobenzene ( 2.5 g, 9.2 mmol), 10% palladium on carbon (0.25 g, 10% (w/w))in water (2 ml) and ethanol (50 ml), the title compound was afforded as a yellow solid. This was recrystallised from ethanol to give a pale yellow crystalline solid (1.7 g, 76%). mp 190°–193° C. $^1$H NMR (360 MHz, D$_6$-DMSO) δ 1.30 (6H, d, J=6.9 Hz), 3.79 (1H, septet, J=6.9 Hz), 5.36 (2H, brs), 6.79 (1H, dd, J=7.9 and 1.2 Hz), 7.05 (2H, m);7.13 (1H, dd, J=7.8 and 7.8 Hz).

Step 4:
N-[3(R,S)-5-Cyclohexyl-2,3-dihydro-1-methyl-2-oxo-1H-1,4-benzodiazepin-3-yl] N'-[3(isopropylsulphonylaminocarbonyl)phenyl]urea The title compound was prepared in the same way as that described in Example 11, Step 4, using 5-cyclohexyl-1,3-dihydro- 1-methyl-3(R,S)-[(4-nitrophenyloxycarbonyl)amino]-2H-1,4-benzodiazepin-2-one (0.3 g, 0.69 mmol), triethylamine (96 μl, 0.69 mmol), dimethylformamide (6 ml) and 1-(isopropylsulphonylaminocarbonyl)-3-aminobenzene (0.175 mg, 0.72 mmol). After recrystallisation from ethanol the title compound (0.24 g, 65%) was afforded as a colourless solid. mp 165° C. (dec.). $^1$H NMR (360 MHz, D$_6$-DMSO) δ 0.87–0.98 (1H, m), 1.10–1.64 (7H, m), 1.30 (6H, d, J=6.9 Hz), 1.79 (1H, m), 1.88–1.96 (1H, m), 2.95 (1H, m), 3.33 (3H, s), 3.79 (1H, septet, J=6.9 Hz), 5.07 (1H, d, J=8.2 Hz), 7.37 (3H, m), 7.46 (1H, d, J=7.8 Hz), 7.55 (2H, m), 7.64 (1H, dd, J=7.1 and 7.1 Hz), 7.75 (1H, d, J=7.9 Hz), 7.92 (1H,s), 9.22 (1H,s), 11.93 (1H, brs).

EXAMPLE 13

N-[3(R,S)-5-Cyclohexyl-2,3-dihydro-1-methyl-2-oxo-1H-1,4-benzodiazepin-3-yl] N'-[3-(phenylcarbonylaminosulphonyl) phenyl]urea

Step 1:
1-(Phenylcarbonylaminosulphonyl)-3-nitrobenzene

The title compound was prepared in the some way as that described in Example 11, Step 1, using 3-nitrobenzenesulphonamide (10.1 g, 50 mml), benzoic acid (6.1 g, 50 mmol), 4-dimethylaminopyridine (6.1 g, 50 mmol), 1-[3-(dimethylamino)propyl]-3-ethyl carbodiimide hydrochloride (9.59 g, 50 mmol) and anhydrous dichloromethane (400ml). The title compound (13.1 g, 86%) was afforded as a colourless solid. mp 181°–183° C. $^1$H NMR (360 MHz, D$_6$-DMSO) δ 7.49 (2H, m), 7.61–7.66 (1H, m), 7.86–7.89 (2H, m), 7.96 (1H, dd, J=8.0 and 8.0 Hz), 8.43 (1H, m), 8.56 (1H, m), 8.71 (1H, m).

Step 2:
1-(Phenylcarbonylaminosulphonyl)-3-aminobenzene

In the same way as that described in Example 11, Step 2, using 1-(phenylcarbonylaminosulphonyl)-3-nitrobenzene (5.3 g, 17.3 mmol), 10% palladium on carbon (0.5 g, 9% (w/w)) in water (3 ml) and ethanol (100 ml), the title compound (4.3 g, 90%) was afforded as a yellow solid. mp 160°-162° C. $^1$H NMR (360 MHz, D$_6$-DMSO) δ 6.81 (1H, m), 7.07 (1H, m), 7.22 (2H, m), 7.48 (2H, m), 7.60 (1H, dd, J=7.4 and 7.4 Hz), 7.87 (2H, m).

Step 3:
N-[3(R,S)-5-Cyclohexyl-2,3-dihydro-1-methyl-2-oxo-1H-1,4-benzodiazepin-3-yl]N'-[3-phenylcarbonylaminosulphonyl) phenyl]urea The title compound was prepared in the same way as that described in Example 11, Step 4, using 5-cyclohexyl-1,3-dihydro-1-methyl-3(R,S)-[(4-nitrophenyloxycarbonyl)amino]-2H-1,4-benzodiaZepin-2-one (0.3 g, 0.69 mmol), triethylamine (96 µl, 0.69 mmol), dimethylformamide (6 ml) and 1-(phenylcarbonylaminosulphonyl)-3-aminobenzene (0.21 g, 0.76 mmol). After trituration with methanol, the compound (0.16 g, 41%) was afforded as a colourless solid. mp 200°-202° C. $^1$H NMR (360 MHz, D$_6$-DMSO) δ 0.91 (1H, m), 1.10-1.40 (3H, m), 1.42-1.69 (4H, m), 1.78 (1H, m), 1.92 (1H, m), 2.94 (1H, m), 3.32 (3H, s), 5.06 (1H, d, J=8.1 Hz), 7.36 (2H, m), 7.45-7.56 (6H, m), 7.62 (2H, m); 7.75 (1H, d, J=7.9 Hz), 7.84 (2H, m), 8.17 (1H, s), 9.42 (1H, s), 12.50 (1H, brs).

EXAMPLE 14

N-[3(R,S)-5,Cyclohexyl-2,3-dihydro-1-methyl-2-oxo-1H-1,4-benzodiazepin-3-yl]N'-[3-(phenylsulphonylaminocarbonyl) phenyl]urea

Step 1:
1-(Phenylsulphonylaminocarbonyl)-3-nitrobenzene

The title compound was prepared in the same way as that described in Example 11, Step 1, using benzenesulphonamide (4.7 g, 30 mmol), 3-nitrobenzoic acid (5 g, 30 mmol), 4-dimethylamino pyridine (3.66 g, 30 mmol), 1-[3-(dimethylamino)propyl]-3-ethyl carbodiimide hydrochloride (5.74 g, 30 mmol), and anhydrous dichloromethane (200 ml). The compound (8.05 g, 88%) was afforded as a colourless solid. mp 188°-190° C. $^1$H NMR (360 MHz, D$_6$-DMSO) δ 7.65 (2H, m), 7.72 (1H, m), 7.79 (1H,dd, J=8.0 and 8.0 Hz), 8.02 (2H, m), 8.28 (1H, dd, J=8.0 and 1.5 Hz), 8.45 (1H, dd, J: 8.0 and 1.5 Hz), 8.72 (1H, m).

Step 2:
1-(Phenylsulphonylaminocarbonyl)-3-amino-benzene

In the same way as that described in Example 11, Step 2, using 1-(phenylsulphonylaminocarbonyl)-3-nitrobenzene (5 g, 16 mmol), 10% palladium on carbon (0.5 g, 10% (w/w)) in water (3 ml) and ethanol (100 ml), the title compound (3 g, 67%) was afforded as a pale beige solid after recrystallisation from ethanol. mp 135°-138° C. $^1$H NMR (360 MHz, D$_6$-DMSO) δ 6.75-6.78 (1H, m), 6.96-6.98 (2H, m), 7.10 (1H, dd, J=8.0 and 8.0 Hz), 7.60-7.73 (3H, m), 7.97 (2H, m).

Step 3:
N-[3(R,S)-5-Cyclohexyl-2,3-dihydro-1-methyl-2-oxo-1H-1,4-benzodiazepin-3-yl]N'-[3,(phenylsulphonylaminocarbonyl) phenyl]urea The title compound was prepared in the same way as that described in Example 11, Step 4, using 5-cyclohexyl-1,3-dihydro-1-methyl-3(R,S)-[(4-nitrophenyloxycarbonyl)amino]-2H-1,4-benzodiazepin-2-one (0.3 g, 0.69 mmol), triethylamine (96 µl, 0.69 mmol), dimethylformamide (6 ml) and 1-(phenylsulphonylaminocarbonyl)-3-aminobenzene (0.21 g, 0.76 mmol). After recrystallisation from ethanol the compound (0.23 g, 58%) was isolated as a colourless solid. mp 215°-217° C. $^1$H NMR (360 MHz, D$_6$-DMSO) δ 0.85-0.98 (1H, m), 1.08-1.39 (3H, m), 1.41-1.66 (4H, m), 1.78 (1H, m), 1.89 (1H, m), 2.95 (1H, m), 3.32 (3H, s), 5.06 (1H, d, J=8.3 Hz), 7.32 (2H, m), 7.39 (2H, m), 7.52 (2H, m), 7.62 (3H, m), 7.72 (2H, m), 7.84 (1H,s), 7.97 (2H, m), 9.17 (1H,s), 12.50 (1H, brs).

EXAMPLE 15

N-[3(R,S)-5-Cyclohexyl-2,3-dihydro-1-methyl-2-oxo-1H-1,4-benzodiazepin-3-yl]
N'-[3-(methylcarbonVlaminosulphonyl) phenyl]urea

Step 1:
1-(MethylcarbonVlaminosulphonyl)-3-nitrobenzene

The title compound was prepared in the same way as that described in Example 11, Step 1, using 3-nitrobenzenesulphonamide (5.0 g, 25 mmol), acetic acid (1.43 ml, 24 mmol), 4-dimethylaminopyridine (4.8 g, 25 mmol), 1-[3-dimethylamino)propyl]-3-ethyl carbodiimide hydrochloride (4.8 g, 25 mmol) and anhydrous dichloromethane (420 ml). The title compound (5.4 g, 92%) was afforded as a colourless solid. mp 187°-190° C. $^1$H NMR (360 MHz, D$_6$-DMSO) δ 1.96 (3H, s), 7.95 (1H, dd, J=8.0 and 8.0 Hz), 8.34 (1H, dd, J=8.0 and 1.6 Hz), 8.56 (1H, dd, J=8.0 and 1.6 Hz), 8.62 (1H, dd, J=1.6 and 1.6 Hz), 12.42 (1H, brs).

Step 2:
1-(Methylcarbonylaminosulphonyl)-3-aminobenzene

In the same way as that described in Example 11, Step 2, using 1-(methylcarbonylaminosulphonyl)-3-nitrobenzene (2.9 g, 12 mmol), 10% palladium on carbon (0.4 g, 14% (w/w)) in water (3 ml) and ethanol (150 ml), the title compound (1.8 g, 70%) was afforded as a colourless soiid. mp 148°-150° C. $^1$H NMR (360 MHz, D$_6$-DMSO) δ 1.92 (3H, s), 5.64 (2H, brs), 6.80 (1H, dd, J=8.0 and 1.7 Hz), 6.98 (1H, d, J=7.6 Hz), 7.10 (1H, dd, J=2.0 and 2.0 Hz), 7.21 (1H, dd, J=7.9 and 7.9 Hz), 11.87 (1H, brs).

Step 3:
N-[3(R,S)-5-Cyclohexyl-2,3-dihydro-1-methyl-2-oxo-1H-1,4-benzodiazepin-3-yl]N'-[3-(methylcarbonylaminosulphonyl) phenyl]urea The title compound was prepared in the same way as that described in Example 11, Step 4, using 5-cyclohexyl-1,3-dihydro-1-methyl-3(R,S)-[(4-nitrophenyloxycarbonyl)amino ]-2H-1,4-benzodiazepin-2-one (0.5 g, 1.2 mmol), triethylamine (0.16 ml, 1.2 mmol), dimethylformamide (10 ml) and 1-(methylcarbonylaminosulphonyl)-3-aminobenzene (0.26 g, 1.2 mmol).After recrystallisation from methanol, the title compound (0.2 g, 34%) was afforded as a colourless solid. mp 195°-198° C. $^1$H NMR (360 MHz, D$_6$-DMSO) δ

0.87–0.99 (1H, m), 1.10–1.66 (7H, m), 1.78 (1H, m), 1.94 (1H, m), 1.91 (3H, s), 2.95 (1H, m), 3.30 (3H, s), 5.07 (1H, d, J=8.3 Hz), 7.39 (4H, m), 7.54 (2H, m), 7.64 (1H, dd, J=7.9 and 7.9 Hz), 7.76 (1H, d, J=7.9 Hz), 8.07 (1H, s), 9.42 (1H, s), 11.99 (1H, brs).

EXAMPLE 16

N-[3(R,S)-5-Cyclohexyl-2,3-dihydro-1-methyl-2-oxo-1H-1,4-benzodiazepin-3-yl]N'-[3-(methylsulphonylaminocarbonyl)phenyl]urea

Step 1:
1-(Methylsulphonylaminocarbonyl)-3-nitrobenzene

A solution of methylsulphonamide (5.37 g, 57 mmol) in anhydrous dichloromethane (100 ml), cooled to 0° C. was treated with triethylamine (7.9 ml, 57 mmol) followed by a solution of 3-nitrobenzoyl chloride (10 g, 54 mmol) in anhydrous dichloromethane (100 ml) dropwise. After stirring for 2 h at 0° C., the reaction mixture was washed with 1M HCl (100 ml). The precipitate which formed was collected by filtration and triturated with diethyl ether and was then recrystallised from methanol to afford the title compound (4.3 g, 31%) as a colourless crystalline solid. mp 175°–178° C. $^1$H NMR (360 MHz, D$_6$-DMSO) δ 3.42 (3H, s), 7.82 (1H, dd, J=8.0 and 8.0 Hz), 8.38 (1H, d, J=8.0 Hz), 8.49 (1H, d, J=8.0 Hz), 8.80 (1H,s).

Step 2:
1-(Methylsulphonylaminocarbonyl)-3-aminobenzene

In the same way as that described in Example 11, Step 2, using 1-(methylsulphonylaminocarbonyl)-3-nitrobenzene (4 g, 16 mmol), 10% palladium on carbon (0.5 g, 12.5% (w/w)) in water (5 ml) and ethanol (100 ml), the title compound (2.9 g, 83%) was afforded as a tan powder after trituration with diethyl ether. mp 153°–155° C. $^1$H NMR (360 MHz, D$_6$-DMSO) δ 3.3 (3H, s), 6.79 (1H, d, J=7.7 Hz), 7.05 (1H, d, J=7.7 Hz), 7.08 (1H, d, J=1.9 Hz), 7.13 (1H, dd, J=7.7 and 7.7 Hz).

Step 3:
N-[3(R,S)-5-Cyclohexyl-2,3-dihydro-1-methyl-2-oxo-1H-1,4-beniodiazepin-3-yl]N'-[3-(methylsulphonylaminocarbonyl). phenyl]urea The rifle compound was prepared in the same way as that described in Example 11, Step 4, using 5-cyclohexyl-1,3-dihydro- 1-methyl-3(R,S)-[(4-nitrophenyloxycarbonyl)amino]-2H-1,4-benzodiazepin-2-one (0.5 g, 1.2 mmol), triethylamine (0.16 ml, 1.2 mmol), dimethylformamide (10 ml) and 1-(methylsulphonylaminocarbonyl)-3-nitrobenzene (0.25 g, 1.2 mmol). After recrystallisation from ethanol, the compound (0.15 g, 26%) was afforded as a pale beige solid. mp 175° C (dec.). $^1$H NMR (360 MHz, D$_6$-DMSO) δ 0.88 (1H, m), 1.10–1.67 (7H, m), 1.72–1.81 (1H, m), 1.91 (1H, m), 2.95 (1H, m), 3.32 (3H, s), 3.34 (3H, s) 5.08 (1H, d, J=8.2 Hz), 7.37 (3H,m), 7.47 (1H, d, J=7.9 Hz), 7.56 (2H, m), 7.64 (1H, dd, J=7.0 and 7.0 Hz), 7.75 (1H, d, J=7.9 Hz), 7.91 (1H, s), 9.21 (1H, s), 12.07 (1H, brs).

EXAMPLE 17

N-[3(R,S)-5-Cyclohexyl-2,3dihydro-1-methyl-2-oxo-1H-1,4-benzodiazepin-3-yl]N'-[3-(trifiuoromethylcarbonylaminosulphonyl)phenyl]urea

Step 1:
1-(Trifluoromethylcarbonylaminosulphoyl)-3-nitrobenzene

A solution of 3-nitrophenylsulphonamide (5 g, 25 mmol) in anhydrous dimethylformamide (50 ml), under an atmosphere of nitrogen, cooled to 0° C., was treated with sodium hydride (1.08 g of a 55–60% dispersion in mineral oil, 27.5 mmol) in one portion. The mixture was stirred at 0° C. for 2 h and then trifiuoroacetic anthydride (3.8 ml, 27.5 mmol) was added dropwise. After stirring at 0° C. for a further 1 h, the solvent was evaporated in vacuo. The-residue was partitioned between dichloromethane (50 ml) and water (50 ml). The organic phase was separated and the aqueous phase extracted with dichloromethane (5×50 ml). The combined organic layers were evaporated in vacuo and azeotroped with toluene (2×50 ml). The residue was chromatographed on silica gel eluting with dichloromethane:methanol:acetic acid (85:10:5). The impure mixture was purified further by chromatography on silica gel, eluting with ethyl acetate:petrol (1:1) followed by ethyl acetate, to afford the title compound (2.7 g, 37%) as a colourless solid. mp 241° C. (dec.). $^1$H NMR (360 MHz, D$_6$-DMSO) δ 7.78 (1H, dd, J=7.9 and 7.9 Hz), 8.20 (1H, d, J=7.5 Hz), 8.35 (1H, dd, J=8.3 and 2.3 Hz), 8.54 (1H, dd, J=2.3 and 2.3 Hz).

Step 2:
1-(Trifiuoromethylcarbonylaminosulphonyl)-3-amino benzene

In the same way as that described in Example 11, Step 2, using 1-(trifluoromethylcarbonylaminosulphonyl)-3-nitrobenzene (2.7 g, 9.1 mmol), 10% palladium on carbon (0.25 g, 9% (w/w)) in water (3 ml) and ethanol (70 ml), the title compound (1.7 g, 70%) was afforded as a colourless solid. mp 106°–108° C. $^1$H NMR (360 MHz, D$_6$-DMSO) δ 6.59 (1H, m), 6.88 (1H, m), 7.02 (2H, m).

Step 3:
N-[3(R,S)-5-Cyclohexyl-2,3-dihydro-1-methyl-2-oxo-1H-1,4-benzodiazepin-3-yl] N'-[3-(trifiuoromethylcarbonylaminosulphonyl) phenyl]urea The title compound was prepared in the same way as that described in Example 11, Step 4, using 5-cyclohexyl-1,3-dihydro-1-methyl-3(R,S)-[(4-nitrophenyloxycarbonyl)amino]-2H-1,4-benzodiazepin-2-one (0.5 g, 1.2 mmol), triethylamine (0.16 ml, 1.2 mmol), dimethylformamide (10 ml) and 1-(trifluoromethyl carbonylaminosulphonyl)-3-aminobenzene (0.32 g, 1.2 mmol). The product was purified by chromatography on silica gel eluting with dichloromethane-methanol (9:1). This afforded the title compound (60 mg, 9%) as a pale beige solid. mp 190° C. (dec.). $^1$H NMR (360 MHz, D$_6$-DMSO) δ 0.86–1.00 (1H, m), 1.10–1.67 (7H,m), 1.76 (1H, m), 1.89–1.98 (1H, m), 2.95 (1H, m), 3.33 (3H, s) 5.08 (1H, m), 7.28 (3H, m), 7.38 (1H, m), 7.52 (2H, m), 7.64 (1H, m), 7.77 (2H, m), 9.21 (1H,s).

EXAMPLE 18

N-[3(R,S)-5-Cyclohexyl-2,3-dihydro-1-methyl-2-oxo-1H-1,4-benzodiazepin-3-yl] N'-[3-(trifluoromethylsulphonylaminocarbonyl)phenyl]urea

Step 1: Triffuoromethylsulphonamide

The title compound was prepared using the same procedure as described in Example 12, Step 1, replacing isopropylsulphonyl chloride with trifluoromethylsulphonyl chloride. The compound was purified 25 by trituration with hexane to give the product (8.5 g, 96%) as a colourless solid. mp 116°–119° C.

Step 2: 1-(Trifluoromethylsulphonylaminocarbonyl)-3-nitrobenzene

A solution of trifuoromethylsulphonamide (2.1 g, 14.1 mmol) in anhydrous dichloromethane (50 ml), cooled to 0° C. was treated with triethylamine (2.0 ml, 14.1 mmol) followed by a solution of 3-nitrobenzoyl chloride (2.5 g, 13.4 mmol) in anhydrous dichloromethane (50ml) dropwise. After stirring at 0° C. for 1h, the mixture was stirred at ambient temperature for 2 h. The mixture was extracted using 1M NaOH (100 ml), and the aqueous phase was acidified using 5M HCl. The aqueous phase was then extracted using dichloromethane (4×100 ml), followed by ethyl acetate (2×100 ml). The combined organic layers were dried (Na$_2$SO$_4$) and evaporated in vacuo to leave a yellow solid. This was recrystallise$_d$ from diethyl ether:hexane (1:1) to afford the title compound (1.5 g, 36%) as a pale yellow solid. mp 80°–83° C. $^1$H NMR (360 MHz, D$_6$-DMSO) δ 7.73 (1H, dd, J=8.0 and 8.0 Hz), 8.35 (2H, m), 8.56 (1H, brs), 8.68 (1H, m).

Step 3: I (Trifluoromethylsulphonylaminocarbonyl)-3-aminobenzene

In the same way as that described in Example 11, Step 2, using 1-(triffuoromethylsulphonylaminocarbonyl)-3-nitrobenzene (1.5 g, 5.6 mmol), 10% palladium on carbon (0.2 g, 13% (w/w)) in water (3 ml) and ethanol (40 ml), the title compound was afforded as a cream solid. This was triturated with diethyl ether to give a colourless solid (0.91 g, 68%). mp 255°–257° C. $^1$H NMR (360 MHz, D$_6$-DMSO) δ 7.43 (1H, m), 7.53 (1H, dd, J=7.9 and 7.9 Hz), 7.94 (2H, m).

Step 4: N-[3(R,S)-5-Cyclohexyl-2,3-dihydro-1-methyl-2oxo-1H-1,4-benzodiazepin-3-yl] N'-[3-(trifluoro methylsulphonylaminocarbonyl) phenyl]urea The title compound was prepared in the same way as that described in Example 11, Step 4, using 5-cyclohexyl-1,3-dihydro-1-methyl-3(R,S)-[(4-nitrophenyloxycarbonyl) amino]-2H- 1,4-benzodiazepin-2-one (0.5 g, 1.2 mmol), triethylamine (0.16 ml, 1.2 mmol) dimethylformamide (10 ml) and 1-trifuoromethylsulphonylaminocarbonyl)-3-aminobenzene (0.32 g,-1.2 mmol). After recrystallisation from ethanol the compound (0.17 g, 26%) was afforded as a colourless solid. mp 175° C. (dec.). $^1$H NMR (360 MHz, D$_6$-DMSO) δ 0.88–1.03 (1H, m) 1.08–1.41 (3H, m), 1.42–1.66 (4H, m) 1.78 (1H, m), 1.93 (1H, m), 2.96 (1H, m), 3.33 (3H, s), 5.10 (1H, brs), 7.21 (1H, dd, J=7.9 and 7.9 Hz), 7.19–7.31 (1H, m), 7.39 (1H, dd, J=7.2 Hz), 7.47 (1H, d, J=7.8 Hz), 7.57 (2H, m), 7.65 (1H, dd, J=7.1 and 7.1 Hz), 7.78 (2H, m), 9.11 (1H, s).

EXAMPLE 19

N-[3(R,S)-5-Cyclohexyl-2,3-dihydro-1-(2-methylpropyl)-2-oxo-1H-1,4-benzodiazepin,3yl] N'-[3-(methylsulphonylaminocarbonyl)phenyl]urea

Step 1: 5-Cyclohexyl-1,3-dihydro-1-(2-methylpropyl)-3(R,S)-[(4-nitrophenyloxycarbonyl)amino]-2H-1,4-benzodiazepin-2-one 5Cyclohexyl-1,3-dihydro-1-(2-methylpropyl)-3(R,S)[(benzyloxycarbonyl )amino]-2H-1,4-benzodiazepin-2-one (1.0 g, 2.24 mmol) was dissolved in formic acid/methanol (100 ml of a 4 5% (v/v) solution) and added over 5 min to a stirred suspension of 10% palladium on carbon (0.3 g, 30% (w/w)) in formic acid/methanol (10 ml of a 4.5% (v/v) solution). After 1.5 h at ambient temperature, the catalyst was filtered off and washed sequentially with methanol and acetone. The flitrate was evaporated in vacuo and the residue partitioned between ethyl acetate (25 ml) and 10% sodium carbonate solution (25 ml). The organic phase was separated and.the aqueous phase extracted with ethyl acetate (2×25 ml). The combined organic phases were dried (Na$_2$SO$_4$) and evaporated in vacuo to give a yellow gum which was used without further purification.

A solution of the crude amine (0.7 g, 2.24 mmol) in anhydrous tetrahydrofuran (15 ml) under an atmosphere of nitrogen, at 0° C., was treated with triethylamine (0.31 ml, 2.24 mmol), followed by a solution of the 4-nitrophenyl chloroformate (0.45 g, 2.24 mmol) in anhydrous tetrahydrofuran (10 ml) dropwise. After stirring at ambient temperature for 20 min, the solid which precipitated from the mixture was filtered and the flitrate was evaporated in vacuo to leave a pale yellow solid. The solid was triturated with diethyl ether to give the title compound (0.88 g, 82%) as a colourless solid. mp 163–165° C. $^1$H NMR (360 MHz, CDCl$_3$) δ 0.76 (3H, d, J=6.7 Hz), 0.82 (3H, d, J=6.7 Hz), 1.12–1.44 (5H, m), 1.53–1.79 (4H, m) 1.85–1.95 (1H, m), 2.05–2.14 (1H, m), 2.85 (1H, m), 3.47 (1H, dd J=13.8 and 4.3 Hz), 4.32 (1H, dd, J=13.8 and 9.3 Hz), 5.13 (1H, d, J=8.1 Hz), 6.93 (1H, d, J=8.1 Hz), 7.26–7.39 (4H, m), 7.52 (1H, m), 7.60 (1H, d, J=6.5 Hz), 8.22 (2H, m).

Step 2: N-[3(R,S)-5-Cyclohexyl-2,3-dihydro-1-(2-methylpropyl)-2-oxo-1H-1,4-benzodiazepin-3-yl] N'-[3-(methylsulphonylaminocarbonyl) phenyl]urea The title compound was prepared from 5-cyclohexyl-1,3-dihydro-1-(2-methylpropyl)-3(R,S)-[(4-nitrophenyloxycarbonyl)amino]-2H- 1,4-benzodiazepin-2-one (0.3 g, 0.63 mmol), triethylamine (87 μl, 0.63 mmol), dimethylformamide (6 ml) and 1-(methylsulphonylaminocarbonyl)-3-aminobenzene (0.15 g, 0.69 mmol) [Example 16, Step 2] using the procedure described in Example 11, Step 4. The product (0.17 g, 49%) was afforded as a pale cream solid after trituration with methanol. mp 250°–252° C: $^1$H NMR (360 MHz, D$_6$-DMSO) δ 0.64 (3H, d, J=6.6 Hz), 0.76 (3H, d, J=6.7 Hz), 0.92–1.70 (9H, m), 1.74–1.82 (1H, m), 1.98 (1H, m), 2.90–3.30 (1H, m), 3.33 (3H, m), 3.62 (1H, dd, J=14.0 and 4.7 Hz), 4.14 (1H, dd, J=13.9 and. 9.4 Hz), 5.04 (1H, m), 7.37 (3H, m), 7.47 (1H, m), 7.60 (3H, m), 7.78 (1H, m), 7.90 (1H, s), 9.18 (1H, s), 12.06 (1H, brs).

EXAMPLE 20

N-[3(R,S)-5-Cyclopentyl-2,3-dihydro-1-ethyl-2-oxo-1H-1,4-benzodiazepin-3-yl] N'-[3-(methylcarbonylaminosulphonyl) phenyl]urea

Step 1:
5-Cyclopentyl-1,3-dihydro-1-ethyl-3(R,S)-[(4-nitrophenyloxycarbonyl)amino]-2H-1,4-benzodiazepin-2-one A solution of crude 3(R,S)-amino-5-cyclopentyl-1,3-dihydro-1-ethyl-2H-1, 4-benzodiazepin-2-one [Example 5, Step 5] (0.23 g, 0.92 mmol) in dry tetrahydrofuran (15 ml) under an atmosphere of nitrogen, at 0° C., was treated with triethylamine (0.11 ml, 0.92 mmol) followed by a solution of 4-nitrophenyl chloroformate (184 mg, 0.92 mmol) in tetrahydrofuran (10 ml). After stirring at ambient temperature for 30 min the solid which precipitated was removed by filtration and the tiltrate concentrated in vacuo to afford the title compound (0.32 g, 79%) as a colourless solid. mp 136°–138° C. $^1$H NMR (360 MHz, CDCl$_3$) δ 0.9 (3H, t, J=7 Hz), 1.0–2.2 (8H,m), 3.50 (1H, p, J=7 Hz), 3.70 (1H, m), 4.18–4.28 (1H, m), 5.14 (1H, d, J=8 Hz), 7.30–8.20 (8H, m), 9.12 (1H, d, J=8 Hz).

Step 2:
N-[3(R,S)-5-Cyclopentyl-2,3,dihydro-1-ethyl-2-oxo-1H-1,4-benzodiazepin-3-yl]N'-[3-(methylcarbonylaminosulphonyl) phenyl]urea This compound was prepared from 5-cyclopentyl-1,3-dihydro-1-ethyl-3(R,S)-[( 4-nitrophenyloxycarbonyl)amino]-2H-1,4-benzodiazepin-2-one (141 mg, 0.32 mmol) and 1-(methylcarbonylaminosulphonyl)-3-aminobenzene [Example 15, Step 2] (68 mg, 0.32 mmol) using the procedure described in Example 11, Step 4, to afford the product (50 mg, 30%) as a colourless powder. mp 202°–204° C. $^1$H NMR (250 MHz, D$_6$-DMSO) δ 0.9 (3H, t, J=7 Hz), 1.00–1.20 (1H, m), 1.40–1.90 (6H, m), 1.91 (3H, s), 2.00–2.20 (1H, m), 3.45–3.62 (1H, m) 3.64–3.84 (1H, m), 4.16–4.36 (1H, m), 5.05 (1H, d, J=8 Hz), 7.30–7.90 (8H, m), 8.06 (1H, s), 9.41 (1H, s), 12.01 (1H, s).

EXAMPLE 21

N-[3(R,S)-5-Cyclohexyl-2,3-dihydro-1-methyl-2-oxo-1H-1,4-benzodiazepin-3-yl]N'-[3-(1,3,4-thiadiazol-2-ylaminosulphonyl )phenyl]urea

Step 1:
1-(1,3,4-Thiadiazol-2-ylaminosulphonyl)-3-nitrobenzene

To a stirred suspension of 2-amino-1,3,4-thiadiazole (1.5 g, 15 mmol) in anhydrous pyridine (6 ml) at 0° C., under nitrogen, was added 3-nitrobenzenesulphonyl chloride (3.5 g, 16 mmol) portionwise. The mixture turned yellow and set solid. The mixture was then heated at 120° C. for 1 h before aqueous sodium hydroxide (20% (w/w), 3.3 ml) was added cautiously. Heating was continued for a further 15 min then the solution allowed to cool to ambient temperature. The mixture was evaporated in vacuo and the residue evaporated with water (2×50 ml) followed by toluene (2×50 ml). The residue was then taken up in water and the resultant brown solid collected by filtration. This was then recrystallised from glacial acetic acid. The title compound (1.4 g, 37%) was isolated as a yellow solid, which contained one mole of acetic acid. mp 189°–192° C. $^1$H NMR (250 MHz, D$_6$-DMSO) δ 7.88 (1H, dd, J=8 and 8 Hz), 8.23 (1H, dd, J=8 and 1 Hz), 8.45 (2H, m), 8.83 (1H, s).

Step 2: 1-( 1,3,4-Thiadiazol-2-ylaminosulphonyl)-3-aminobenzene

A suspension of 1-(1,3,4-thiadiazol)-2-ylaminosulphonyl)-3-nitrobenzene (1.3 g, 4.6 mmol) in ethanol (50 ml)/water (5 ml)/5N hydrochloric acid (10 ml) was hydrogenated for 4 h at 40 psi, using a palladium on carbon catalyst (0.5 g, 38% (w/w)). After this time the catalyst was filtered off and the filtrate evaporated in vacuo. After azeotroping with toluene (20 ml) the resultant solid was dissolved in water (30 ml) and the solution adjusted to pH 5 using 1M sodium hydroxide solution. The mixture was extracted with ethyl acetate (2×20 ml) and the organic layers combined and dried (Na$_2$SO$_4$). The flitrate was evaporated in vacuo and the residue azeotroped with toluene (20 ml) then triturated with anhydrous ether. The title compound (408 mg, 35%) was isolated as a beige solid. mp 155°–158° C. $^1$H NMR (360 MHz, D$_6$-DMSO) δ 6.72 (1H, dd, J=8 and 2 Hz), 6.87 (1H, d, J=8 Hz), 6.98 (1H, dd, J=2 and 2 Hz), 7.15 (1H, dd, J=8 and 8 Hz), 8.76 (1H, s).

Step 3:
N-[3(R,S)-5-Cyclohexyl-2,3-dihydro-1-methyl-2-oxo-1H-1,4,benzodiazepin-3-yl] N'-[3-(1,3,4-thiadiazol-2-ylaminosulphonyl)nhenyl]urea To a stirred solution of 5-cyclohexyl-1,3-dihydro-1-methyl-3(R,S)-[(4-nitrophenyloxycarbonyl)-amino]-2H-1,4-benzodiazepin-2-one [Example 11, Step 3], (200 mg, 0.46 mmol) in anhydrous dimethylformamide (3 ml), under nitrogen, was added triethylamine (63 μl, 0.46 mmol) dropwise over 5 min. After stirring at room temperature for a further 5 min a solution of 1-(1,3,4-thiadiazol-2-ylaminosulphonyl )-3-aminobenzene (117 mg, 0.46 mmol) in dimethylformamide (3 ml) was added dropwise over 5 min. The solution was then heated at 60° C. for 5 h, then the mixture allowed to cool to ambient temperature. The solvent was removed in vacuo and the residue partitioned between ethyl acetate (20 ml) and 20% aqueous acetic acid (20 ml). The organic phase was separated, dried (MgSO$_4$) and evaporated in vacuo. The residue was azeotroped with toluene (2×20 ml), then triturated in toluene (20 ml) and the solid filtered off. The solid was triturated in hot methanol, filtered and stirred in anhydrous ether overnight. The title compound (63 mg, 24%) was isolated as a pale pink solid. mp 233°–235° C. $^1$H NMR (360 MHz, D$_6$-DMSO) δ 0.91 (1H, m), 1.14–1.88 (9H, m), 2.93 (1H, m), 3.32 (3H, s), 5.05 (1H, d, J=8 Hz), 7.30–7.40 (5H, m), .7.55 (1H, d, J=8 Hz), 7.64 (1H, dd, J=7 Hz), 7.75 (1H, d, J=8 Hz), 8.01 (1H, s), 8.76 (1H, s), 9.33 (1H, s).

EXAMPLE 22

N-[3(R,S)-5-Cyclohexyl-2,3-dihydro-1-methyl-2-oxo-1H-1,4-benzodiazepin-3-yl] N'-[3-(2pyrazinylaminosulphonyl)phenyl]urea Step 1: 1-(2-Pyrazinylaminosulphonyl)-3-nitrobenzene To a stirred solution of 2-aminopyrazine (4.1 g, 0.043 mol) in anhydrous pyridine (17 ml) at 0° C., under nitrogen, was added 3-nitrobenzenesulphonyl chloride (10 g, 0.045 mol) portionwise. The mixture was warmed to room temperature and stirred for 3 h. After this time aqueous sodium hydroxide (18% (w/w), 10 ml) was added cautiously. Stirring was continued for a further 15 min then the mixture was evaporated in vacuo. The residue was then taken up in water (100 ml) and evaporated once more. The solid was taken up in water (100 ml) and filtered off. This material was chromatographed on silica gel, using dichloromethane:methanol (95:5) as the eluant, to afford the sulphonamide (1.15 g, 10%) as a brown solid. $^1$H NMR (360MHz, D6-DMSO) δ 7.91 (1H, dd, J=8 and 8 Hz), 8.24 (1H, d, J=2 Hz), 8.27 (1H, d, J=2 Hz), 8.37 (2H, m), 8.46 (1H, dd, J=8 and 2 Hz), 8.72 (1H, s), 12.00 (1H, brs). MS (CI, NH$_3$) 281 (M+1).

Step 2:
N-[3(R,S)-5-Cyclohexyl-2,3-dihydro-1-methyl-2-oxo-1H-1,4-benzodiazepin-3-yl] N'-[3-(2-pyrazinylaminosulphonyl)phenyl]urea 1-(2-Pyrazinylaminosulphonyl)-3-nitrobenzene (1.15 g, 4.1 mmol) was added portionwise to a hot suspension of iron powder (4 g) in ethanol (15 ml)/5N hydrochloric acid (1 ml) under nitrogen. The mixture was heated at reflux for 3 h then the mixture filtered whilst hot. On cooling a precipitate separated which was collected by filtration and triturated with ether. The solid (142 mg, 14%) was assumed to be the desired aniline and was used without further purification.

To a stirred solution of 5-cyclohexyl-1,3-dihydro-1-methyl-3(R,S )-[(4-nitrophenyloxycarbonyl)amino]-2H-1,4-benzodiazepin-2-one (335 mg, 0.77mmol) [Example 11, Step 3] in anhydrous tetrahydrofuran (4 ml), under nitrogen, was added triethylamine (106 μl, 0.77 mmol) dropwise over 5 min. After stirring at room temperature for a further 5 mina solution of the aniline (194 mg, 0.77 mmol) (prepared as described above) in anhydrous tetrahydrofuran (4 ml) was added dropwise over 5 min. The mixture was headed at reflux for 12 h, then cooled to ambient temperature and evaporated in vacuo. The residue was partitioned between ethyl acetate (20 ml) and 20% aqueous acetic acid (20 ml). The undissolved solid was filtered off and washed with anhydrous ether. On standing more solid precipitated from the tiltrate and was collected by filtration. The solids were combined and subjected to preparative thin layer chromatography, using dichloromethane:methanol:acetic acid 94:6:0.4 as the eluant. The title compound (60 mg, 14%) was isolated as a beige solid. mp 255°–257° C. (dec.). $^1$H NMR (360 MHz, D6-DMSO+TFA) δ 0.97 (1H, m), 1.15–1.91 (9H, m), 2.96 (1H, m), 3.34 (3H, s), 5.1 (1H, brs), 7.38–7.49 (5H, m), 7.56 (1H, d, J=8 Hz), 7.65 (1H, d, J=7 Hz), 7.78 (1H, d, J=7 Hz), 8.15 (1H, s), 8.21 (2H, m), 8.36 (1H, s), 9.42 (1H, s).

EXAMPLE 23
N-[3(R,S)-5-Cyclohexyl-2,3-dihydro-1methyl-2-oxo-1H-1,4-benzodiazepin-3-yl] N'-[3-(ethylsulphonylaminocarbonyl)phenyl]urea

Step 1: Ethylsulphonamide

The title compound was prepared using the same procedure as described in Example 12, Step 1, replacing isopropylsulphonyl chloride with ethylsulphonyl chloride. The compound was purified by trituration with hexane to give the product (6.17 g, 73%) as a colourless solid. mp 53°–56° C. $^1$H NMR (360 MHz, D6-DMSO) δ 1.22 (3H, t, J=7.4 Hz), 2.95 (2H, q, J=7.4 Hz), 6.69 (2H, brs).

Step 2:
1-(Ethylsulphonylaminocarbonyl)-3-nitrobenzene

The title compound was prepared in the same way as that described in Example 11, Step 1, using ethyl sulphonamide (3 g, 27.5 mmol), 3-nitrobenzoic acid (4.6 g, 27.5 mmol), 4-dimethylaminopyridine (3.36 g, 27.5 mmol), 1-[3-(dimethylamino)propyl]-3-ethyl carbodiimide hydrochloride (5.28 g, 27.5 mmol) and anhydrous dichloromethane (200 ml). The title compound (6 g, 84%) was afforded as a colourless solid. mp 178°–181° C. $^1$H NMR (360 MHz, D6-DMSO) δ 1.28 (3H, t, J=7.4 Hz), 3.54 (2H, q, J=7.4 Hz), 7.83 (1H, dd, J=8.0 and 8.0 Hz), 8.33–8.38 (1H, m), 8.47–8.50 (1H, m), 8.75–8.90 (1H, m), 12.40 (1H, brs).

Step 3:
1-(Ethylsulphonylaminocarbonyl)-3-aminobenzene

In the same way as that described in Example 11, Step 2, using 1-(ethylsulphonylaminocarbonyl )-3-nitrobenzene (3 g, 11.6 mmol), 10% palladium on carbon (0.3 g, 10% (w/w)) in water (3 ml) and ethanol (100 ml), the title compound (1.95 g, 74%) was afforded as a pale beige solid after recrystallisation from ethanol. mp 129°–132° C. $^1$H NMR (360 MHz, D6-DMSO) δ 1.24 (3H, t, J=7.4 Hz), 3.47 (2H, q, J=7.4 Hz), 5.40 (2H, brs), 6.77–6.83 (1H, m), 7.02–7.08 (2H, m), 7.13 (1H, dd, J=7.8 and 7.7 Hz).

Step 4: N-[3(R,S)-5-Cyclohexyl-2,3-dihydro-1-methyl-2-oxo-1H-1,4-benzodiazepin-3-yl] N'-[3-(ethylsulphonylaminocarbonyl)phenyl]urea The title compound was prepared in the same way as that described in Example 11, Step 4, using 5-cyclohexyl-1,3-dihydro-1-methyl-3(R,S)-[(4nitrophenyloxycarbonyl)amino]-2H- 1,4-benzodiazepin-2-one (0.25 g, 0.57 mmol), triethylamine (80 μl, 0.57 mmol), dimethylformamide (5ml) and 1-(ethylsulphonylaminocarbonyl)-3-nitrobenzene (0.14 g, 0.63 mmol). After trituration with hot methanol, the compound (125 mg, 42%) was afforded as a colourless solid. mp 210° C. (dec.). $^1$H NMR (360 MHz, D6-DMSO) δ 0.86–0.98 (1H, m), 1.10–1.25 (2H, m), 1.23 (3H, t, J=7.4 Hz), 1.26–1.64 (5H, m), 1.72–1.80 (1H, m), 1.87–1.96 (1H, m), 2.88–2.99 (1H, m), 3.33 (3H, s), 3.48 (2H, q, J=7.4 Hz), 5.08 (1H, d, J=8.3 Hz), 7.31–7.42 (3H, m), 7.47 (1H, d, J=7.9 Hz), 7.52–7.58 (2H, m), 7.67 (1H, dd, J=7.9 and 7.8 Hz), 8.76–8.80 (1H, m), 7.92 (1H, dd, J=1.8 and 1.8 Hz), 9.21 (1H, s), 11.98 (1H, brs).

EXAMPLE 24

Chiral separation of N-[3(R,S)-5-cyclohexyl-2,3-dihydro-1-methyl-2-oxo-1H-1,4-benzodiazepin-3-yl] N'-[3-(isopropylsuphonylaminocarbonyl)phenyl]urea N-[3(R,S)-5-Cyclohexyl-2,3-dihydro-1-methyl-2-oxo-1H-1,4-benzodiazepin-3-yl] N'-[3-(isopropylsulphonyl aminocarbonyl)phenyl]urea ( 110 mg, 0.20 mmol) [Example 12], was dissolved in tetrahydrofuran (40 mg/ml). 150 μl of solution was injected onto a dinitrobenzoyl leucine column (250×8.0 mm i.d., 5 μm) per run, using 2% methanol in dichloromethane plus 0.5% acetic acid as the mobile phase. Using a flow rate of 4 ml/min and UV detection at 300 nm, the two enantiomers were efficiently separated. The fractions containing each separate enantiomer were combined and evaporated in vacuo.

Peak A (45 mg):
Retention time 6 min. mp 190° C. (dec.).
Purity: A:B >99:1
Peak B (40 mg):
Retention time 13 min. mp 195° C. (dec.).
Purity: A:B 97:3.

EXAMPLE 25

N-[3(R,S)-5-Cyclohexyl-2,3-dihydro-1-propyl-2-oxo-1H-1,4-benzodiazepin-3-yl]
N'-(3-(methylsulphonylaminocarbonyl)phenyl]urea Step 1: 5-Cyclohexyl-1,3-dihydro-1-propyl,3(R,S)[(benzyloxycarbonyl)amino]-2H-1,4-benzodiazepin-2-one A solution of 5-cyclohexyl-1,3-dihydro-3(R,S)-[(benzyloxycarbonyl)amino]-2H-1,4-benzodiazepin-2-one ( 2 g, 5.1 mmol) in anhydrous dimethylformamide (15 ml), under an atmosphere of nitrogen, was treated with sodium hydride (0.22 g of a 55–60% dispersion in mineral oil, 5.1 mmol) in one portion, at 0° C. After 45 min at 0° C., 1-iodopropane (0.55ml, 5.6 mmol) was added in one portion and the solution allowed to reach ambient temperature and stirred overnight. After this time the solvent was removed under reduced pressure, and the crude residue partitioned between water (25 ml) and dichloromethane (25 ml). The organic phase was separated and the aqueous phase extracted with dichloromethane (3×25 ml). The combined organic layers were washed with brine (50 ml), dried (MgSO$_4$) and evaporated in vacuo. The residue was triturated with diethyl ether to give the title compound (1.74 g, 79%) as a colourless solid. mp 160°–163° C. $^1$H NMR (360 MHz, CDCl$_3$) δ 0.82 (3H, t, J=10.5 Hz), 0.94–1.48 (5H, m), 1.50–1.76 (5H, m), 1.79–1.90 (1H, m), 1.96–2.08 (1H, m), 2,70–2.84 (1H, m), 3.46–3.59 (1H, m), 4.22–4.35 (1H, m), 5.06–5.16 (3H, m), 5.07 (1H, d, J=12.0 Hz), 7.21–7.40 (7H, m), 7.44–7.59 (2H, m).

Step 2:
5-Cyclohexyl-1,3-dihydro-1-propyl-3(R,S)-[(4-nitrophenyloxycarbonyl )amino]-2H-1,4-benzodiazepin-2-one 5-Cyclohexyl-1,3-dihydro-1-propyl-3(R,S)[(benzyloxycarbonyl)amino]-2H-1,4-benzodiazepin-2-one (1.6 g, 3.7 mmol) was dissolved in formic acid/methanol (130 ml of a 4.5% (v/v) solution) and added over 5 min to a stirred suspension of 10% palladium on carbon (0.4 g, 25% (w/w)) in formic acid/methanol (20 ml of a 4.5% (v/v) solution). After 1 h at ambient temperature, the catalyst was filtered off and washed sequentially with methanol and acetone. The filtrate was evaporated in vacuo and the residue partitioned between ethyl acetate (25 ml) and 10% sodium carbonate solution (25 ml). The organic phase was separated and the aqueous phase extracted with ethyl acetate (3×25 ml). The combined organic phases were dried (Na$_2$SO$_4$) and evaporated in vacuo to give a yellow gum which was used without further purification.

A solution of the crude amine (1.1 g, 3.7 mmol) in anhydrous tetrahydrofuran (15 ml) under an atmosphere of nitrogen, at 0° C., was treated with triethylamine (0.51 ml, 3.7 mmol), followed by a solution of 4-nitrophenyl chloroformate (0.74 g, 3.7 mmol) in anhydrous tetrahydrofuran (15 ml) dropwise. After stirring at ambient temperature for 15 min, the solid which precipitated from the mixture was removed by filtration, and the filtrate was evaporated in vacuo to leave an orange solid. The solid was triturated with diethyl ether to give the title compound (1.3 g, 76%) as a colourless solid. mp 152°–155° C. $^1$H NMR (360 MHz, CDCl$_3$) δ 0.85 (3H, t, J=7.4 Hz), 1.02–1.50 (6H, m), 1.56–1.76 (4H, m), 1.84–1.93 (1H, m), 2.00–2.08 (1H, m), 2.76–2.87 (1H, m), 3.53–3.63 (1H, m), 4.26–4.36 (1H, m), 5.14 (1H, d, J=8.0 Hz), 6.93 (1H, d, J=8.3 Hz), 7.22–7.40 (4H, m), 7.50–7.62 (2H, m), 8.18–8.26 (2H, m).

Step 3:
N-[3(R,S)-5-Cyclohexyl-2,3-dihydro-1-propyl-2-oxo-1H-1,4-benzodiazepin-3-yl]N'-[3-(methylsulphonylaminocarbonyl)phenyl]urea The title compound was prepared from 5-cyclohexyl-1,3-dihydro-1-propyl-3(R,S)-[(4-nitrophenyloxycarbonyl)amino]-2H-1,4-benzodiazepin-2-one (0.3 g, 0.65 mmol), triethylamine (90 μl, 0.65 mmol), dimethylformamide (6 ml) and 1-(methylsulphonylaminocarbonyl)-3-aminobenzene ( 0.15 g, 7.1 mmol) [Example 16, Step 2] using the procedure described in Example 11, Step 4. The product (0.16 g, 46%) was afforded as a cream solid after trituration with hot methanol. mp 205° C. (dec.). $^1$H NMR (360 MHz, D$_6$-DMSO) δ 0.73 (3H, t, J=7.3 Hz), 0.86–1.00 (1H, m), 1.08–1.42 (5H, m), 1.43–1.54 (2H, m), 1.57–1.67 (2H, m), 1.74–1.83 (1H, m), 1.87–1.96 (1H, m), 2.91–3.01 (1H, m), 3.33 (3H, s), 3.62–3.72 (1H, m), 4.16–4.26 (1H, m), 5.04 (1H, d, J=7.8 Hz), 7.34–7.43 (3H, m), 7.47 (1H, d, 7.8 Hz), 7.56–7.68 (3H, m), 7.77 (1H, d, J=7.7 Hz), 7.91 (1H, dd, J=1.9 and 1.9 Hz), 9.20 (1H, s), 12.04 (1H, brs).

EXAMPLE 26

N-[3(R,S)-5-Cyclohexyl-2,3-dihydro-1-methyl-2-oxo-1H-1,4-benzodiazepin-3-yl]N'-[3-(thiazol-2-ylaminosulphonyl)phenyl]urea Step 1: 1-(Thiazol-2-ylaminosulphonyl)-3-nitrobenzene To a solution of 2-aminothiazole (1 g, 10.5 mmol) in dry pyridine (3 ml) was added, portionwise, 3-nitrobenzenesulphonyl chloride (2.32 g, 10.5 mmol), maintaining the internal temperature below 55° C. After addition was complete, the mixture was heated at 100° C. for 75 min. 4M Sodium hydroxide solution (2.75 ml, 11 mmol) was then added dropwise and heating was continued for a further 5 min. After cooling, water (25 ml) was added and the precipitate was collected by filtration to afford the product (2.48 g, 87%) as a brown solid. mp 195° C. (dec.). $^1$H NMR (360 MHz, D$_6$-DMSO) δ 6.91 (1H, d, J=4.6 Hz), 7.31 (1H, d, J=4.5 Hz), 7.86 (1H, dd, J=8.0 and 8.1 Hz), 8.20–8.26 (1H, m), 8.40–8.45 (1H, m), 8.46–8.49 (1H, m), 13.00 (1H, brs).

Step 2:
1-(Thiazol-2-ylaminosulphonyl)-3-aminobenzene

To a suspension of 1-(thiazol-2-ylaminosulphonyl )-3-nitrobenzene (0.5 g, 1.8 mmol) in ethanol (50 ml) was added 10% palladium on carbon. (0.25 g, 50% (w/w)) in water (2 ml) and 5M hydrochloric acid (1 ml, 5 mmol). The mixture was hydrogenated at 45 psi for 3 h. The catalyst was filtered off and washed with ethanol. The solvents were evaporated in vacuo and the residue chromatographed on silica gel using 10% methanol in dichloromethane as the eluant to afford the product (0.34 g, 76%) as a pale yellow solid. mp 187°–190° C. $^1$H NMR (360 MHz, D$_6$-DMSO) δ 5.49 (2H, brs), 6.66–6.73 (1H, m), 6.80 (1H, d, J=4.6 Hz), 6.85–6.90 (1H, m), 6.98–7.02 (1H, m), 7.11 (1H, dd, J=7.9 and 7.9 Hz), 7.22 (1H, d, J=4.7 Hz), 12.59 (1H, brs).

Step 3:
N-[3(R,S)-5-Cyclohexyl-2,3-dihydro-1-methyl-2-oxo-1H-1,4-benzodiazepin-3-yl]N'-[3-(thiazol-2-ylaminosulphonyl)phenyl]urea The title compound was prepared from 5-cyclohexyl-1,3-dihydro-1-methyl-3(R,S)-[(4-nitrophenyloxycarbonyl)amino]-2H-1,4-benzodiazepin-2-one (0.3 g, 0.69 mmol), triethylamine (96 μl, 0.69 mmol), dimethylformamide (6 ml) and 1-(thiazol-2-ylaminosulphonyl)-3aminobenzene (0.19 g, 0.76 mmol) using the procedure described in Example 11, Step 4. The product (125 mg, 33%) was afforded as a cream solid after trituration with methanol. mp 230° C. (dec.). $^1$H NMR (360 MHz, D$_6$-DMSO) δ 0.84–0.96 (1H, m), 1.08–1.65 (7H, m), 1.71–1.81 (1H, m), 1.86–1.94 (1H, m), 2.88–2.96 (1H, m), 3.32 (3H, s), 5.06 (1H, d, J=8.2 Hz), 6.80 (1H, d, J=4.6 Hz), 7.22 (1H, d, J=4.6 Hz), 7.28–7.42 (5H, m), 7.55 (1H, d, J=7.4 Hz), 7.64 (1H, dd, J=7.1 and 7.0 Hz), 7.75 (1H, d, J=7.9 Hz), 7.98 (1H, s), 9.30 (1H, s), 12.63 (1H, brs).

EXAMPLE 27

(−)-N-[3(R)-5-Cyclohexyl-2,3-dihydro-1-methyl-2-oxo-1H-1,4-benzodiazepin-3-yl]N'-[3-(phenylsulphonylaminocarbonyl)phenyl]urea Step 1:
3(R,S)-Amino-5-cyclohexyl-1,3-dihydro-1-methyl-2H-1,4,-benzodiazepin-2-one A mixture of 5-cyclohexyl-1,3-dihydro-1-methyl-3(R,S)-[(benzyloxycarbonyl)amino]-2H-1,4-benzodiazepin-2-one (3.0 g, 7.4 mmol) and hydrobromic acid (45% in acetic acid, 6.2 ml) was stirred for 1 h at room temperature under an atmosphere of nitrogen. The mixture was then diluted with cold anhydrous diethyl ether (40 ml) and stirred at 0° C. for 45 min. The white precipitate was collected by filtration, washed with cold diethyl ether (4×30 ml) and then dissolved in a mixture of water (30 ml) and aq. sodium hydroxide (2M, 15 ml). The basic aqueous phase was extracted with ethyl acetate (3×70 ml) and the combined organic layers were washed with brine (30 ml), dried (Na$_2$SO$_4$) and concentrated. The residue was chromatographed on silica gel, using 94:6, dichloromethane:methanol as the eluant, to afford the title compound (1.6 g, 80%) as a pale pink solid. mp 133°–136° C. $^1$H NMR (360 MHz, CDCl$_3$) δ 1.02–1.40 (4H, m), 1.47–1.56 (1H, m), 1.61–1.74 (3H, m), 1.84–1.91 (1H, m), 1.96–2.06 (1H, m), 2.17 (2H, brs), 2.70–2.80 (1H, m), 3.39 (3H, s), 4.29 (1H, s), 7.20–7.27 (2H, m), 7.44–7.54 (2H, m).

Step 2:
3(R,S)-[2(R)-(tert-Butyloxycarbonyl)amino-3phenylpropionylamino]-5-cyclohexyl-1,3-dihydro-1-methyl-2H-1,4-benzodiazepin-2-one To a solution of 3(R,S)-amino-5-cyclohexyl-1,3-dihydro-1-methyl-2H-1,4-benzodiazepin-2-one (4 g, 14.8 mmol) in anhydrous dimethylformamide (35 ml), under an atmosphere of nitrogen, was added in succession Boc-D-phenyl-alanine (4.11 g, 15.4mmol), 1-hydroxybenzotriazole trihydrate (2.09 g, 15.4 mmol) and 1-ethyl-3-[3-(dimethylamino) propyl]carbodiimide hydrochloride (2.97 g, 15.4 mmol). Triethylamine (2.16 ml, 15.4 mmol) was then added and the resulting suspension was stirred at ambient temperature for 20 min. The solvent was removed under reduced pressure and the residue was partitioned between ethyl acetate (50 ml) and 10% citric acid solution (50 ml). The organic phase was separated and the aqueous phase extracted with ethyl acetate (3×50 ml). The combined organic phases were washed with 10% sodium hydroxide solution (50 ml), water (50 ml) and brine (50 ml), dried (MgSO$_4$) and evaporated in vacuo. The residue was chromatographed on silica gel, using 1:1 petrol:ethyl acetate as the eluant, to afford the product (7.26, 95%) as a pale yellow solid. mp 95°–98° C. $^1$H NMR (360 MHz, CDCl$_3$) δ 0.99–1.11 (1H, m), 1.16–1.72 (7H, m), 1.40 (9H, s), 1.83–1.92 (1H, m), 1.98–2.06 (1H, m), 2.73–2.83 (1H, m), 3.10–3.24 (2H, m), 3.38 (3H, s), 4.53 (1H, brs), 4.98 (1H, brs), 5.28–5.34 (2H, m), 7.19–7.32 (7H, m), 7.49–7.58 (2H, m).

Step 3:
(+)-3(R)-(2(R)-Amino-3-phenylpronionylamino)-5-cyclohexyl-1,3-dihydro-1-methyl-2H-1,4-benzodiazepin-2-one 3(R,S)-[2(R)-(tert-Butyloxycarbonyl)amino-3phenylpropionylamino]-5-cyclohexyl-1,3-dihydro-1-methyl-2H-1,4-benzodiazepin-2-one (4.7 g, 9.1 mmol) was dissolved in ethyl acetate (20 ml) and cooled to 0° C. This solution was then saturated with hydrogen chloride gas. After 1.5 h, the resulting precipitate (which was shown to be the undesired diastereoisomer, R$_f$=0.04 ethyl acetate), was removed by filtration and the filtrate evaporated. The solid residue was partitioned between ethyl acetate (25 ml) and 10% sodium carbonate solution (20 ml). The organic phase was separated and the aqueous extracted with ethyl acetate (2×25 ml). The combined organic phases were dried (Na$_2$SO$_4$) and evaporated in vacuo. The residue was chromatographed on silica gel using a gradient elution of 0–20% methanol in ethyl acetate to afford the title compound (1.66 g, 44%, R$_f$=0.13 ethyl acetate) as a pale yellow solid. mp 100°–103° C. $^1$H NMR (360 MHz, CDCl$_3$) δ 1.00–1.39 (4H, m), 1.50–1.72 (4H, m), 1.84–1.92 (1H, m), 2.00–2.07 (1H, m), 2.72–2.84 (2H, m), 3.28 (1H, dd, J=13.8 and 4.0 Hz), 3.40 (3H, s), 3.69 (1H, dd, J=9.8 and 4.1 Hz), 5.36 (1H, d, J=8.3 Hz), 7.21–7.36 (7H, m), 7.47–7.58 (2H, m), 8.66 (1H, d, J=8.3 Hz). [α]$_D^{23}$ +32.7° (c=0.58, CH$_3$OH).

The undesired diastereoisomer (Rf 0.04, ethyl acetate) could be epimerised to 3(R,S)-(2(R)-amino-3-phenylpropionylamino)-5cyclohexyl-1,3-dihydro-1-methyl-2H-1,4-benzodiazepin-2-one using the following procedure:

The undesired diastereoisomer (Rf 0.04, ethyl acetate) (18.6 g, 0.044mol) was dissolved in anhydrous ether (200 ml), and potassium-tert-butoxide (0.68 g, 6.1 mmol)was added. The mixture was stirred at room temperature for 1 h, then more potassium-tert-butoxide (0.68 g, 6.1 mmol) was added and the mixture heated at reflux for 5 h. The mixture was then cooled to ambient temperature, the solvent removed under vacuum, and the residue partitioned between ethyl acetate (200 ml) and water (200 ml). The organic layer was separated, dried (MgSO$_4$), filtered and evaporated in vacuo to afford the epimerised material.

Step 4:
(+)-N-[1(R)-2-[(3(R)-5-Cyclohexyl-2,3-dihydro-1-methyl-2-oxo-1H-1,4-benzodiazepin-3-yl)amino]-2-oxo-1-(phenylmethyl)ethyl]N'-phenyl thiourea A solution of (+)-3(R)-(2(R)- amino-3-phenylpropionylamino)-5 -cyclohexyl-1,3-dihydro-1-methyl-2H-1,4-benzodiazepin-2-one (1.6 g, 3.83 mmol) in anhydrous dichloromethane (10 ml) was treated with phenyl isothiocyanate (0.5 ml, 4.21 mmol), and then heated on the steam bath for 30 min. The solvent was evaporated in vacuo and the residue was chromatographed on silica gel with 1:1, ethyl acetate:petrol as the eluant, to afford the product (2.1 g, 100%) as a pale yellow solid. mp 129°–132° C. $^1$H NMR (360 MHz, CDCl$_3$) δ 0.95–1.07 (1H, m), 1.15–1.37 (3H, m), 1.45–1.69 (4H, m), 1.81–1.88 (1H, m), 1.93–2.00 (1H, m), 2.70–2.80 (1H, m), 3.24–3.41 (2H, m), 3.38 (3H, s), 5.23 (1H, d, J=7.3 Hz), 5.31–5.40 (1H, m), 6.67 (1H, 7.0 Hz), 6.87–7.02 (2H, m), 7.20–7.35 (9H, m), 7.46–7.52 (2H, m), 7.65 (1H, s). [α]$^{25}_D$ +27.3° (c=0.31, CH$_2$Cl$_2$).

Step 5:
(−)-N-[3(R)-5-Cyclohexyl-2,3-dihydro-1-methyl-2-oxo-1H-1,4-benzodiazepin-3-yl]N'-[3-(phenylsulphonylaminocarbonyl)phenyl]urea (+)-N-[1(R)-2-[(3(R)-5-Cyclohexyl-2,3-dihydro-1-methyl-2-oxo-1H-1,4-benzodiazepin-3-yl)amino]-2-oxo-1-(phenylmethyl)ethyl]N'-phenyl thiourea (1 g, 1.8 mmol) was dissolved in trifluoroacetic acid (10 ml) and heated to 55° C. for 15 min. The trifluoroacetic acid was removed under reduced pressure and the residue azeotroped with dichloromethane (2×10 ml) and toluene (2×10 ml). The residue was chromatographed on silica gel using 90:10:0.1:0.1, dichloromethane:methanol:acetic acid:water as the eluant to afford an orange gum. This was dissolved in ethyl acetate (40 ml), cooled to 0° C., and treated with 10% sodium carbonate solution (3 ml). After stirring for 1 min, the organic layer was separated and the aqueous re-extracted with ethyl acetate (2×20 ml). The combined organics were dried (Na$_2$SO$_4$) and evaporated in vacuo to afford an orange solid. This was assumed to be the amine and was used without further purification.

1-(Phenylsulphonylaminocarbonyl)-3-aminobenzene (297 mg, 1.08 mmol) was dissolved in anhydrous tetrahydrofuran (25 ml) and cooled to 0° C. under an atmosphere of nitrogen. Triphosgene (106 mg, 0.36 mmol) was added in one portion and the mixture was stirred for 2 min. The mixture was then treated with triethylamine (0.45 ml, 3.23 mmol) in portions of 129, 129, 64, 64 and 64 μl over a period of 5 min. The mixture was allowed to warm to 15° C. over a period of 10 min and was then re-cooled to 0° C. The amine (0.2 g, 0.74 mmol, prepared as described above) was dissolved in anhydrous tetrahydrofuran (5 ml) and added to the reaction dropwise. The mixture was stirred at 0° C. for 5 min and then stirred at ambient temperature for 40 min. The precipitated solid was removed by filtration and washed with tetrahydrofuran. The filtrate was evaporated and partitioned between ethyl acetate (200 ml) and 10% citric acid solution (40 ml). The organic phase was separated and washed with more 10% citric acid solution (40 ml) and brine (40 ml), and dried (Na$_2$SO$_4$). The solvent was evaporated in vacuo and the residue was chromatographed on silica gel using a gradient elution of 5–10% methanol in dichloromethane to afford the product (0.42 g, 99%) as a colourless solid.

This was dissolved in tetrahydrofuran (40 mg/ml) and 150 μl of solution was injected onto a dinitrobenzoyl leucine column (250×8.0 mm id., 5 μm) per run, using 10% methanol in dichloromethane plus 0.4% acetic acid as the mobile phase. Using a flow rate of 4 ml/min and UV detection at 300 nm, the fractions containing the single enantiomer were combined and evaporated in vacuo to afford the product (0.23 g, 55%) as a colourless solid with >99.5% ee. mp 180° C. (dec.). $^1$H NMR (360 MHz, D$_6$-DMSO) δ 0.85–0.98 (1H, m), 1.08–1.39 (3H, m), 1.41–1.66 (4H, m), 1.75–1.82 (1H, m), 1.87–1.93 (1H, m), 2.90–2.98 (1H, m), 3.32 (3H, s), 5.06 (1H, d, J=8.3 Hz), 7.29–7.35 (2H, m), 7.37–7.41 (2H, m), 7.49–7.56 (2H, m), 7.60–7.64 (3H, m), 7.68–7.76 (2H, m), 7.84 (1H, s), 7.96–7.99 (2H, m), 9.17 (1H, s), 12.50 (1H, brs). [α]$^{25}_D$ −7.9° (c=0.61, CH$_3$OH).

EXAMPLE 28

N-[3(R,S)-5-Cyclohexyl-2,3-dihydro-1-methyl-2oxo-1H-1,4-benzodiazepin-3-yl]N'-[3-(2-methyltetrazol-5-yl)phenyl]urea Step 1: 1-Methyl-5-(3-nitrophenyl)tetrazole and 2-methyl-5-(3-nitrophenyl)tetrazole Sodium hydroxide (1.22 g, 0.030 mol) in water (20 ml) was added to a stirred solution of 5-(3nitrophenyl)tetrazole (5.28 g, 0.028 mol) in ethanol (60 ml). Iodomethane (1.9 ml, 0.030 mol) was added and the reaction mixture was stirred at room temperature for 7 h. Further iodomethane (1.9 ml, 0.030 mol) was added and the reaction mixture was stirred for a further 18 h. The mixture was evaporated to dryness and the residue partitioned between ethyl acetate (100 ml) and water (50 ml). The organic layer was separated and the aqueous re-extracted with ethyl acetate (2×100 ml). The combined organic layers were dried (Na$_2$SO$_4$) then evaporated to give a brown solid which was purified by column chromatography on silica gel using dichloromethane:methanol (10:1) to first afford 2-methyl-5-(3-nitrophenyl)tetrazole (3.85 g, 67%) as a cream solid. mp 105° C. R$_f$ 0,78 in dichloromethane:diethyl ether (5:1) on silica plates. $^1$H NMR (360 MHz, CDCl$_3$) δ 4.45 (3H, s), 7.70 (1H, dd, J=8 and 8 Hz), 8.33 (1H, ddd, J=8, 2 and 2 Hz), 8.49 (1H, brd, J=8 Hz), 8.99 (1H, dd, J=2 and 2 Hz). Found: C, 47.12; H, 3.49; N, 34.05. C$_8$H$_7$N$_5$O$_2$ requires C, 46.83; H, 3.44; N, 34.13%.

The second product to elute was 1-methyl-5-(3nitrophenyl)tetrazole (345 mg, 6%) as a cream solid, mp 143°–144° C. R$_f$ 0.60 in dichloromethane:diethyl ether (5:1) on silica plates. $^1$H NMR (360 MHz, CDCl$_3$) δ 4.28 (3H, s), 7.82 (1H, dd, J=8 and 8 Hz), 8.18 (1H, ddd, J=8, 2 and 2 Hz), 8.47 (1H, brd, J=8 Hz), 8.64 (1H, dd, J=2 and 2 Hz). Found: C, 46.96; H, 3.40; N, 34.00. C$_8$H$_7$N$_5$O$_2$ requires C, 46.83; H, 3.44; N, 34.13%.

Step 2: 5-(3-Aminophenyl)-2-methyltetrazole

2-Methyl-5-(3-nitrophenyl)tetrazole (2.30 g, 0.0112 mol) was hydrogenated at 20 psi in ethanol (50 ml) using 10% palladium on carbon (230 mg) for 15 min. The mixture was filtered then evaporated to dryness in vacuo to give the title compound (1.55 g, 79%) as a colourless solid. mp 97° C. R$_f$ 0.40 in dichloromethane:methanol (5:1) on silica plates. $^1$H NMR (360 MHz, CDCl$_3$) δ 3.80 (2H, brs), 4.38 (3H, s), 6.78 (1H, ddd, J=8, 2 and 2 Hz), 7.26 (1H, dd, J=8 and 8 Hz), 7.47 (1H, dd, J=2 and 2 Hz), 7.51 (1H, dd, J=8 and 2 Hz).

Step 3: N-[3(R,S)-5-Cyclohexyl-2,3-dihydro-1-methyl-2--oxo-1H-1,4-benzodiazepin-3-yl]N'-[3-(2-methyltetrazol-5-yl)phenyl]urea To a stirred solution of 5-cyclohexyl-1,3-dihydro-1-methyl-3(R,S)-[(4-nitrophenyloxycarbonyl)amino]-2H-1,4-benzodiazepin-2-one (150 mg, 0.34 mmol) [Example 11, Step 3], in anhydrous dimethylformamide (3 ml) was added triethylamine (48 μl, 0.34 mmol). After 5 min a solution of 5-(3-aminophenyl)-2methyltetrazole (65 mg, 0.37 mmol) in anhydrous dimethylformamide (3m]) was added, and the solution heated at 50° C. for 2 h. After this time the solution was cooled to ambient temperature and evaporated in vacuo. The residue was dissolved in ethyl acetate (5 ml) and on standing a solid precipitated. This was recrystallised from ethyl acetate to afford the urea (65 mg, 40%) as a colourless solid. mp 195°–196° C. $^1$H NMR (360 MHz, CDCl$_3$) δ 1.05–2.06 (10H, m), 2.79 (1H, m), 3.45 (3H, s), 4.36 (3H, s), 5.42 (1H, d, J=8 Hz), 6.75 (1H, d, J=8 Hz), 7.15–7.60 (7H, m), 7.77 (1H, d, J=8 Hz), 8.06 (1H, s).

EXAMPLE 29

N-[3(R,S)-5-Cyclopentyl-2,3-dihydro-1-ethyl-2-oxo-1H-1,4-benzodiazepin-3-yl]N'-(3-(methylsulphonylaminocarbonyl)phenyl]urea The title compound was prepared from 5-cyclopentyl-1,3-dihydro-1-ethyl-3(R,S)-[[(4-nitrophenyloxycarbonyl)amino]-2H-1,4-benzodiazepin-2-one and 1-(methylsulphonylaminocarbonyl)-3-aminobenzene [Example 16, Step 2] using the procedure described in Example 11, Step 4, to afford the product as a colourless powder. mp 210°–212° C., $^1$H NMR (360 MHz, D6-DMSO) δ 0.93 (3H, t, J=7 Hz), 1.00–1.20 (1H, m), 1.40–1.90 (6H, m), 2.00–2.20 (1H, m), 3.34 (3H, s), 3.40–3.60 (1H, m), 3.62–3.80 (1H, m), 4.20–4.40 (1H, m), 5.00–5.10 (1H, m), 7.30–7.85 (8H, m), 7.93 (1H, s), 9.21 (1H, s), 12.06 (1H, brs).

EXAMPLE 30

N-[3(R,S)-5-Cyclopentyl-2,3-dihydro-1-ethyl-2-oxo-1H-1,4-benzodiazepin-3-yl]N'-[3-(isopropylsulphonylaminocarbonyl)phenyl]urea The title compound was prepared from 5-cyclopentyl-1,3-dihydro-1-ethyl-3(R,S)-[(4-nitrophenyloxycarbonyl)amino]-2H1,4-benzodiazepin-2-one and 1-(isopropylsulphonylaminocarbonyl)-3-aminobenzene [Example 12; Step 3] using the procedure described in Example 11, Step 4, to afford the product as a colourless powder. mp 160°–162° C. $^1$H NMR (360 MHz, D6-DMSO) δ 0.92 (3H, t, J=8 Hz), 1.00–1.20 (1H, m), 1.30 (6H, d, J=7 Hz), 1.40–1.80 (6H, m), 2.00–2.20 (1H, m), 3.40–3.60 (1H, m), 3.62–3.85 (2H, m), 4.10–4.30 (1H, m), 5.05 (1H, d, J=7 Hz), 7.30–7.80 (8H, m), 7.92 (1H, s), 9.20 (1H, s), 11.9 1 (1H, brs).

EXAMPLE 31

N-[3(R,S)-5-Cyclohexyl-2,3-dihydro-1-methyl-2-oxo-1H-1,4-benzodiazepin-3-yl]N'-[3-(1,1-dimethylethylsulphonylaminocarbonyl)phenyl]urea

Step 1: 1,1-Dimethylethylsulphinic acid

Sulphur dioxide gas was bubbled through a solution of 1,1-dimethylethylmagnesium chloride (0.4 mol) in diethyl ether (400 ml) for 2 h, maintaining the internal temperature at 5° C. The mixture was then poured into cold (5° C.) saturated ammonium chloride solution (200 ml) and stirred vigorously at this temperature for 15 min. The mixture was filtered and the ethereal layer separated and dried (MgSO$_4$). The solvent was removed in vacuo to afford the title compound (15.7 g, 32%) as a colourless solid. $^1$H NMR (360 MHz, CDCl$_3$) δ 1.21 (9H, s). MS (CI, NH$_3$) 121 (M-1).

Step 2: 1,1-Dimethylethylsulphinyl chloride

Thionyl chloride (18.8 ml, 0.26 mol) was added dropwise to 1,1dimethylethylsulphinic acid (15.7 g, 0.13 mol)over a period of 20 min, at ambient temperature, under an atmosphere of nitrogen. The solution was stirred for a further 2 h then the excess thionyl chloride was removed in vacuo and the residue azeotroped with diethyl ether (2×200 ml). The residue was distilled under reduced pressure to afford the title compound (12.92 g, 72%) as a straw yellow oil. b.p. 75° C. at 6 mmHg. $^1$H NMR (360 MHz, CDCl$_3$) δ 1.41 (9H, s).

Step 3: 1,1-Dimethylethylsulphinamide

To a suspension of 1,1-dimethylethylsulphinyl chloride (2.5 g, 17.7 mmol) in water (10 ml) was added aqueous ammonia solution (30%, 100 ml) dropwise. This mixture was heated to 80° C. for 10 min, cooled and the solvent evaporated in vacuo. The residue was azeotroped with toluene (2×25 ml), then triturated with diethyl ether (100 ml), and the resultant precipitate removed by filtration. The filtrate was evaporated in vacuo and the residue was chromatographed on silica gel using a gradient elution of 50% to 100% of ethyl acetate in petrol followed by 10% methanol in ethyl acetate, to afford the title compound (1.42 g, 65%) as a colourless solid. mp 107°–109° C. $^1$H NMR (360 MHz, CDCl$_3$) δ 1.23 (9H, s), 3.67 (2H, brs).

Step 4: 1,1-Dimethylethylsulphonamide

To a refluxing solution of 1,1-dimethylethylsulphinamide (0.5 g, 4.1 mmol) in anhydrous acetone (25 ml) was added dropwise a saturated solution of potassium permanganate in acetone (40 ml) over a period of 1 h, until a purple colour persisted. The mixture was refluxed for a further 30 min and the precipitate was removed by hot filtration. The precipitate was washed well with further acetone and the filtrate evaporated in vacuo. The resultant yellow solid was triturated with petrol and the precipitate was collected by filtration to give the title compound (0.32 g, 57%) as a colourless solid. mp 160°–162° C. $^1$H NMR (360MHz, D6-DMSO) δ 1.27 (9H, s), 6.58 (2H, brs).

Step 5: 1-(1,1-Dimethylethylsulphonylaminocarbonyl)-3-nitrobenzene

To a mixture of 3-nitrobenzoic acid (0.37 g, 2.2 mmol), 1,1-dimethylethylsulphonamide (0.3 g, 2.2 mmol) and 4-dimethylaminopyridine (0.27 g, 2.2 mmol) in anhydrous dichloromethane (20 ml), under an atmosphere of nitrogen, was added. 1-[3-(dimethylamino)-propyl]-3-ethyl carbodiimide hydrochloride (0.42 g, 2.2 mmol). The mixture was stirred at ambient temperature for 22 h. The mixture was extracted with 1M NaOH (50 ml) and the separated aqueous phase acidified using 5M HCl. This was extracted with dichloromethane (5×20 ml), then the combined organic extracts were dried (Na$_2$SO$_4$) and evaporated to dryness. The residue was chromatographed on silica gel using 1% methanol in dichloromethane as the eluant. The title compound (0.53 g, 85%) was isolated as a colourless solid. mp 220° C. $^1$H NMR (360 MHz, D6-DMSO) δ 1.27 (9H, s), 6.59 (1H, brs), 7.65 (1H, t, J=7.9 Hz), 8.24–8.30 (1H, m), 8.34–8.38 (1H, m), 8.68–8.72 (1H, m).

Step 6:
1-(1,1-Dimethylethylsulphonylaminocarbonyl)-3-aminobenzene

In the same way as that described in Example 11, Step 2, using 1-(1,1-dimethylethylsulphonylaminocarbonyl)-3-nitrobenzene (0.36 g, 1.26 mmol), 10% palladium on carbon (0.1 g, 28% (w/w)) in water (2 ml) and ethanol (25 ml), the title compound (0.32 g, 99%) was afforded as a colourless solid. mp 150° C. (dec.). $^1$H NMR (360MHz, D6-DMSO) δ 1.30 (9H, s), 4.99 (2H, brs), 6.56–6.63 (1H, m), 6.97 (1H, t, J=7.7 Hz), 7.13–7.25 (2H, m).

Step 7:
N-[3(R,S)-5-Cyclohexyl-2,3-dihydro-1-methyl-2-oxo-1H-1,4-benzodiazepin-3-yl]N'-[3-(1,1-dimethylethylsulphonylaminocarbonyl)phenyl]urea The title compound was prepared in the same way as that described in Example 11, Step 4, using 5-cyclohexyl-1,3-dihydro-1-methyl- 3(R,S)-[(4-nitrophenyloxycarbonyl)amino]-2H-1,4-benzodiazepin-2-one (0.3 g, 0.69 mmol), triethylamine (96 μl, 0.69 mmol), dimethylformamide (6 ml) and 1-(1,1-dimethylethylsulphonylaminocarbonyl)-3-aminobenzene (0.19 g, 0.76 mmol). The product (176 mg, 46%) was afforded as a colourless solid after recrystallisation from ethanol. mp 180° C. (dec.). $^1$H NMR (360 MHz, D6-DMSO) δ 0.84–0.98 (1H, m), 1.38 (9H, s), 1.08–1.65 (7H, m), 1.71–1.81 (1H, m), 1.86–1.94 (1H, m), 2.88–2.98 (1H, m), 3.32 (3H, s), 5.08 (1H, d, J=8.3 Hz), 7.29–7.42 (4H, m), 7.54 (1H, s), 7.56 (1H, s), 7.64 (1H, t, J=7.7 Hz), 7.75 (1H, d, J=7.9 Hz), 7.84 (1H, s), 9.19 (1H, s), 11.51 (1H, brs).

EXAMPLE 32

N-[3(R,S)-5-Cyclohexyl-2,3-dihydro-1-methyl-2-oxo-1H-1,4-benzodiazepin-3-yl]N'-[3-(1,1-dimethylethylcarbonylaminosulphonyl)phenyl]urea Step 1:
1-(1,1-Dimethylethylcarbonylaminosulphonyl)-3-nitrobenzene:

To a mixture of trimethylacetic acid (5.55 g, 54 mmol), 3-nitrobenzenesulphonamide (11 g, 54 mmol) and 4-dimethylaminopyridine (6.65 g, 54 mmol) in anhydrous dichloromethane (400 ml), under an atmosphere of nitrogen, was added 1-[3-(dimethylamino)propyl]-3-ethyl carbodiimide hydrochloride (10.43 g, 54 mmol). The mixture was stirred at ambient temperature for 24 h. The mixture was extracted with 1M NaOH (50 ml) and the separated aqueous phase was mixed with dichloromethane (200 ml) and acidified with 5M HCl. The two layers were separated and the aqueous phase was further extracted with dichloromethane (2×100 ml). The combined organic phases were dried (Na$_2$SO$_4$) and evaporated to dryness. The resultant solid was recrystallised from methanol to afford the title compound (9 g, 58%) as a colourless solid. mp 178°–81° C. $^1$H NMR (360 MHz, D6-DMSO) δ 1.07 (9H, s), 7.95 (1H, t, J=8.0 Hz), 8.30–8.34 (1H, m), 8.52–8.56 (1H, m), 8.57–8.60 (1H, m), 12.02 (1H, brs).

Step 2:
1-(1,1-Dimethylethylcarbonylaminosulphonyl)-3-aminobenzene

In the same way as that described in Example 11, Step 2, using 1-(1,1-dimethylethylcarbonylaminosulphonyl)-3-nitrobenzene (5 g, 17.5 mmol), 10% palladium on carbon (0.5 g, 10% (w/w)) in water (4 ml) and ethanol (100 ml), the title compound (3.36 g, 75%) was afforded as a pale yellow solid after recrystallisation from ethanol. mp 147°–150° C. $^1$H NMR (360 MHz, D6-DMSO) δ 1.07 (9H, s), 5.62 (2H, brs), 6.78 (1H, dd, J=8.0 and 2.0 Hz), 6.94 (1H, d, J=8.0 Hz), 7.08 (1H, t, J=2.0 Hz), 7.19 (1H, t, J=7.9 Hz), 11.47 (1H, brs).

Step 3:
N-[3(R,S)-5-Cyclohexyl-2,3-dihydro-1-methyl2-oxo-1H-1,4-benzodiazepin-3-yl]N'-[3-(1,1-dimethylethylcarbonylaminosulphonyl)phenyl]urea The title compound was prepared in the same way as that described in Example 11, Step 4, using 5-cyclohexyl-1,3-dihydro-1-methyl3(R,S)-[(4-nitrophenyloxycarbonyl)amino]-2H-1,4-benzodiazepin-2-one (0.3 g, 0.69 mmol), triethylamine (96 μl, 0.69 mmol), dimethylformamide (6 ml) and 1-(1,1-dimethylethylcarbonylaminosulphonyl)-3-aminobenzene (194 mg, 0.76 mmol). After trituration with hot methanol, the title compound (0.15 g, 39%) was afforded as a colourless solid. mp 235° C. (dec.). $^1$H NMR (360 MHz, D6-DMSO) δ 3 0.84–0.98 (1H, m), 1.04(9H, s), 1.06–1.40 (4H, m), 1.41–1.68 (3H, m), 1.73–1.82 (1H, m), 1.88–1.96 (1H, m), 2.89–3.00 (1H, m), 3.33 (3H, s), 5.06 (1H, d, J=8.3 Hz), 7.32–7.50 (4H, m), 7.52–7.58 (2H, m), 7.64 (1H, t, J=7.0 Hz), 7.75 (1H, d, J=7.9 Hz), 8.03 (1H, s), 9.39 (1H, s), 11.62 (1H, brs).

EXAMPLE 33

N-[3(R)-5-Cyclohexyl-2,3-dihydro-1-methyl-2-1H-1,4-benzodiazepin-3-yl]N'-[3-(2-methylphenylsulphonylaminocarbonyl)phenyl]urea Step 1:
1-(2-Methylsulphonylaminocarbonyl)-3-nitrobenzene To a mixture of 3-nitrobenzoic acid (5 g, 30 mmol), 2-methylphenylsulphonamide (5.13 g, 30 mmol) and 4-dimethylaminopyridine (3.65 g, 30 mmol) in anhydrous dichloromethane (200 ml), under an atmosphere of nitrogen, was added 1-[3-(dimethylamino)propyl]-3-ethyl carbodiimide hydrochloride (5.74 g, 30 mmol). The mixture was stirred at ambient temperature for 4 h. The resultant precipitate was collected by filtration and partitioned between dichloromethane (1×500 ml, 2×100 ml) and 1M HCl (250 ml). The combined organic phases were dried (MgSO$_4$) and evaporated to dryness to afford the title compound (6.4 g, 67%) as a colourless solid. mp 197°–199° C. $^1$H NMR (360 MHz, D6-DMSO) δ 3 2.63 (3H, s), 7.40–7.50 (2H, m), 7.61 (1H, td, J=10.7 and 2.1 Hz), 7.79 (1H, t, J=11.4 Hz), 8.07 (1H, dd, J=11.4 and 2.0 Hz), 8.27–8.31 (1H, m), 8.44–8.48 (1H, m), 8.74–8.78 (1H, m).

Step 2:
1-(2-Methylphenylsulphonylaminocarbonyl)-3-aminobenzene

In the same way as that described in Example 11, Step 2, using 1-(2-methylphenylsulphonylaminocarbonyl)-3-nitrobenzene (3 g, 9.4 mmol), 10% palladium on carbon (0.3 g, 10% (w/w)) in water (2 ml) and ethanol (60 ml), the title compound was afforded as a yellow solid. This was recrystallised from ethanol to give a pale yellow crystalline solid (2.21 g, 8.1%). mp 150°–152° C. $^1$H NMR (360 MHz, D6-DMSO) δ 2.61(3H, s), 6.78 (1H, d, J=7.8 Hz), 6.97–7.03 (2H, m), 7.12 (1H, t, J=7.8 Hz), 7.39–7.47 (2H, m), 7.58 (1H, t, J=7.5 Hz), 8.02 (1H, d, J =7.9 Hz).

Step 3:
(+)3(R)-Amino-5-cyclohexyl-1,3-dihydro-1-methyl-2H-1,4-benzodiazepin-2-one N-[1(R)-2-[(3(R)-5-Cyclohexyl-2,3-dihydro-1-methyl-2-oxo-1H-1,4-benzodiazepin-3-yl)amino]-2-oxo-1-(phenylmethyl)ethyl]N'-phenyl thiourea (4.5 g, 8.1 mmol) [Example 27, Step 4] was dissolved in trifluoroacetic acid (25 ml) and stirred at ambient temperature for 30 min. The trifluoroacetic acid was removed under reduced pressure and the residue azeotroped with dichloromethane (2×20 ml) and toluene (2×20 ml). The residue was chromatographed on silica gel using 90:10:0.1:0.1, dichloromethane:methanol:acetic acid:-water as the eluant, to afford an orange gum. This was dissolved in ethyl acetate (150 ml), cooled to 0° C., and treated with 10% sodium carbonate solution (15 ml). After diluting with water (25 ml) and stirring for 1 min, the organic layer was separated and the aqueous re-extracted with ethyl acetate (2 ×50 ml). The combined organics were dried (Na$_2$SO$_4$) and evaporated in vacuo to afford the title compound (1.56 g, 71%) as a pink solid with 99% e.e. mp 133°–136° C. $^1$H NMR (360 MHz, CDCl$_3$) δ 1.01–1.39 (4H, m), 1.50–1.54 (1H, m), 1.60–1.70 (3H, m), 1.84–1.92 (1H, m), 1.96–2.04 (1H, m), 2.36 (2H, brs), 2.70–2.80 (1H, m), 3.41 (3H, s), 4.32 (1H, s), 7.22–7.28 (2H, m), 7.46–7.58 (2H, m). [α]$_D$ +33.2° (c=0.66, CH$_3$OH).

Step 4:
N-[3(R)-5-Cyclohexyl-2,3-dihydro-1-methyl-2-oxo-1H-1,4-benzodiazepin-3-yl]N'-[3-(2-methylphenylsulphonylaminocarbonyl)phenyl]urea 1-(2Methylphenylsulphonylaminocarbonyl)phenyl]-3-aminobenzene (234 mg, 0.8 mmol) was dissolved in anhydrous tetrahydrofuran (20 ml) and cooled to 0° C. under an atmosphere of nitrogen. Triphosgene (0.08 g, 0.27 mmol) was added in one portion and the mixture was stirred for 2 min. The mixture was then treated with triethylamine (0.34 ml, 2.4 mmol) in portions of 98, 98, 49, 49 and 49 μl over a period of 5 min. The mixture was allowed to warm to 12° C. over a period of 10 min and was then re-cooled to 0° C. 3(R)-Amino-5-cyclohexyl-1,3-dihydro-1-methyl-2H-1,4-benzodiazepin-2-one (0.15 g, 0.55 mmol) was dissolved in anhydrous tetrahydrofuran (5 ml) and added to the reaction dropwise. The mixture was stirred at 0° C. for 5 min and then stirred at ambient temperature for 15 min. The precipitated solid was removed by filtration and washed with tetrahydrofuran. The filtrate was evaporated and partitioned between ethyl acetate (150 ml) and 10% citric acid solution (30 ml), brine (30 ml) and then dried (Na$_2$SO$_4$). The solvent was 25 evaporated in vacuo and the residue chromatographed on silica gel using a gradient elution of 5–10% methanol in dichloromethane. The resultant solid was recrystallised from ethanol to afford the title compound (0.17 g, 52%) as a colourless solid with >99% e.e. mp 175° C. (dec.). $^1$H NMR (360 MHz, D6-DMSO) δ 5 0.84–0.97 (1H, m), 1.06–1.66 (7H, m), 1.72–1.82 (1H, m), 1.86–1.96 (1H, m), 2.59 (3H, s), 2.88–2.98 (1H, m), 3.32 (3H, s), 5.06 (1H, d, J=8.3 Hz), 7.28–7.46 (6H, m), 7.50–7.57 (3H, m), 7.63 (1H, t, J=8.4 Hz), 7.75 (1H, d, J=6.5 Hz), 7.81 (1H, s), 7.99 (1H, d, J=7.7 Hz), 9.15 (1H, s), 12.60 (1H, brs). [α]$_D$ −9.3° (c=0.57, CH$_3$OH).

EXAMPLE 34
N-[3(R)-5-Cyclohexyl-2,3-dihydro-1-methyl-2-oxo-1H-1,4-benzodiazepin-3-yl]N'[4-methyl-3-(methylsulphonylaminocarbonyl)phenyl]urea

Step 1:
2-Methyl-1-(methylsulphonylaminocarbonyl)-5-nitrobenzene

The title compound was prepared in the same way as that described in Example 11, Step 1, using 2-methyl-5-nitrobenzoic acid (5 g, 27.6 mmol), methyl sulphonamide (2.63 g, 27.6 mmol), 4-dimethylaminopyridine (3.37 g, 27.6 mmol), 1-[3-(dimethylamino)propyl]-3-ethyl carbodiimide hydrochloride (5.29 g, 27.6 mmol) and anhydrous dichloromethane (200 ml). The title compound (5.67 g, 79%) was afforded as a colourless solid. mp 180° C. (dec.). $^1$H NMR (360 MHz, D6-DMSO) δ 2.50 (3H, s), 3.42 (3H, s), 7.61 (1H, d, J=8.5 Hz), 8.28 (1H, dd, J=8.4 and 2.5 Hz), 8.36 (1H, d, J=2.5 Hz), 12.46 (1H, brs).

Step 2:
2-Methyl-1-(methylsulphonylaminocarbonyl)-5-aminobenzene

In the same way as that described in Example 11, Step 2, using 2-methyl-1-(methylsulphonylaminocarbonyl)-5-nitrobenzene (3 g, 11.6 mmol), 10% palladium on carbon (0.3 g, 10% (w/w)) in water (2 ml) and ethanol (100 ml), the title compound (2.1 g, 79%) was afforded as a pale yellow crystalline solid. mp 174°–176° C. $^1$H NMR (360 MHz, D6-DMSO) δ 2.17 (3H, s), 3.32 (3H, s), 6.61 (1H, dd, J=8.1 and 2.5 Hz), 6.67 (1H, d, J=2.4 Hz), 6.92 (1H, d, J=8.2 Hz).

Step 3:
N-[3(R)-5-Cyclohexyl-2,3-dihydro-1-methyl-2-oxo-1H-1,4-benzodiazepin-3-yl]N'-[4-methyl-3-methysulphonylaminocarbonyl)phenyl]urea The title compound was prepared in the same way as that described in Example 33, Step 4, using 2-methyl-1-(methylsulphonylaminocarbonyl)-5-aminobenzene (185 mg, 0.81 mmol), triphosgene (80 mg, 0.27 mmol), triethylamine (0.34 ml, 2.42 mmol), 3(R)-amino-5-cyclohexyl-1,3-dihydro-1-methyl-2H-1,4-benzodiazepin-2-one (0.15 g, 0.56 mmol) and tetrahydrofuran (25 ml). After recrystallisation from methanol, the title compound (135 mg, 46%) was afforded as a colourless solid with >99% e.e. mp 175° C. (dec.). $^1$H NMR (360 MHz, D6DMSO) δ 1.00–1.41 (4H, m), 1.51–1.71 (4H, m), 1.80–1.86 (1H, m), 1.96–2.04 (1H, m), 2.35 (3H, s), 2.79–2.88 (1H, m), 3.31 (3H, s), 3.40 (3H, s), 5.26 (1H, d, J=7.5 Hz), 7.08 (1H, d, J=8.3 Hz), 7.30–7.42 (4H, m), 7.54–7.65 (3H, m), 8.94 (1H, s), 11.86 (1H, s). [α]$_D$ −7.7° (c=0.44, CH$_3$OH).

EXAMPLE 35

N-[3(S)-5-Cyclohexyl-2,3-dihydro-1-methyl-2-oxo1H-1,4-benzodiazepin-3-yl]N'-[3-(phenylsulphonylaminocarbonyl)phenyl]urea

Step 1:

(−)-3(S)-(2-(R)-Amino-3-phenylpropionylamino)-5-cyclohexyl-1,3-dihydro-1-methyl-2H-1,4-benzodiazepin-2-one 3(R,S)-[2(R)-(tert-Butyloxycarbonyl)amino-3-phenylpropionylamino]- 5-cyclohexyl-1,3-dihydro-1-methyl-2H-1,4-benzodiazepin-2-one (12.7 g, 24.5 mmol) [Example 27, Step 2] was dissolved in ethyl acetate (20 ml) and cooled to 0° C. This solution was then saturated with hydrogen chloride gas. After 1.5 h the resulting precipitate was collected by filtration. After recrystallisation twice from ethanol, the precipitate was partitioned between ethyl acetate (50 ml) and 10% sodium carbonate solution (50 ml). The organic phase was separated and the aqueous extracted with further ethyl acetate (2×50 ml). The combined organic phases were dried (Na₂SO₄) and evaporated in vacuo to afford the title compound (2 g, 20%) as a pale yellow solid. mp 75°–78° C. ¹H NMR (360 MHz, CDCl₃) δ 1.03–1.41 (4H, m), 1.48–1.72 (4H, m), 1.82–1.92 (1H, m), 1.97–2.06 (1H, m), 2.70–2.84 (2H, m), 3.28–3.42 (4H, m), 3.76–3.82 (1H, m), 5.36 (1H, d, J=8.2 Hz), 7.21–7.33 (7H, m), 7.50 (1H, t, J=8.4 Hz), 7.56 (1H, d, J=8.1 Hz), 8.67–8.72 (1H, m). [α]$_D$ −13.5° (c=0.63, CH₃OH).

Step 2:

N-[1(R)-2[(3(S)-5-Cyclohexyl-2,3-dihydro-1-methyl-2-oxo-1H-1,4-benzodiazepin-3-yl)amino]-2-oxo-1-(phenylmethyl)ethyl]N'-phenyl thiourea In the same way as that described in Example 27, Step 4, using (−)-3(S)-(2(R)-amino-3phenylpropionylamino)-5-cyclohexyl-1,3-dihydro-1-methyl-2H-1,4-benzodiazepin-2-one (1.5 g, 3.6 mmol), phenyl isothiocyanate (0.47 ml, 4.0 mmol) and anhydrous dichloromethane (10 ml), the 25 title compound (1.95 g, 98%) was afforded as a colourless solid. mp 134°–137° C. ¹H NMR (360 MHz, CDCl₃) δ 1.00–1.12 (1H, m), 1.16–1.44 (3H, m), 1.48–1.78 (4H, m), 1.84–1.96 (1H, m), 2.00–2.08 (1H, m), 2.72–2.82 (1H, m), 3.29–3.44 (2H, m), 3.37 (3H, s), 5.26 (1H, d, J=7.6 Hz), 5.28–5.36 (1H, m), 6.79 (1H, d, J=7.8 Hz), 6.98–7.04 (2H, m), 7.15–7.42 (9H, m), 7.43–7.56 (2H, m), 7.62 (1H, s). [α]$_D^{23}$ −15.7° (c=0.70, CH₂Cl₂).

Step 3:

3(S)-Amino-5-cyclohexyl-1,3-dihydro-1-methyl-2H-1,4-benzodiazepin-2-one

In the same way as that described in Example 33, Step 3, using N-[1(R)-2-[(3(S)-5-cyclohexyl-2,3-dihydro-1-methyl-2-oxo-1H-1,4-benzodiazepin-3-yl)amino]-2-oxo-1-(phenylmethyl)ethyl]N'-phenyl thiourea (1.8 g, 3.3 mmol) and trifluoroacetic acid (10 ml), the title compound (0.8 g, 91%) was afforded as a pink solid with 98.4° e.e. mp 130°–133° C. ¹H NMR (360 MHz, CDCl₃) δ 1.01–1.39 (4H, m), 1.50–1.54 (1H, m), 1.60–1.72 (3H, m), 1.84–1.96 (1H, m), 1.97–2.02 (1H, m), 2.70 (2H, brs), 2.70–2.79 (1H, m), 3.39 (3H, s), 4.33 (1H, s), 7.22–7.28 (2H, m), 7.46–7.54 (2H, m). [α]$_D$ −33.2° (c=0.70, CH₃OH).

Step 4:

N-[3(S)-5-Cyclohexyl-2,3-dihydro-1-methyl-2-oxo-1H-1,4-benzodiazepin-3-yl]N'-]3-(phenylsulphonylaminocarbonyl)phenyl]urea The title compound was prepared in the same way as that described in Example 33, Step 4, using 1-(phenylsulphonylaminocarbonyl)-3-aminobenzene (0.30 g, 1.08 mmol) [Example 14, Step 2]), triphosgene (107 mg, 0.36 mmol), triethylamine (0.45 ml, 3.23 mmol), 3(S)-amino-5-cyclohexyl-1,3-dihydro-1-methyl-2H-1,4-benzodiazepin-2-one (0.2 g, 0.74 mmol) and tetrahydrofuran (30 ml). After trituration with diethyl ether, the title compound (248 mg, 59%) was afforded as a colourless solid with >99% e.e. mp 180° C. (dec.). ¹H NMR (360 MHz, D6-DMSO) δ 0.82–0.98 (1H, m), 1.08–1.65 (7H, m), 1.75–1.83 (1H, m), 1.88–1.96 (1H, m), 2.90–3.00 (1H, m), 3.31 (3H, s), 5.06 (1H, d, J=8.3 Hz), 7.30–7.36 (2H, m), 7.37–7.41 (2H, m), 7.49–7.56 (2H, m), 7.60–7.65 (3H, m), 7.68–7.76 (2H, m), 7.84 (1H, s), 7.96–7.99 (2H, m), 9.17 (1H, s), 12.46 (1H, brs). [α]$_D$ +9.4° (c=0.37, CH₃OH).

EXAMPLE 36

N-[3(R,S)-5-Cyclopentyl-2,3-dihydro-1-propyl-2-oxo-1H-1,4-benzodiazepin-3-yl]N'-[3-(isopropylsulphonylaminocarbonyl)phenyl]urea

Step 1:

5-Cyclopentyl-1,3-dihydro-1-propyl-3(R,S)-[-(benzyloxycarbonyl)amino]-2H-1,4-benzodiazepin-2-one To a solution of 5-cyclopentyl-1,3-dihydro-3(R,S)-[(benzyloxycarbonyl)amino]-2H-1,4-benzodiazepin-2-one [Example 5, Step 3] (1.48 g, 3.93 mmol) in anhydrous dimethylformamide (40 ml), cooled in an ice bath, was added sodium hydride (60% dispersion in oil, 173 mg, 4.33 mmol) and the resulting mixture stirred under nitrogen for 1 h. Iodopropane (0.46 ml, 4.72 mmol) was then added and the mixture stirred at room temperature for 3 h. The solvent was evaporated and the residue partitioned between dichloromethane (100 ml) and water (100 ml). The aqueous layer was re-extracted with more dichloromethane (100 ml), the organic extracts were combined, dried (MgSO₄) and evaporated. The residue was then triturated with ether to afford the title compound (1.36 g, 83%) as a white solid. mp 138°14 140° C. ¹H NMR (360 MHz, CDCl₃) δ 0.80 (3H, t, J=7.4 Hz), 1.26–1.79 (8H, m), 1.94 (1H, m), 2.12 (1H, m), 3.30 (1H, m), 3.55 (1H, m), 4.29 (1H, m), 5.10 (2H, m), 5.13 (1H, d), 6.52 (1H, d, J=8.1 Hz), 7.23–7.34 (5H, m), 7.48 (1H, t of d, J=8.0 and 1.4 Hz), 7.56 (1H, dd, J=7.8 and 1.4 Hz).

Step 2:

3(R,S)-Amino-5-cyclopentyl-1,3-dihydro-1-propyl-2H-1,4-benzodiazepin-2-one

To 5-cyclopentyl-1,3-dihydro-1-propyl-3(R,S)-[(benzyloxycarbonyl)amino]-2H-1,4-benzodiazepin-2-one (507 mg, 1.21 mmol) was added 45% hydrobromic acid in acetic acid (1 ml) and the mixture stirred at room temperature for 2 h. Anhydrous ether (10 ml) was then added and the mixture was stirred for 1.5 h before removing the solvent by pipette. The resulting solid was washed with more ether, filtered off and washed again with ether, before partitioning between dichloromethane (30 ml) and 2N sodium hydroxide solution (30 ml). The aqueous layer was re-extracted with more dichloromethane (2×30 ml), the organic extracts combined, dried (Na₂SO₄) and evaporated to leave the title compound (333 mg, 96%) as a colourless oil. $^1$H NMR (360 MHz, CDCl$_3$) δ 0.81 (3H, t, J=7.4 Hz), 1.25–1.94 (9H, m); 2.16 (1H, m), 3.29 (1H, m), 3.56 (1H, m), 4.28 (1H, s), 4.30 (1H, m), 7.24 (1H, t, J=7.3 Hz), 7.31 (1H, d, J=7.9 Hz), 7.46 (1H, t of d, J=7.8 and 1.5 Hz), 7.53 (1H, dd, J=7.8 and 1.4 Hz).

Step 3:
5-Cyclopentyl-1,3-dihydro-1-propyl-3(R,S)-[(4-nitrophenyloxycarbonyl)amino]-2H-1,4-benzodiazepin2-one The title compound was prepared from 3(R,S)-amino-5-cyclopentyl-1,3-dihydro-1-propyl-2H-1,4-benzodiazepin-2-one (321 mg, 11.2 mmol) and 4-nitrophenyl chloroformate (229 mg, 11.4 mmol) using the procedure described in Example 20, Step 1. The crude product was triturated with ether (10 ml) to give the title compound (396 mg, 78%) as a white solid. $^1$H NMR (360 MHz, CDCl$_3$) 0.83 (3H, t, J=7.4 Hz), 1.33–1.82 (8H, m), 1.97 (1H, m), 2.15 (1H, m), 3.34 (1H, m), 3.60 (1H, m), 4.32 (1H, m), 5.16 (1H, d, J=8.3 Hz), 6.89 (1H, d, J=8.4 Hz), 7.30–7.37 (4H, m), 7.52 (1H, t of d, J=7.8 and 1.6 Hz), 7.59 (1H, dd, J=7.8 and 1.5 Hz), 8.22 (2H, d, J=9.2 Hz).

Step 4:
N-[3(R,S)-5-Cyclopentyl-2,3-dihydro-1-propyl-2-oxo-1H-1,4-benzodiazepin-3-yl]N'-[3-(isopropylsulphonylaminocarbonyl)phenyl]urea The title compound was prepared from 5-cyclopentyl-1,3-dihydro-1-propyl-3(R,S)-[(4-nitrophenyloxycarbonyl)amino]-2H-1,4-benzodiazepin-2-one (254 mg, 0.56 mmol) and 1-(isopropylsulphonylaminocarbonyl)-3-aminobenzene [Example 12, Step 3] (137 mg, 0.56 mmol) using the procedure described in Example 11, Step 4, to afford the title compound (162 mg, 52%) as a white solid. mp 159°–162° C. (MeOH). $^1$H NMR (360 MHz, D6-DMSO) δ 0.72 (3H, t, J=7.3 Hz), 1.10–1.31 (9H, m), 1.49–1.63 (4H, m), 1.71 (1H, m), 1.82 (1H, m), 2.04 (1H, m), 3.51 (1H, m), 3.68 (1H, m), 3.79 (1H, m), 4.22 (1H, m), 5.06 (1H, d, J=8.3 Hz), 7.33–7.41 (3H, m), 7.46 (1H, d, J=7.8 Hz), 7.55 (1H, d, J=7.9 Hz), 7.63–7.64 (2H, m), 7.79 (1H, d, J=7.8 Hz), 7.92 (1H, s), 9.19 (1H, s), 11.93 (1H, s).

EXAMPLE 37
N-[3(R,S)-5-Cyclopentyl-2,3-dihydro-1propyl-2-oxo-1H-1,4-benzodiazepin-3-yl]N'[-3-(1,1-dimethylethylsulphonylaminocarbonyl)phenyl]urea This compound was prepared from 5-cyclopentyl-1,3-dihydro-1-propyl-3(R,S)-[(4-nitrophenyloxycarbonyl)amino]-2H-1,4-benzodiazepin-2-one [Example 36, Step 3] (136 mg, 0.3 mmol) and 1-(1,1-dimethylethylsulphonylaminocarbonyl)-3aminobenzene [Example 31, Step 6] (79 mg, 0.31 mmol) using the procedure described in Example 11, Step 4, with a heating time of 18 h to afford the title compound (64 mg, 37%) as a white solid. mp 160°–166° C. (MeOH/H$_2$O). $^1$H NMR (360 MHz, D6-DMSO) δ 0.72 (3H, t, J=7.3Hz), 1.16–1.38 (3H, m), 1.38 (9H, s), 1.50–1.61 (4H, m), 1.70 (1H, m), 1.82 (1H, m), 2.03 (1H, m), 3.51 (1H, m), 3.68 (1H, m), 4.20 (1H, m), 5.06 (1H, d, J=8.4Hz), 7.34–7.40 (4H, m), 7.54 (1H, d, J=8.1 Hz), 7.63 (2H, m), 7.78 (1H, d, J=8.2 Hz), 7.84 (1H, s), 9.18 (1H, s), 11.51 (1H, s).

EXAMPLE 38
N-[3(R,S)-5-Cyclopentyl-2,3-dihydro-1-methyl2-oxo-1H-1,4-benzodiazepin-3-yl]N'-[3-(isopropylsulphonylaminocarbonyl)phenyl]urea A solution of 5-cyclopentyl-1,3-dihydro-1-methyl-3(R,S)-[(4-nitrophenyloxycarbonyl)amino]-2H-1,4-benzodiazepin-2-one (155 mg, 0.37 mmol) in anhydrous dimethylformamide (4 ml), under an atmosphere of nitrogen, at ambient temperature was treated with triethylamine (60 μl, 0.43 mmol). After stirring at ambient temperature for 5 min. 1-(isopropylsulphonylaminocarbonyl)-3-aminobenzene was added in one portion. The yellow solution was heated at 60° C. for 2 h. The solution was cooled and the solvent evaporated in vacuo. The residue was partitioned between ethyl acetate (20 ml) and 20% aqueous acetic acid (5 ml). The organic phase was collected and the aqueous phase extracted with ethyl acetate (2×20 ml). The combined organic layers were dried (MgSO$_4$) and evaporated in vacuo. The residue was azeotroped with toluene (20 ml) and triturated with diethyl ether to give a cream solid. This was recrystallised from methanol to give the title compound (87 mg, 45%) as a white solid. mp 169°–170° C. (dec.). $^1$H NMR (360 MHz, CDCl$_3$) δ 1.20–2.20 (9H, m), 1.43 (6H, dd, J=6.8 and 1Hz), 3.37 (1H, m), 3.48 (3H, s), 3.93 (1H, septet, J=6.8 Hz), 5.44 (1H, d, J=7.5 Hz), 7.10–7.70 (8H, m), 8.27 (1H, s).

EXAMPLE 39
N-[3(R,S)-5-Cyclopentyl-2,3-dihydro-1-methyl-2-oxo-1H-1,4-benzodiazepin-3-yl]N'-[3-(1,1-dimethylethylsulphonylaminocarbonyl)phenyl urea Step 1:
5-Cyclopentyl-1,3-dihydro-1-methyl-3(R,S)-[(benzyloxycarbonyl)amino]2H-1,4-benzodiazepine-2-one To a solution of 5-cyclopentyl-1,3-dihydro-3(R,S)-[(benzyloxycarbonyl)amino]-2H-1,4-benzodiazepin-2-one (1.47 g, 3.91 mmol) in anhydrous dimethylformamide (40 ml) under nitrogen, cooled in an ice bath, was added sodium hydride (55% dispersion in oil, 178 mg, 4.08 mmol) in portions and the resulting mixture stirred for lb. Iodomethane (0.26 ml, 4.1 mmol) was then added and the mixture stirred for 30 min. The solvent was evaporated and the residue partitioned between dichloromethane (20 ml) and water (20 ml). The aqueous layer was re-extracted with dichloromethane (20 ml), the organic extracts were combined, dried (MgSO$_4$), and evaporated. The residue was triturated with diethyl ether to afford the title compound (1.19 g, 78%) as a white solid. $^1$H NMR (360 MHz, CDCl$_3$) δ 1.26 (1H, m), 1.46–2.00 (6H, m), 2.00–2.20 (1H, m), 3.30 (1H, m), 3.40 (3H, s), 5.08 (2H, d, J=1.4 Hz), 5.15 (1H, d, J=8 Hz.), 6.50 (1H, d, J=8 Hz), 7.24–7.62 (9H, m).

Step 2:
3(R,S)-Amino-5-cyclopentyl-1,3-dihydro-1-methyl-2H-1,4-benzodiazepin-2-one To 5-cyclopentyl-1,3-dihydro-1-methyl-3(R,S)-[(benzyloxycarbonyl)amino]-2H-1,4-benzodiazepin-2-one (475 mg, 1.2 mmol) was added 45% hydrobromic acid in acetic acid (1 ml) and the mixture stirred at room temperature for 2 h. Anhydrous diethyl ether (50 ml) was added and the resultant cream coloured suspension stirred at 0° C. for 1 h. On settling, the solvent was decanted off, and the solid triturated in anhydrous diethyl ether. The resultant solid was collected by filtration and washed with more diethyl ether. The solid was partitioned between 10% Na₂CO₃ solution (25 ml) and ethyl acetate (20 ml), the aqueous layer was further extracted with ethyl acetate (4×10 ml) and the organic extracts combined, dried (MgSO₄), and evaporated to give the title compound (247 mg, 79%) as a colourless off.

Step 3:
N-[3-(R,S)-5-Cyclopentyl-2,3-dihydro-1-methyl-2-oxo-1H-1,4-benzodiazepin-3-yl]N'-3-(1,1-dimethylethylsulphonylaminocarbonyl)phenyl]urea To 1-(1,1-dimethylethylsulphonylaminocarbonyl)-3-aminobenzene (290 mg, 0.86 mmol) stirring in tetrahydrofuran (20 ml), under nitrogen at 0° C., was added triphosgene (78 mg, 0.26 mmol) in one portion. After 10 min triethylamine (230 mg, 2.27 mmol) was added dropwise as a solution in tetrahydrofuran (1 ml) over 5 min, and the resulting mixture stirred at room temperature for 20 min. On re-cooling the mixture to 0° C., 3(R,S)-amino-5-cyclopentyl-1,3-dihydro-1-methyl-2H-1,4-benzodiazepin-2-one (176 mg, 0.68 mmol) was added as a solution in tetrahydrofuran (9 ml) via cannula and the mixture stirred for 4 h at room temperature. The reaction mixture was filtered, the solid washed with tetrahydrofuran (2×20 ml) and the filtrate evaporated. The residue was partitioned between ethyl acetate (100 ml) and 10% citric add solution (20 ml) and the organic layer retained. The aqueous layer was extracted further with ethyl acetate (2×50 ml), the organic extracts were combined, dried (MgSO₄), concentrated, and the residue subjected to chromatography on silica gel (5:95-methanol:dichloromethane). The resulting solid was recrystallised twice from methanol-water to give a white solid (64 mg, 14%). mp 196°–197° C. (dec.). ¹H NMR (360 MHz, D6-DMSO) 1.06–1.12 (1H, m), 1.39 (9H, s), 1.49–1.65 (5H, m), 1.79–1.82 (1H, m), 2.00–2.03 (1H, m), 3.33 (3H, s), 3.49 (1H, m), 5.08 (1H, d, J=7.6 Hz), 7.35–7.42 (4H, m), 7.53–7.66 (3H, m), 7.76–7.79 (1H, m), 7.85 (1H, s), 9.19 (1H, s), 11.51 (1H, s). MS (CI, NH₃) 556 (M+NH₄+).

EXAMPLE 40

N-[3-(R,S)-5-Cyclopentyl-2,3-dihydro-1-methyl-2-oxo-1H-1,4-benzodiazepin-3-yl]N'-[3-(phenylsulphonylaminocarbonyl)phenyl]urea To 1-(phenylsulphonylaminocarbonyl)-3-aminobenzene (185 mg, 0.67 mmol), stirring in anhydrous tetrahydrofuran (25 ml) under nitrogen, at 0° C., was added triphosgene (65 mg, 0.22 mmol) in one portion. After 5 min triethylamine (0.26 ml, 1.87 mmol) was added slowly over 3 min and the cooling bath removed. The mixture was stirred at room temperature for 20 min, cooled to 0° C. and 3(R,S)-amino-5-cyclopentyl-1,3-dihydro-1-methyl-2H-1,4-benzodiazepin-2-one (150 mg, 0.58 mmol) in anhydrous tetrahydrofuran (5 ml) added dropwise over 5 min. The reaction mixture was stirred at 0° C. for 10 min and at room temperature for 1 h, before filtering to remove the white suspension. The solid was washed with tetrahydrofuran (2×10 ml) and the combined filtrates evaporated to give an oily residue. On partitioning between ethyl acetate (100 ml) and 10% citric acid solution (20 ml) the organic layer was retained and the aqueous layer re-extracted with ethyl acetate (2×20 ml). The organic layers were combined, dried (MgSO₄), and evaporated to give a cream coloured solid. Chromatography on silica gel, using a gradient elution (5:95-methanol:dichloromethane then 10:90 methanol:dichloromethane) gave a cream coloured solid which was recrystallised from methanol-water to give the title compound (40 mg, 12%) as a white solid. mp 187° C. (dec.). ¹H NMR (360 MHz, D6DMSO) 1.06 (1H, m), 1.50–1.66 (5H, m), 1.77 (1H, m), 1.81 (1H, m), 3.33 (3H, s), 3.48 (1H, m), 5.07 (1H, d, J= 7.7 Hz), 7.30–7.41 (4H, m), 7.49–7.69 (6H, m), 7.76–7.78 (1H, m), 7.85 (1H, s), 7.95–7.98 (2H, m), 9.15 (1H, s), 12.48 (1H, brs). MS (CI, NH₃) 559 (M+).

EXAMPLE 41

N-[3(R,S)-5-Cyclobutyl-2,3-dihydro-1-methyl-2-oxo-1H-1,4-benzodiazepin-3-yl]N'-[3-methylphenyl]urea Step 1: 2-Aminophenyl cyclobutyl methanone Over a period of 1 h a solution of cyclobutyl bromide (13 g, 0.1 mol) in diethyl ether (150 ml) was added dropwise to a slurry of magnesium turnings (2.5 g, 0.11 mol) and a crystal of iodine in diethyl ether (20 ml) at reflux. The mixture was stirred for a further hour whereupon the Grignard solution was cannulated into a pressure equalising dropping funnel, attached to a three-necked round-bottomed flask, which was under an atmosphere of nitrogen. A solution of 2-aminobenzonitrile (3.78 g, 32 mmol) at 0° C. in diethyl ether (50 ml) was treated dropwise with the Grignard reagent prepared above, over a period of 15 min. Once the addition was complete, the mixture was warmed to room temperature and stirred for 16 h under nitrogen. The solution was cooled to 0° C., quenched with 5N hydrochloric acid (20 ml), and basified using solid sodium hydroxide (4 g). The aqueous solution was extracted with ethyl acetate (2×100 ml) and the combined organic layers were dried (Na₂SO₄) and evaporated. The residue was chromatographed on silica gel using 2:1 petrol:ethyl acetate as the eluant. This gave a yellow oil which was then azeotroped with toluene (2×80 ml) to-give the title compound (4 g, 71%) as a pale yellow solid. mp 55° C. ¹H NMR (250 MHz, CDCl₃) 5 1.72–2.48 (6H, m), 3.80–4.00 (1H, m), 6.23 (2H, brs), 6.50–6.61 (2H, m), 7.11–7.22 (1H, m), 7.45–7.54 (1H, m).

Step 2:
5-Cyclobutyl-1,3-dihydro-3(R,S)-[(benzyloxycarbonyl)amino]-2H-1,4-benzodiazepin-2-one A solution of α-isopropylthio-N-benzyloxycarbonyl glycine (8.4 g, 29.7 mmol) in anhydrous dichloromethane (200 ml) was cooled to 0° C. N-methylmorpholine (3.3 ml, 29.7 mmol) was added over 2 min followed by isobutyl chloroformate (3.9 ml, 29.7 mmol). This mixture was stirred for 15 min at 0° C. whereupon the mixture was heated to reflux. 2-Aminophenyl cyclobutyl methanone (4 g, 22.9 mmol) in anhydrous dichloromethane (20 ml) was added dropwise at reflux to the reaction mixture over 10 min and the mixture stirred at reflux for a further 1.5 h. The reaction mixture was washed with 1N citric add (100 ml), water (100 ml), saturated sodium bicarbonate solution (100 ml) and brine (100 ml). The organic phase was dried (Na₂SO₄), evaporated and azeotroped with toluene (2×100 ml) to give a yellow oil. Trituration with 7:1 petrol:ethyl acetate afforded the product (8 g, 80%) as a colourless solid. This material was used without further purification.

A solution of anhydrous tetrahydrofuran (300 ml) was cooled to 0° C. and saturated with ammonia gas. To this solution was added the glycinamide (8 g, 18 mmol) prepared above, followed by mercuric chloride (7.4 g, 27 mmol). The mixture was stirred at 0° C. for 1.5 h with continuous bubbling of ammonia gas. The mixture was filtered through "hyflo" and the filtrate evaporated to afford the desired amine as a colourless waxy solid. The material was used without further purification.

The amine (6.9 g, 18 mmol) prepared above was dissolved in acetic acid (250 ml) and treated with ammonium acetate (6.5 g, 84.6 mmol). This mixture was stirred at room temperature for 16 h under nitrogen. The solvent was evaporated and the residue partitioned between ethyl acetate (250 ml) and 10% sodium hydroxide solution (100 ml). The organic layer was separated, dried ($Na_2SO_4$) and evaporated to give a yellow solid. Trituration with diethyl ether afforded the rifle compound (3.8 g, 50%) as a colourless solid. mp 200°–202° C. TLC (silica, petrol:ethyl acetate 2:1). Rf=0.3. $^1$H NMR (250 MHz, $CDCl_3$) δ 1.60–2.80 (6H, m), 3.70 (1H, m), 5.12 (2H, m), 5.22 (1H, d, J=8 Hz), 6.50 (1H, d, J=8 Hz), 7.02–7.53 (9H, m), 9.44 (1H, s).

Step 3:
5-Cyclobutyl-1,3-dihydro-3(R,S)-[(benzyloxycarbonyl)amino]-1-methyl-2H-1,4-benzodiazepin-3-one 5-Cyclobutyl-1,3-dihydro-3(R,S)-[(benzyloxycarbonyl)amino]-2H-1,4-benzodiazepin-2-one (1 g, 2.75 mmol) in anhydrous toluene (70 ml) was heated to reflux. A solution of dimethylformamide dimethyl acetal (1.75 ml, 13.7 mmol) in anhydrous toluene (10 ml) was added dropwise and the mixture was heated at reflux for a further 3 h. The solvent was evaporated and the residue triturated with diethyl ether to afford the title compound (0.75 g, 72%) as a colourless solid. mp 210°–211° C. $^1$H NMR (250 MHz, $CDCl_3$) δ 1.68–2.06 (4H, m), 2.20–2.60 (2H, m), 3.41 (3H, s), 3.60–3.80 (1H, m), 5.00–5.30 (3H, m), 6.51 (1H, d, J=14 Hz), 7.14–7.54 (9H, m).

Step 4:
3(R,S)-Amino-5-cyclobutyl-1,3-dihydro-1-methyl-2H-1,4-benzodiazepin-2-one 5-Cyclobutyl-1,3-dihydro-3(R,S)-[(benzyloxycarbonyl)amino]-1-methyl-2H-1,4-benzodiazepin-3-one (400 mg, 1.06 mmol) was treated with a solution of 45% hydrogen bromide in acetic acid (10 ml), and stirred for 20 min at room temperature. The mixture was then added dropwise onto cold (0° C.) diethyl ether (50 ml). A white solid was precipitated and filtered off. The solid was treated with 10% sodium hydroxide solution (50 ml), then extracted with ethyl acetate (80 ml). The organic layer was separated, dried ($Na_2SO_4$) and evaporated to give a yellow foam. This material was then used without further purification.

Step 5:
N-[3(R,S)-5-Cyclobutyl-2,3-dihydro-1-methyl-2-oxo-1H-1,4-benzodiazepin-3-yl]N'-[3-methylphenyl]urea A solution of 3(R,S)-amino-5-cyclobutyl-1,3-dihydro-1-methyl-2H-1,4-benzodiazepin-2-one (50 mg, 0.21 mmol) in anhydrous tetrahydrofuran (5 ml) under nitrogen was treated with 3-methylphenylisocyanate (27μl, 0.21 mmol). The mixture was stirred for 20 min at room temperature whereupon a solid o precipitated out of solution. The solid was collected by filtration and triturated with diethyl ether to afford the title compound (50 mg, 64%) as a colourless powder. mp 135°–137° C. $^1$H NMR (250 MHz, D6-DMSO) δ 5 1.60–2.00 (4H, m), 2.28 (3H, s), 2.30–2.45 (2H, m), 3.36 (3H, s), 3.80–4.00 (1H, m), 5.00–5.10 (1H, m), 6.60–7.70 (8H, m), 8.55 (1H, s), 8.90 (1H, s).

EXAMPLE 42
N-[3(R,S)-5-Cyclohexyl-2,3-dihydro-1-methyl-2-oxo-1H-1,4-benzodiazepin-3-yl]N'-[3(R,S)-(methylsulphinyl)phenyl urea Step 1:
N-tert-Butyloxycarbonyl-3-(methylmercapto)aniline To a solution of 3-(methylmercapto)aniline (5 ml, 40.5 mmol) in anhydrous dichloromethane (100 ml) was added di-tert-butyl dicarbonate (8.86 g, 40.5 mmol) and the resulting dark brown mixture stirred at room temperature for 64 h under a nitrogen atmosphere. Diethyl ether (200 ml) was then added and the organic phase was washed with 1N hydrochloric acid (1×25 ml), water (1×25 ml), brine (1×40 ml), dried ($MgSO_4$) and concentrated. Flash chromatography of the residue on silica gel (hexane:diethyl ether, 90:10) gave the title compound (8.45 g, 87%) as a white solid. $^1$H NMR (250 MHz, $CDCl_3$) δ 1.52 (9H, s), 2.47 (3H, s), 6.45 (1H, brs), 6.92 (1H, ddd, J=7.8, 1.9 and 1.2 Hz), 7.06 (1H, ddd, J=7.8, 1.9 and 1.2 Hz), 7.18 (1H, t, J=7.8 Hz), 7.36 (1H, t, J=1.9 Hz). MS (CI, $NH_3$) 239 (M+).

Step 2:
N-tert-Butyloxycarbonyl-3(R,S)-(methylsulphinyl)aniline:

To a solution of N-tert-butyloxycarbonyl-3-(methylmercapto)aniline (3.7 g, 15.5 mmol) and n-tetrabutylammonium bromide (1 g, 3.1 mmol) in dichloromethane (500 ml) was added a solution of ammonium cesium (IV) nitrate (17.8 g, 32.5 mmol) in water (90 ml). The resulting two-phase system was vigorously stirred at room temperature for 3 h before the organic phase was decanted off, washed with water (2×400 ml), dried ($Na_2SO_4$) and concentrated. Flash chromatography of the remaining brown oil on silica gel, using ethyl acetate as the eluant afforded the title compound (550 mg, 14%) as a brown-red glass. $^1$H NMR (250 MHz, $CDCl_3$) δ 1.54 (9H, s), 2.73 (3H, s), 6.79 (1H, brs), 7.27–7.32 (1H, m), 7.40–7.51 (2H, m), 7.72 (1H, brs). MS (CI, $NH_3$) 255 (M+).

Step 3: 3(R,S)-(Methylsulphinyl)aniline

A solution of N-tert-butyloxycarbonyl-3(R,S)-(methylsulphinyl)aniline (480 mg, 1.88 mmol) in a mixture of dichloromethane (15 ml) and trifluoroacetic acid (4 ml) was allowed to stand at room temperature for 30 min. Solvents were removed under vacuum and the residue azeotroped with methanol (10 ml) then purified by flash chromatography on silica gel, using a gradient elution (ethyl acetate:ethanol, 98:2 to 95:5) to give the title compound (280 mg, 96%) as a pale yellow solid. $^1$H NMR (250 MHz, $CDCl_3$+D6-DMSO) δ 2.70 (3H, s), 6.77 (1H, ddd, J=7.8, 2.0 and 0.9 Hz), 6.86 (1H, ddd, J=7.8, 1.5 and 0.9 Hz), 7.00 (1H, t, J=2.0 Hz), 7.25 (1H, t, J=7.8 Hz). MS (CI, $NH_3$) 154 (M-1).

Step 4:
N-[3(R,S)-5-Cyclohexyl-2,3-dihydro-1-methyl-2-oxo-1H-1,4-benzodiazepin-3-yl]N'-[3(R,S)-(methylsulphinyl)phenyl]urea The title compound was prepared in 32% yield from 5-cyclohexyl-1,3-dihydro-1-methyl-3(R,S)-[(4-nitrophenyloxycarbonyl)amino]-2H-1,4-benzodiazepin-2-one and 3(R,S)-(methylsulphinyl)aniline using the same method as that described in Example 11, Step 4. The crude product was purified by flash chromatography on silica gel, using dichloromethane:methanol (94:6) as the eluant and crystallised from ethyl acetate. mp 160° C. $^1$H NMR (360 MHz, D6-DMSO) δ 0.92 (1H, m), 1.06–1.66 (7H, m), 1.78 (1H, m), 1.90 (1H, m), 2.68 (3H, s), 2.93 (1H, m), 3.32 (3H, s), 5.07 (1H, d, J=8.2 Hz), 7.17 (1H, brd, J=6.6 Hz), 7.33–7.44 (4H, m), 7.55 (1H, d, J=7.6 Hz), 7.64 (1H, t, J=7.0 Hz), 7.75 (1H, d, J=8.2 Hz), 7.77 (1H, s), 9.30 (1H, s). MS (CI, NH$_3$) 453 (M+).

EXAMPLE 43

N-[3(R,S)-5-Cyclohexyl-2,3-dihydro-1-methyl-2-oxo-1H-1,4-benzodiazepin-3-yl]N'-[3-(5-hydroxy-4-pyron-2-yl)phenyl]urea Step 1: 3-Acetoxy-6-(3-nitrophenyl)-4-pyrone To a stirred solution of hexamethyldisilazane (10.8 ml, 0.05 mol) in anhydrous tetrahydrofuran (140 ml), at −78° C., was added n-butyllithium (31.9 ml of a 1.6M solution in hexane, 0.05 mol) dropwise. After 20 min a solution of 1-methoxy-2-acetoxybuten-3-one (8.0 g, 0.05 mol) in anhydrous tetrahydrofuran (60 ml) was added dropwise. After a further 20 min a solution of 3-nitrobenzoyl chloride (4.82 g, 0.026 mol) in anhydrous tetrahydrofuran (40 ml) was added dropwise. The cooling bath was removed and the reaction mixture warmed to −15° C. over 30 min. The mixture was then quenched using 2M HCl (50 ml) and stirred for 1 h. The organic layer was separated and the aqueous phase extracted with ether (2×100 ml). The combined organic layers were washed with brine (200 ml), dried (Na$_2$SO$_4$) and evaporated in vacuo to give an orange gum.

This gum was dissolved in toluene (100 ml), pyridinium paratoluene sulphonate (1 g) was added and the mixture heated to reflux for 1 h. The solvent was removed in vacuo, the residue dissolved in chloroform (300 ml) and washed with 10% sodium bicarbonate solution (2×100 ml) and water (100 ml). The organic phase was separated, dried (Na$_2$SO$_4$) and evaporated in vacuo to afford a brown residue. The residue was chromatographed on silica gel, eluting with ethyl acetate to afford a beige solid, which was recrystallised from ethyl acetate to give the title compound (2.00 g, 28%) as a cream solid. mp 170°–171° C. $^1$H NMR (360 MHz, CDCl$_3$) δ 2.37 (3H, s), 7.00 (1H, s), 7.73 (1H, dd, J=8.0 and 8.0 Hz), 8.05–8.08 (2H, m), 8.39 (1H, dd, J=8 and 1 Hz), 8.66 (1H, dd, J=1 and 1 Hz).

Step 2: 3-Acetoxy-6-(3-aminophenyl)-4-pyrone

3-Acetoxy-6-(3-nitrophenyl)-4-pyrone (1.80 g, 6.5 mmol) was dissolved in methanol (50 ml) and hydrogenated at 10 psi for 1 h, using 10% palladium on carbon catalyst (0.2 g, 11% (w/w)). The reaction mixture was then filtered through "hyflo" and the filtrate evaporated in vacuo. The residue was recrystallised from ethyl acetate:hexane (2:1) to afford the desired product (1.20 g, 75%) as a beige solid. mp 127°–129° C. $^1$H NMR (360 MHz, CDCl$_3$) δ 2.35 (3H, s), 3.85 (2H, brs), 6.81 (1H, dd, J=8.0 and 1.0 Hz), 6.84 (1H, s), 7.02 (1H, dd, J=1.0 and 1.0 Hz), 7.11 (1H, brd, J=8.0 Hz), 7.25 (1H, dd, J=8.0 and 8.0 Hz), 7.98 (1H, s).

Step 3:
N-[3(R,S)-5-Cyclohexyl-2,3-dihydro-1-methyl-2-oxo-1H-1,4-benzodiazepin-3-yl]N'-[3-(5-acetoxy-4-pyron-2-yl)phenyl]urea To a stirred and cooled (4° C.) solution of 3-acetoxy-6-(3-aminophenyl)-4-pyrone (335 mg, 1.37 mmol) in anhydrous tetrahydrofuran (8 ml), was added triphosgene (133 mg, 0.45 mmol) followed by triethylamine (0.19 ml, 1.37 mmol). The ice bath was removed and the reaction mixture stirred at room temperature for 20 min. A solution of 3(R,S)-amino-5-cyclohexyl-1,3-dihydro-1-methyl-2H-1,4-benzodiazepin-2-one (310 mg; 1.14 mmol) in anhydrous tetrahydrofuran (8 ml) was added and the reaction mixture stirred at room temperature for 1 h. After this time water (20 ml) and ethyl acetate (30 ml) were added, the organic layer separated and the aqueous phase extracted with ethyl acetate (30 ml). The combined organic layers were washed with water (30 ml) and brine (30 ml) then dried (Na$_2$SO4). The filtrate was evaporated in vacuo and the resultant orange solid recrystallised from ethyl acetate/ether to give the title compound (520 mg, 84%) as a pale yellow solid. mp 183°–187° C. $^1$H NMR (360 MHz, CDCl$_3$) δ 1.08–2.04 (10H, m), 2.34 (3H, s), 2.81 (1H, dd, J=11 and 11 Hz), 3.45 (3H, s), 5.39 (1H, d, J=7.5 Hz), 6.81 (1H, s), 7.03 (1H, d, J=7.5 Hz), 7.25–7.60 (8H, m), 7.87 (1H, s), 7.93 (1H, s).

Step 4:
N-[3(R,S)-5-Cyclohexyl-2,3-dihydro-1-methyl-2-oxo-1H1,4-benzodiazepin-3-yl]N/-[3-(5-hydroxy-4-pyron-2-yl)phenyl-]urea To a stirred suspension of N-[3(R,S)-5-cyclohexyl-2,3-dihydro-1-methyl-2-oxo-1H-1,4-benzodiazepin-3-yl]N'-[3-(5-acetoxy-4-pyron-2-yl)phenyl]urea (390 mg, 0.72 mmol) in methanol (60 ml) was added potassium carbonate (150 mg, 1.08 mmol). The reaction mixture was stirred at room temperature for 1 h. Citric acid (226 mg, 1.1 mmol) was added and the solvent evaporated in vacuo. The residue was partitioned between water (15 ml) and ethyl acetate (30 ml), and the organic layer separated. The aqueous phase was re-extracted with ethyl acetate (30 ml) and the combined organic layers dried (Na$_2$SO$_4$) and evaporated in vacuo. The resultant pale yellow solid was recrystallised from ethyl acetate/ether to afford the title compound (250 mg, 69%) as a beige solid. mp 207°–210° C. $^1$H NMR (360 MHz, D6-DMSO) δ 0.88–1.93 (10H, m), 2.94 (1H, dd, J=13 and 13 Hz), 3.33 (3H, s), 5.08 (1H, d, J=8 Hz), 6.90 (1H, s), 7.34–7.45 (5H, m), 7.55 (1H, d, J=7 Hz), 7.64 (1H, dd, J=7 and 7 Hz), 7.75 (1H, d, J=7 Hz), 7.99 (1H, s), 8.13 (1H, s), 9.23 (2H, brs).

EXAMPLE 44

N-[3(R,S)-5-Cyclohexyl-2,3-dihydro-1-methyl-2-oxo-1H-1,4-benzodiazepin-3-yl]N'-3,4-dihydro-2,2-dioxo-4-oxo-1H-2,3-benzothiazin-6-yl]urea Step 1: Methyl 2-methyl-5-nitrobenzoate To methanol (150 ml) at 0° C. under nitrogen was added dropwise thionyl chloride (4.0 ml, 54.8 mmol) over 2 min. The mixture was stirred at 0° C. for 15 min, before adding a solution of 2-methyl-5-nitrobenzoic acid (4.99 g, 27.5 mmol) in methanol (50 ml) by cannula over 5 min. The mixture was then allowed to warm to room temperature before heating at 50° C. for 18 h under nitrogen. The solvents were evaporated in vacuo and the residue stirred with water (100 ml) and dichloromethane (100 ml). The aqueous layer was basified with potassium carbonate, separated and reextracted with more dichloromethane (100 ml). The two organic extracts were combined, dried (MgSO₄), and evaporated in vacuo to leave the title compound (5.24 g, 98%) as a white solid. ¹H NMR (360 MHz, CDCl₃) δ 2.72 (3H, s), 3.96 (3H, s), 7.44 (1H, d, J=8.3 Hz), 8.24 (1H, dd, J=8.4 and 2.6 Hz), 8.78 (1H, d, J=2.6 Hz).

Step 2: Sodium 2-carbomethoxy-4-nitrobenzyl sulphonate

A mixture of methyl 2-methyl-5-nitrobenzoate (2.51 g, 12.9mmol) and benzoyl peroxide (containing approx. 25% water) (164 mg, 0.51 mmol) in carbon tetrachloride (50 ml) was purged with nitrogen before removing 12 ml of the solvent by distillation. N-Bromosuccinimide (2.30 g, 12.9 mmol) was then added in small portions to the refluxing mixture under irradiation (60W) and the mixture heated at reflux for 2.5 h under nitrogen. The succinimide was removed by filtration and the filtrate evaporated in vacuo to give crude methyl 2-bromomethyl-5-nitrobenzoate (3.67 g) as a yellow oil. To this was added sodium sulphite (2.43 g, 19.3 mmol) and water (10 ml) and the mixture heated at 90° C. for 3 h. The resulting solution was allowed to cool to room temperature and the solid formed was collected, washed with cold water (2×5 ml), then diethyl ether (3×10 ml), and dried under high vacuum in the presence of phosphorus pentoxide. Two more crops were similarly collected to afford the title product (1.46 g, 38%) as a white solid. mp 290°–297° C. ¹H NMR (360 MHz, D6-DMSO) δ 3.84 (3H, s), 4.34 (2H, s), 7.68 (1H, d, J=8.5 Hz),8.30 (1H, dd, J=8.5 and 2.6 Hz), 8.41 (1H, d, J=2.5 Hz). MS (FAB) 274 (M-1).

Step 3: Methyl 2-(aminosulphonylmethyl)-5-nitrobenzoate

A mixture of sodium 2-carbomethoxy-4-nitrobenzylsulphonate (0.68 g, 2.29 mmol) and phosphorous pentachloride (0.74 g, 3.55 mmol) was heated at 100° C. for 70 min, before removing the phosphorous oxychloride in vacuo. The residue was stirred with dichloromethane (5 ml) at 40° C., then filtered, washing the solid well with more dichloromethane. The combined filtrates were taken and ammonia gas was bubbled through the solution for 5 min. The mixture was immediately filtered and the filtrate left to stand for 3 days. After this time a white crystalline solid was collected. Concentration of the filtrate afforded a second crop to give the title product (438 mg, 70%) as a white solid. mp 167°–170° C. ¹H NMR (360 MHz, D6-DMSO) δ 3.90 (3H, s), 4.94 (2H, s), 7.00 (2H, brs), 7.77 (1H, d, J=8.5 Hz), 8.46 (1H, dd, J=8.5 and 2.5 Hz), 8.56 (1H, d, J=2.5 Hz). MS (CI, NH₃) 292 (M+NH₄⁺).

Step 4: 3,4-Dihydro-2,2-dioxo-6-nitro-4-oxo-1-2,3-benzothiazine

To a solution of methyl 2-(aminosulphonylmethyl)-5-nitrobenzoate (314 mg, 1.14 mmol) in dimethylformamide (25 ml) was added sodium hydride (60% dispersion in oil, 45 mg, 1.13 mmol) and the resulting red mixture stirred at room temperature for 3 h. The mixture was then partitioned between 2N HCl (100 ml) and ethyl acetate (100 ml). The aqueous layer was re-extracted with ethyl acetate (2×100 ml), and the combined organic extracts were dried (MgSO₄) and evaporated in vacuo. The residue was purified by flash chromatography on silica gel, eluting with 10–30% methanol/dichloromethane, to afford the title compound (275 mg, 100%) as a white solid. ¹H NMR (360 MHz, D6-DMSO) δ 4.28 (2H, s), 7.59 (1H, d, J=8.3 Hz), 8.25 (1H, dd, J=8.3 and 2.6 Hz), 8.64 (1H, d, J=2.6 Hz).

Step 5: 6-Amino-3,4-dihydro-2,2-dioxo-4-oxo-1H-2,3-benzothiazine

A mixture of 3,4-dihydro-2,2-dioxo-6-nitro-4-oxo-1H-2,3-benzothiazine (267 mg, 1.1 mmol) and 10% palladium on carbon (26 mg, 10% (w/w)) in methanol (50 ml) was hydrogenated at 50 psi for 30 min. The mixture was then filtered, the solid washed with methanol and the filtrates evaporated in vacuo to give the title compound (239 mg, 100%) as a yellow solid. ¹H NMR (360 MHz, D6-DMSO) δ 3.87 (2H, s), 5.11 (2H, brs), 6.59 (1H, dd, J=8.0 and 2.5 Hz), 6.88 (1H, d, J=8.0 Hz), 7.15 (1H, d, J=2.5 Hz). MS (FAB) 211 (M-1).

Step 6: N-[3(R,S)-5-Cyclohexyl-2,3-dihydro-1-methyl-2-oxo-1H-1,4-benzodiazepin-3-yl]N'-[3,4-dihydro-2,2-dioxo-4-oxo-1H-2,3-benzothiazin-6-yl]urea To a solution of 5-cyclohexyl-1,3-dihydro-1-methyl-3(R,S)-[(4-nitrophenyloxycarbonyl)amino]-2H-1,4-benzodiazepin-2-one (22 mg, 0.51 mmol) in anhydrous dimethylformamide (3 ml) under nitrogen was added triethylamine (70 μl, 0.51 mmol). The solution was stirred for 5 min before adding a solution of 6-amino-3,4-dihydro-2,2-dioxo-4-oxo-1H-2,3-benzothiazine (107 mg, 0.51 mmol) and triethylamine (70 μl, 0.51 mmol) in anhydrous dimethylformamide (3 ml) and acetonitrile (10 ml). The resulting solution was heated at 50° C. for 10 h, before removing the solvents in vacuo and partitioning the residue between 20% aqueous acetic acid (5 ml) and ethyl acetate (20 ml). The aqueous phase was re-extracted with more ethyl acetate (2×20 ml) and the combined organic extracts dried (Na₂SO₄) and evaporated in vacuo. The resulting yellow oil was stirred with diethyl ether (10 ml) to give a pale yellow solid. This was purified by flash chromatography on silica gel, eluting with 5–20% methanol/dichloromethane, to afford the title compound (95 mg, 37%) as a pale yellow solid, which was recrystallised from isopropanol/dichloromethane. mp>300° C. ¹H NMR (360 MHz, D6-DMSO) δ 0.93 (1H, m), 1.12–1.64 (7H, m), 1.76 (1H, m), 1.89 (1H, m), 2.93 (1H, m), 3.29 (3H, s), 3.96 (2H, s), 5.08 (1H, d, J=8.4 Hz), 7.09 (1H, d, J=8.3 Hz), 7.24 (1H, d, J =8.5 Hz), 7.38 (1H, t, J=7.9 Hz), 7.49 (1H, dd, J=8.2 and 2.4 Hz), 7.55 (1H, d, J=8.3 Hz), 7.63 (1H, t, J=7.9 Hz), 7.74–7.76 (2H, m), 9.04 (1H, s). MS (FAB) 508 (M-1).

Also prepared by methods analogous to those described above were:

EXAMPLE 45

N-[3(R)-5-cyclohexyl-2,3-dihydro-1-methyl-2-oxo-1H-1,4-benzodiazepin-3-yl]N'-[4-methyl-3-(2-methylphenyl sulphonylaminocarbonyl)phenyl]urea, m.p. 171° C. (dec.).

EXAMPLE 46

N-[3(R)-5-cyclohexyl-2,3-dihydro-1-methyl-2-oxo-1H-1,4-benzodiazepin-3-yl]N'-[3-(2-chlorophenylsulphonyl aminocarbonyl)phenyl]urea, m.p. 170° C. (dec.).

EXAMPLE 47

N-[3(S)-5-cyclohexyl-2,3-dihydro-1-methyl-2-oxo-1H-1,4-benzodiazepin-3-yl]N'-[3-phenylsulphonylaminocarbonyl) phenyl]urea, m.p. 180° C. (dec.).

EXAMPLE 48A

Tablets Containing 1-25 mg of Compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 48B

Tablets Containing 26-100 mg of Compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 49

Parenteral Injection

|  | Amount mg |
| --- | --- |
| Compound of formula (I) | 1 to 100 mg |
| Citric Acid Monohydrate | 0.75 mg |
| Sodium Phosphate | 4.5 mg |
| Sodium Chloride | 9 mg |
| Water for injection | to 1 ml |

The sodium phosphate, citric acid monohydrate and sodium chloride are dissolved in a portion of the water. The compound of formula (I) is dissolved or suspended in the solution and made up to volume.

EXAMPLE 50

Topical Formulation

|  | Amount mg |
| --- | --- |
| Compound of formula (I) | 1-10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

BIOLOGICAL ACTIVITY

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 83, 4923-4926, 1986) with minor modifications.

Male Sprague-Dawley rats (150-200 g) were sacrificed by decapitation. The whole pancreas was dissected free of fat tissue and was homogenized in 25 volumes of ice-cold 10 mM N-2-hydroxyethyl-piperazine-N'-2-ethane sulphonic acid (HEPES) buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20mM (HEPES)), 1 mM ethylene glycol-bis-($\beta$-aminoethylether-N,N'-tetraacetic acid) (EGTA), 5 mM $MgCl_2$, 150 mM NaCl, bacitracin 0.25 mg/ml, soya bean trypsin inhibitor 0.1 mg/ml, and bovine serum albumin 2 mg/ml pH 6.5 at 25° C.) using a Teflon (trademark). homogenizer, 15 strokes at 500 rpm. The homogenate was further diluted in binding assay buffer to give a final concentration of 0.5 mg original wet weight/1 ml buffer. For the binding assay, 50 $\mu$l of buffer (for total binding) or unlabelled CCK-8 sulphated to give a final concentration of 1 $\mu$M (for non-specific binding) or the compounds of Formula I (for determination of inhibition of $^{125}$I-CCK-8 binding) and 50 $\mu$l of 500 pM $^{125}$I-CCK-8 (i.e. 50 pM final concentration) were added to 400 $\mu$l of the membrane suspensions in microfuge tubes. All assays were run in.duplicate. The reaction mixtures were incubated at 25° C. for 2 hours and the reaction terminated by rapid filtration (Brandell 24 well cell harvester) over Whatman GF/C filters, washing 3×4 mls with ice-cold 100 Mm NaCl. The radioactivity on the filters was counted with a LKB gamma counter.

2. CCK Receptor Binding (Brain)

CCK-8 sulphated was radiolabelled and the binding was performed according to the description for the pancreas method with minor modifications.

Male Hartley guinea pigs (300-500 g) were sacrificed by decapitation and the cortex was removed and homogenized in 25 mL ice-cold 0.32M sucrose. The homogenates were centrifuged at 1000 g for 10 minutes and the resulting supernatant was recentrifuged at 20,000 g for 20 minutes. The $P_2$ pellet was resuspended in binding assay buffer (20 mM HEPES, 5 mM $MgCl_2$, 0.25 mg/ml bacitracin, 1 mM EGTA pH 6.5 at 25° C.), using a Teflon (trademark) homogenizer (5 strokes at 500 rpm) to give a final concentration of 10 mg original wet weight/1.2 ml buffer. For the binding assay, 50 $\mu$l of buffer (for total binding) or unlabelled CCK-8 sulphated to give a final concentration of 1 $\mu$M ( for non-specific binding) or the compounds of Formula I (for determination of inhibition of $^{125}$I-CCK-8 binding) and 50 $\mu$l of 500 pM $^{125}$I-CCK-8 (i.e. final concentration of 50 pM) were added to 400 $\mu$l of the membrane suspensions in microfuge tubes. All assays were run in duplicate. The reaction mixtures were incubated at 25° C. for 2 hours and then the reaction was terminated by rapid filtration (Brandell 24 well cell harvester) on Whatman GF/C filters with 3×5 ml washes of cold 100 mM NaCl. The radioactivity on the filters was counted with a LKB gamma counter.

3. Gastrin Antagonism

Gastrin antagonist activity of compounds of Formula I was determined using the following assay.

A. Gastrin Receptor Binding in Guinea Pig Gastric Glands

Preparation of guinea pig gastric mucosal glands

Guinea pig gastric mucosal glands were prepared by the procedure of Chang et. al., Science, 230, 177–179 (1985) with slight modifications. Gastric mucosa from guinea pigs (300–500 g body weight, male Hartley) were isolated by scraping with a glass slide after washing stomachs in ice-cold, aerated buffer consisting of the following: 130 mM NaCl, 12 mM NaHHCO$_3$, 3 mM NaH$_2$PO$_4$, 3 nM Na$_2$HPO$_4$, 3 mM K$_2$HPO$_4$, 2 mM MgSO$_4$1, mM CaCl$_2$, 5 mM glucose and 4 mM L-glutamine, 50 mM HEPES, 0.25 mg/ml bacitracin, 0.10 mg/ml soya bean trypsin inhibitor, 0.1 mg/ml bovine serum albumin, at pH 6.5, and then incubated in a 37° C. shaking water bath for 40 minutes in buffer containing 1 mg/ml collagenase and bubbled with 95% O$_2$ and 5% CO$_2$. The tissues were passed twice through a 5 ml syringe to liberate the gastric glands, and then filtered through Nitex (trademark) #202 gauge nylon mesh. The filtered glands were centrifuged at 272 g for 5 minutes and washed twice by resuspension in 25 ml buffer and centrifugation.

B. Binding Studies

The washed guinea pig gastric glands prepared as above were resuspended in 25 ml of standard buffer. For binding studies, to 250 μl of gastric glands, 30 μl of buffer (for total binding) or gastrin (3 μM final concentration, for nonspecific binding) or test compound and 20 μl of $^{125}$I-gastrin (NEN, 2200 Ci/mmole, 0.1 nM final concentration) were added. All assays were run in triplicate. The tubes were aerated with 95% O$_2$ and 5% CO$_2$ and capped. The reaction mixtures, after incubation at 25° C. for 30 minutes in a shaking water bath were rapidly filtered (Brandell 24 well cell harvester) over Whatman G/F B filters presoaked in assay buffer and immediately washed further with 3×4 ml of 100 mM ice cold NaCl. The radioactivity on the filters was measured using a LKB gamma counter.

In Vitro Results

Effects of the Compounds of Formula I on $^{125}$I-CCK-8 receptor binding

The preferred compounds of Formula I are those which produced dose-dependent inhibition of specific $^{125}$I-CCK-8 binding as defined as the difference between total and non-specific (i.e. in the presence of 1 μM CCK) binding.

Drug displacement studies were performed with at least 10 concentrations of compounds of Formula I and the IC$_{50}$ values were determined by regression analysis IC$_{50}$ refers to the concentration of the compound required to inhibit 50% of specific binding of $^{125}$I-CCK-8.

The data in Table I were obtained for compounds of Formula I.

TABLE I

CCK RECEPTOR BINDING RESULTS IC$_{50}$(nM)

| Compound of Ex # | $^{125}$I-CCK Pancreas | $^{125}$I-CCK Brain | $^{125}$I-Gastrin Gastric Glands |
|---|---|---|---|
| 1 | 1.5 | 2.2 | 0.83 |
| 2 | 27% at 3 μM | 0.42 | NT |
| 3 | 800 | 0.3 | NT |
| 4 | 11 | 0.09 | 0.44 |
| 5 | 140 | 0.71 | NT |
| 6 | 1100 | 0.96 | NT |
| 7 (Peak A) | 1700 | 0.47 | 0.92 |
| 7 (Peak B) | 0.36 | 100 | NT |
| 8 | 56 | 1.6 | NT |
| 9 | NT | NT | NT |
| 10 | 3.1 | 1.4 | NT |
| 11 | 118 | 0.32 | NT |
| 12 | 12.4 | 0.29 | 3.24 |
| 13 | 738 | 0.24 | 27 |
| 14 | 11.1 | 0.58 | NT |
| 15 | 19.8 | 0.4 | 1.06 |
| 16 | 2.0 | 0.58 | 0.45 |
| 17 | 137 | 0.9 | 10.5 |
| 18 | 13.8 | 0.09 | NT |
| 19 | 570 | 12 | NT |
| 20 | 953 | 1.4 | 1.77 |
| 21 | 9.7 | 1.2 | NT |
| 22 | 70 | 6.8 | NT |
| 23 | 5 | 0.96 | NT |
| 24 (Peak A) | 1180 | 0.78 | 0.7 |
| 24 (Peak B) | 5 | 18.9 | NT |
| 25 | 220 | 1.9 | NT |
| 26 | 60 | 2.3 | NT |
| 27 | 19% at 3 μM | 0.38 | 1.34 |
| 28 | 8.3 | 4 | NT |
| 29 | 22 | 6.3 | NT |
| 30 | 170 | 3.2 | NT |
| 31 | 6.2 | 0.22 | NT |
| 32 | 610 | 1.3 | NT |
| 33 | 1600 | 0.27 | NT |
| 34 | 1700 | 2.3 | NT |
| 35 | 10.2 | 50.8 | NT |
| 36 | 1300 | 1.2 | NT |
| 37 | 960 | 0.19 | NT |
| 38 | 300 | 6.8 | NT |
| 39 | 270 | 0.56 | 1.18 |
| 40 | 310 | 3.8 | NT |
| 41 | NT | NT | NT |
| 42 | 18 | 15 | NT |
| 43 | 17.8 | 2.1 | NT |
| 44 | 100 | 3.4 | NT |

N.T. = not tested.

EXAMPLE 51

N-[3(R.S.)-5-Cyclohexyl-2,3-dihydro-1-methyl-2-oxo-1H-1,4-benzodiazepin-3-yl]N'-[3-(2-(imidazol-3-yl)ethyl)phenyl]urea Step 1: 1-(1,1-Dimethylethyloxycarbonyl)-2-((3-nitrophenyl)ethen-2-yl)imidazole A suspension of 3-nitrobenzyl bromide (10 g, 46 mmol) in acetonltrile (100 ml) was added to a solution of triphenylphosphine (13.3 g, 51 mmol) in acetonitrile (150 ml). The resulting suspension was heated at reflux (15 min), cooled and 15.5 g of (3-nitrobenzyl)triphenylphosphonium bromide was obtained by filtration. A mixture of this compound (10 g, 21 mmol) and imidazole-2-carboxaldehyde (2 g, 21 mmol) was heated at reflux in ethanol (200 ml) and a solution of sodium ethoxide in ethanol (sodium (480 mg, 21 mmol; ethanol (100 ml)) was added dropwise over 2 h. After a further 3 h at reflux the solution was cooled, filtered and the solvent evaporated. The residue was taken up in 2M HCl (50 ml). The aqueous phase was washed with diethyl ether (3×50 ml), basified with 1N sodium hydroxide solution and the product extracted into diethyl ether (3×50 ml). The organic phase was dried (NaSO4) and evaporated to afford 4 g of a crude cis/trans mixture of 2-((3-nitrophenyl)ethen-2-yl)imidazole as a yellow solid. This material (1.75 g, 8.14 mmol) was dissolved in a mixture of dichloromethane (40 ml) and acetonitrile (40 ml) and di-t-butyl dicarbonate (2.13 g, 9.8 mmol) was added. After 48 h at room temperature the solvent was evaporated and the residue chromatographed on silica gel with ethyl acetate:petrol (bp 60°–80°) (1:1) as eluant to afford 1.7 g of a cis/trans mixture of the titled compound as a yellow oil. $^1$H NMR (250 MHz, CDCl3) δ 1.64 and 1.70 (9H, 2s), 6.72–8.50 (8H).

Step 2:
1-(1,1-Dimethylethyloxycarbonyl)-2-((3-aminophenyl)ethan-2-yl)imidazole A solution of 1-(1,1-dimethylethyloxycarbonyl)-2-((3-nitrophenyl)ethen-2-yl)imidazole (500 mg, 1.59 mmol)in ethanol (50 ml) was hydrogenated at 30 psi in the presence of 10% palladium-on-carbon (50 mg) for 1 h. The catalyst was then removed by filtration and the solvent evaporated to afford the titled compound as a viscous oil (340 mg, 75% yield). $^1$H NMR (250 MHz, CDCl3) δ 1.60 (9H, s), 2.92–3.04 (2H, m), 3.22–3.36 (2H, m), 3.70 (2H, brs), 6.42–6.68 (3H, m), 6.87 (1H, d, J=2.5 Hz), 7.05 (1H, t, J=8 Hz), 7.32 (1H, d, J=2.5 Hz).

Step 3:
N-(3(R,S)-5-Cyclohexyl-2,3-dihydro-1-methyl-2-oxo-1H-1,4-benzodiazepin-3-yl]N'-[3-(2-(imidazol-2-yl)ethyl)phenyl]urea To a stirred solution of 5-cyclohexyl-1,3-dihydro-1-methyl-3(R,S)-[(4-nitrophenyloxycarbonyl)amino]-2H-1,4-benzodiazepin-2-one (250 mg, 0.57 mmol) in dimethylformamide (5 ml) was added triethylamine (80 µl, 0.57 mmol). After 5 min a solution of 1-( 1,1-dimethylethyloxycarbonyl)-2-( (3-aminophenyl)ethan-2-yl)imidazole (165 mg, 0.573 mmol) in dimethylformamide (5 ml) was added and the solution heated at 50° C. for 4.5 h. After this time the solution was cooled to ambient temperature and evaporated. The residue was partitioned between sodium bicarbonate solution (50 ml) and ethyl acetate (50 ml). The organic phase was washed with sodium bicarbonate solution (3×50 ml), dried (Na2SO4) and evaporated to afford a gummy solid which was dissolved in dichloromethane (5 ml) to which was added trifluoroacetic acid (0.5 ml). The resulting solution was stirred at room temperature for 18 h after which time the volatiles were removed by evaporation. The gummy residue was partitioned between dichloromethane (50 ml) and sodium bicarbonate solution (20 ml). The insolubles were collected by filtration, washed with water and ether and recrystallised from ethanol to afford the titled compound as a colourless solid, mp, 202°–204° C. $^1$H NMR (360 MHz, D6-DMSO+TFA) δ 0.80–2.00 (10H, m), 2.95–3.05 (3H, m), 3.16 (2H, t, J=7 Hz), 3.33 (3H, s), 5.10 (1H, s), 6.68–6.75 (1H, m), 7.10–7.20 (2H, m), 7.26–7.44 (3H, m), 7.50–7.58 (3H, m), 7.66 (1H, t, J=7 Hz), 7.78 (1H, d, J=8 Hz), 9.0 (1H, s), 14.0 (1H, brs).

We claim:
1. A compound of formula (I), or a pharmaceutically acceptable salt or prodrug thereof:

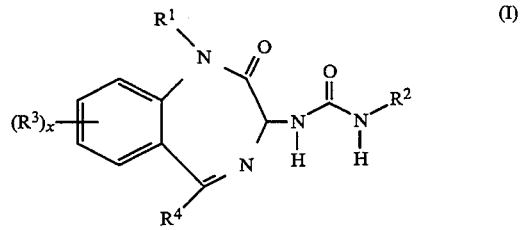

wherein:
$R^1$ is selected from the group consisting of $(CH_2)_q$ imidazolyl, $(CH_2)_q$ tetrazolyl, $(CH_2)_q$ triazolyl; $C_{1-6}$ alkyl unsubstituted or substituted by one or more groups selected from halo, hydroxy and $NR^6R^7$; $C_{3-7}$cycloalkyl; cyclopropylmethyl; $CH_2CO_2R^5$; $CH_2CONR^6R^7$; or $CH_2CH(OH)$-W-$(CH_2)_2NR^6R^7$ where $R^5$ represents $C_{1-4}$alkyl, $R^6$ and $R^7$ each independently represents a hydrogen atom or a $C_{1-4}$alkyl group, or taken together with the nitrogen atom to which they are attached form a pyrrolidinyl, or piperidinyl ring, q is 1, 2 or 3, and W is S or NH;

$R^2$ is selected from the group consisting of:
(i) a phenyl group unsubstituted or substituted by one or more substituents selected from $C_{1-6}$alkyl unsubstituted or substituted by hydroxy, CON-$R^aR^b$, $CO_2R^a$ or $OCONR^aR^b$$C_{2-6}$alkenyl unsubstituted or substituted by $CO_2R^a$; $C_{2-6}$alkynyl; halo; unprotected or protected hydroxy; $NHR^8$; $NHPO(OC_{1-4}alkyl)$; $(CH_2)_n$tetrazolyl unsubstituted or substituted in the tetrazolyl ring by $C_{1-4}$alkyl; $(CH_2)_n$imidazolyl; CONH-tetrazolyl; CONH-triazolyl; diazolinone; triazolinone unsubstituted or substituted by methyl; tetrazolinone; oxathiadiazolone; 5-hydroxy-4-pyrone; $CONH_2$; $CONHCOR^9$; $SO(C_{1-6}$ alkyl); $SO_2(C_{1-6}alkyl)$; $CONHCO_2R^9$; $CONHCONHR^9$; $C(NH_2)NOH$; $COC_{1-4}alkyl$; $CONHSO^2R^9$; $SO^2NH_2$; $NHSO^2NH_2$; $SO^2NHCO_2R^9$; $SO_2NH$-$CONHR^9$; $SO^2NHSO^2R^9$; $SO^2NHPO(OR^aR^b)$; $SO^2NHR^{10}$; cyano; $B(OH)_2$; $CO_2H$; $CH_2OCH_2O(CH_2)_2OCH_3$, where $R^a$ and $R^b$ each independently represent H or $C_{1-6}$ alkyl, n is 0, 1 or 2, $R^8$ represents H or $COC_{1-6}$ alkyl, $R^9$ represents $C_{1-6}$ alkyl, unsubstituted or substituted phenyl, wherein the substitutents are selected from $C_{1-4}$alkyl, $C_{1-4}$alkoxy, halo and trifluoromethyl, 2,2-difluorocyclopropane or trifluoromethyl, and $R^{10}$ represents a nitrogen containing heterocycle selected from the group consisting of thiazole, thiadiazole, and pyrazine;

ii) a group

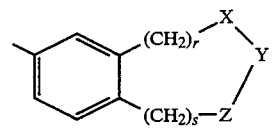

wherein
X and Z each independently represent $CH_2$, O, $SO^2$, C=O, NH or N; and
Y represents $CH_2$, C=O, $NR^a$ or N, where $R^a$ is as above defined:

r and s each independently represent 0 or 1; and the dotted line represents an optional double bond;

provided that: X and Z can only be the same when they are O, and when one of X and Z is O, the other of X and Z must be O;

when X or Z is N, Y is also N and the ring contains one unit of unsaturation;

when X or Z is SO$^2$, Y is NH and the other of X and Z is C=O:

whichever of r and s is adjacent to SO$_2$ can be 1; otherwise r and s are the same and O;

(iii) a pyridyl group substituted by C$_{1-4}$alkoxy or halo:

R$^3$ represents C$_{1-6}$alkyl or halo;
R$^4$ represents C$_{3-7}$ cycloalkyl;
x is 0, 1, 2 or 3.

2. A compound as claimed in claim 1 of formula (Ia),

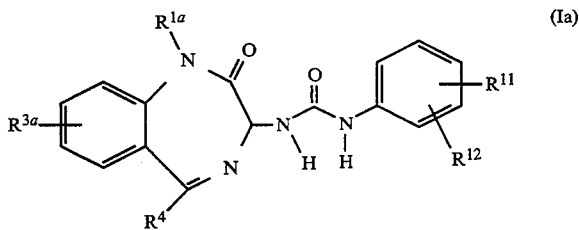

(Ia)

wherein:
R$^{1a}$ represents C$_{1-6}$alkyl;
R$^{3a}$ represents hydrogen;
R$^4$ represents C$_{3-7}$ cycloalkyl;
R$^{11}$ is selected from hydrogen and C$_{1-6}$alkyl;
R$^{12}$ is selected from C$_{1-6}$alkyl; halo; (CH$_2$)$_n$-tetrazolyl unsubstituted or substituted in the tetrazole ring by Cl$_{1-4}$alkyl; (CH$_2$)$_n$-imidazolyl; 5-hydroxy-4-pyrone; SO(C$_{1-6}$alkyl); CONHSO$_2$R$^{9a}$; SO$_2$NHCOR$^{9a}$ (where R$^{9a}$ is C$_{1-6}$ alkyl, unsubstituted or substituted aryl or trifluoromethyl); SO$_2$NHR$^{10a}$ (where R$^{10a}$ is a nitrogen containing heterocycle);

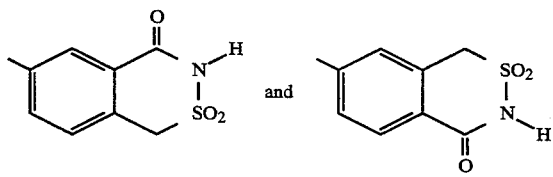

or a salt or prodrug thereof.

3. A compound as claimed in claim 2 wherein R$^{11}$ is H and R$^{12}$ is 3-tetrazol-5-yl.

4. A compound as claimed in claim 2 wherein R$^{12}$ is CONHSO$^2$R$^{9a}$ or SO$_2$NHCOR$^{9a}$.

5. A compound as claimed in claim 1 wherein R$^4$ is cyclobutyl, cyclopentyl or cyclohexyl.

6. A compound as claimed in claim 1 wherein R$^1$ is selected from C$_{1-6}$alkyl, C$_{3-7}$ cycloalkyl, cyclopropylmethyl, (CH$_2$)$_m$-imidazolyl (where m is 1 or 2), CH$_2$CO$_2$R$^6$ (where R$^6$ is C$_{1-4}$alkyl) and CH$_2$CONR$^7$R$^8$; R$^2$ is a phenyl group unsubstituted or substituted by one substituent selected from C$_{1-6}$alkyl, halo, (CH$_2$)$_n$—tetrazolyl unsubstituted or substituted in the tetrazole ring by C$_{1-4}$alkyl, (CH$_2$)$_n$-imidazolyl, CONHSO$_2$R$^{9a}$, SO$_2$NHCOR$^{9b}$ (where R$^{9b}$ is C$_{1-6}$ alkyl, unsubstituted or substituted aryl or trifluoromethyl), SO$_2$NHR$^{10}$ and (CH$_2$)$_n$CO$_2$H; and x is selected from 0 and 1.

7. A compound as claimed in claim 6 wherein R$^2$ is a phenyl group unsubstituted or substituted by one substituent selected from Cl$_6$alkyl, halo, (CH$_2$)$_n$—tetrazolyl, (CH$_2$)$_n$-imidazolyl, CONHSO$_2$R$^9$a, SO$_2$NHCOR$^{9b}$ and (CH$_2$)$_n$CO$_2$H.

8. A compound as claimed in claim 7 wherein R$^2$ is a phenyl group substituted by one substituent selected from C$_{1-6}$alkyl, halo, (CH$_2$)$_n$-tetrazolyl, (CH$_2$)$_n$—imidazolyl and (CH$_2$)$_n$CO$_2$H.

9. A compound as claimed in claim 1 selected from the group consisting of:

N-[3(R,S)-5-cyclohexyl-2,3-dihydro-1-2-methyl-2-oxo-1H-1,4-benzodiazepin-3-yl]N'-[methylphenyl]urea;

N-[3(R,S)-5-cyclohexyl-2,3-dihydro-1-(2-methylpropyl)-2-oxo-1H-1,4-benzodiazepin-3-yl]N'-[3-tetrazol-5ylphenyl]urea;

N-[3(R,S)-5-cyclopentyl-2,3-dihydro-1-(2-methylpropyl)-2-oxo-1H-1,4-benzodiazepin-3-yl]N'-[3-tetrazol-5-ylphenyl]urea;

N-[3(R,S)-5-cyclohexyl-2,3-dihydro-1-methyl-2-oxo-1H-1,4-benzodiazepin-3-yl]N'-[3-tetrazol-5-ylphenyl]urea;

N-[3(R,S)-5-cylopentyl-2,3-dihydro-1-ethyl-2-oxo-1H-1,4-benzodiazepin-3-yl]N'-[3-tetrazol-5-ylphenyl]urea;

N-[3(R,S)-5-cyclopentyl-2,3-dihydro-1-propyl-2-oxo-1H1,4-benzodiazepin-3-yl]N'-[3-tetrazol-5-ylphenyl]urea;

N-[3(R,S)-5-cyclopentyl-2,3-dihydro-1-methyl-2-oxo-1H1,4-benzodiazepin-3-yl]N'-[3-tetrazol-5-ylphenyl]urea;

N-[3(R,S)-5-cyclohexyl-2,3-dihydro-1-methyl-2-oxo1H1,4benzodiazepin-3-yl]N'-[3-ethynylphenyl]urea;

N-[3(R,S)-5-cyclohexyl-2,3-dihydro-1-methyl-2-oxo1H1,4benzodiazepin-3-yl]N'-[3-carboxyphenyl]urea;

N-[3(R,S)-5-cyclohexyl-2,3-dihydro-1-methyl-2-oxo-1H-1,4benzodiazepin-3-yl]N'-[3-(isopropylcarbonylamino sulphonyl)phenyl]urea;

N-[3(R,S)-5-cyclohexyl-2,3-dihydro-1-methyl-2-oxo-1H-1,4-benzodiazepin-3-yl]N'-[3-(isopropylsulphonylamino carbonyl)phenyl]urea;

N-[3(R,S)-5-cyclohexyl-2,3-dihydro-1-methyl-2-oxo-1H-1,4-benzodiazepin-3-yl]N'-[3-(phenylcarbonylaminosulphonyl) phenyl]urea;

N-[3(R,S)-5-cyclohexyl-2,3-dihydro-1-methyl-2-oxo-1H-1,4-benzodiazepin-3-yl]N'-[3-(phenylsulphonylaminocarbonyl) phenyl]urea;

N-[3(R,S)-5-cyclohexyl-2,3-dihydro-1-methyl-2-oxo-1H-1,4-benzodiazepin-3-yl]N'-[3-(methylcarbonylaminosulphonyl) phenyl]urea;

N-[3(R,S)-5-cyclohexyl-2,3-dihydro-1-methyl-2-oxo-1H-1,4-benzodiazepin-3-yl]N'-[3-(methylsulphonylaminocarbonyl) phenyl]urea;

N-[3(R,S)-5-cyclohexyl-2,3-dihydro-1-methyl-2-oxo-1H-1,4-benzodiazepin-3-yl]N'-[3-(trifluoromethylcarbonylamino sulphonyl)phenyl]urea;

N-[3(R,S)-5-cyclohexyl-2,3-dihydro-1-methyl-2-oxo-1H-1,4-benzodiazepin-3-yl]N'-[3-(trifluoromethylsulphonylamino carbonyl)phenyl]urea;

N-[3(R,S)-5-cyclohexyl-2,3-dihydro-1-(2-methylpropyl)-2-oxo-1H-1,4-benzodiazepin-3-yl]N'-[3-(methylsulphonylamino carbonyl)phenyl]urea;

N-[3(R,S)-5-cyclopentyl-2,3-dihydro-1-ethyl-2-oxo-1H-1,4-benzodiazepin-3-yl]N'-[3-(methylcarbonylaminosulphonyl) phenyl]urea;

N-[3(R,S)-5-cyclohexyl-2,3-dihydro-1-methyl-2-oxo-1H-1,4-benzodiazepin-3-yl]N'-[3-(1,3,4-thiadiazol-2-ylamino sulphonyl)phenyl]urea;

N-[3(R,S)-5-cyclohexyl-2,3-dihydro-1-methyl-2-oxo-1H-1,4-benzodiazepin-3-yl]N'-[3-(pyrazinylaminosulphonyl) phenyl]urea;

N-[3(R,S)-5-cyclohexyl -2,3-dihydro-1-methyl-2-oxo-1H-1,4-benzodiazepin-3-yl]N'-[3-(ethylsulphonylaminocarbonyl) phenyl]urea;

N-[3(R)-5-cyclohexyl-2,3-dihydro-1-methyl-2-oxo-1H-1,4-benzodiazepin-3-yl]N'-[3-(isopropylsulphonylamino carbonyl)phenyl]urea;

N-[3(S)-S-cyclohexyl-2,3-dihydro-1-methyl-2-oxo-1B-1,4-benzodiazepin-3-yl]N'-[3-(isopropylsulphonylamino carbonyl)phenyl]urea;

N-[3(R,S)-5-cyclohexyl-2,3-dihydro-1-propyl-2-oxo-1H-1,4-benzodiazepin-3-yl]N'-[3-(methylsulphonylaminocarbonyl) phenyl]urea=

N-[3(R,S)-5-cyclohexyl-2,3-dihydro-1-methyl-2-oxo-1H-1,4-benzodiazepin-3-yl]N'-[3-(thiazol-2-ylaminosulphonyl) phenyl]urea;

(−)-N-[3-(R)-5-cyclohexyl-2,3-dihydro-1-methyl-2-oxo-1H-1,4-benzodiazepin-3-yl]N'-[3-(phenylsulphonyl aminocarbonyl)phenyl]urea;

N-[3(R,S)-5-cyclohexyl-2,3-dihydro-1-methyl-2-oxo-1,4-benzodiazepin-3-yl]N'-[3,(2-methyltetrazol-5-yl)phenyl]urea;

N-[3(R,S)-5-cyclopentyl-2,3-dihydro-1-ethyl-2-oxo-1,4-benzodiazepin-3-yl]N'-[3-(methylsulphonylaminocarbonyl) phenyl]urea;

N-[3(R,S)-5-cyclopentyl-2,3-dihydro-1-ethyl-2-oxo-1H-1,4-benzodiazepin-3-yl]N'-[3-(isopropylsulphonylamino carbonyl)phenyl]urea;

N-[3(R,S)-5-cyclohexyl -2,3-dihydro-1-methyl-2-oxo-1,4-benzodiazepin-3-yl]N'-[3-(1,1-dimethylethylsulphonylamino carbonyl)phenyl]urea;

N-[3(R,S)-5-cyclohexyl-2,3-dihydro-1-methyl-2-oxo-1H-1,4-benzodiazepin-3-yl]N'-[3-(1,1-dimethylethyloarbonylamino sulphonyl)phenyl]urea;

N-[3(R)-5-cyclohexyl-2,3-dihydro-1-methyl-2-oxo-1H-1,4-benzodiazepin-3-yl]N'-[3-(2-methylphenylsulphonylamino carbonyl)phenyl]urea;

N- [3 (R) -5-cyclohexyl-2,3-dihydro-1-methyl-2-oxo-1H-1,4-benzodiazepin-3-yl ]N'- [4-methyl-3- (methylsulphonylamino carbonyl) phenyl]urea;

N- [3 (S) -5-cyclohexyl-2,3-dihydro-1-methyl-2-oxo-1H-1,4-benzodiazepin-3-yl]N'-[3-(phenylsulphonylamino carbonyl)phenyl]urea;

N-[3(R,S)-5-cyclopentyl-2,3-dihydro-1-propyl-2-oxo-1H-1,4-benzodiazepin-3-yl]N'-[3-(isopropylsulphonylamino carbonyl)phenyl]urea;

N-[3(R,S)-5-cyclopentyl-2,3-dihydro-1-propyl-2-oxo-1H-1,4-benzodiazepin-3-yl]N'-[3-(1,1-dimethylethylsulphonyl aminocarbonyl)phenyl]urea;

N-[3(R,S)-5-cyclopentyl-2,3-dihydro-1-methyl-2-oxo-1H-1,4-benzodiazepin-3-yl]N'-[3-(isopropylsulphonylamino carbonyl)phenyl]urea;

N-[3(R,S)-5-cyclopentyl-2,3-dihydro-1-methyl-2-oxo-1H-1,4-benzodiazepin-3-yl]N'-[3-(1,1-dimethylethylsulphonyl aminocarbonyl)phenyl]urea;

N-[3(R,S)-5-cyclopentyl-2,3-dihydro-1-methyl-2-oxo-1H-1,4-benzodiazepin-3-yl]N'-[3-(phenylsulphonylamino carbonyl)phenyl]urea;

N-[3(R,S)-5-cyclobutyl-2,3-dihydro-1-methyl-2-oxo-1H-1,4-benzodizepin-3-yl]N'-[3-methylphenyl]urea;

N-[3(R,S)-5-cyclohexyl-2,3-dihydro-1-methyl-2-oxo-1H-1,4-benzodiazepin-3-yl]N'-[3(R,S)-methylsulphinyl)phenyl]urea;

N-[3(R,S)-5-cyclohexyl-2,3-dihydro-1-methyl-2-oxo-1H-1,4-benzodiazepin-3-yl]N'-[3-(5-hydroxy-4-pyron-2-yl)phenyl]urea;

N-[3(R,S)-5-cyclohexyl-2,3-dihydro-1-methyl-2-oxo-1H-1,4-benzodiazepin-3-yl]N'-[3,4-dihydro-2,2-dioxo-4-oxo-1H-2,3-benzothiazin-6-yl]urea;

N-[3(R,S)-5-cyclohexyl-2,3-dihydro-1-methyl-2-oxo-1H-1,4-benzodiazepin-3-yl]N'-[3-(2-(imidazol-3yl)ethyl)phenyl]urea;

N-[3(R)-5-cyclohexyl-2,3-dihydro-1-methyl-2-oxo-1H-1,4-benzodiazepin-3-yl]N'-[4-methyl-3-(2-methylphenyl sulphonylaminocarbonyl)phenyl]urea;

N-[3(R)-5-cyclohexyl-2,3-dihydro-1-methyl-2-oxo-1H-1,4-benzodiazepin-3-yl]N'-[3-(2-chlorophenylsulphonyl aminocarbonyl)phenyl]urea;

N-[3(S)-5-cyclohexyl-2,3-dihydro-1-methyl-2-oxo-1H-1,4-benzodiazepin-3-yl]N'-[3-phenylsulphonylaminocarbonyl) phenyl]urea; and salts and prodrugs thereof.

10. A pharmaceutical composition comprising a therapeutically effective amount of the compound as claimed in claim 1 in association with a pharmaceutically acceptable carrier therefor.

11. A method for the treatment or prevention of a physiological disorder involving CCK and/or gastrin, which method comprises administration to a patient in need thereof of a CCK and/or gastrin reducing amount of a compound according to claim 1.

12. A method as claimed in claim 11 for the treatment or prevention of anxiety.

13. A method as claimed in claim 11 for the treatment or prevention of panic.

14. A method as claimed in claim 11 for the treatment of pain.

15. An intermediate of formula (A):

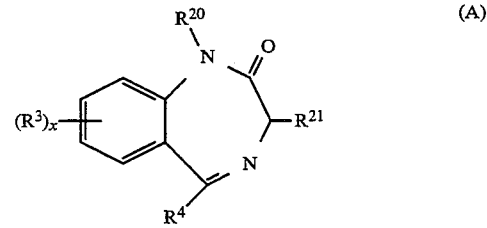

wherein $R^3$, $R^4$ and x are as defined for formula (I); $R^{20}$ is selected from hydrogen and $R^1$ as defined for formula (I); and $R^{21}$ is selected from $NH_2$, and an activated carbamate of the formula

wherein Ar is phenyl, unsubstituted or substituted with nitro.

* * * * *